United States Patent
Gross et al.

(10) Patent No.: US 9,284,332 B2
(45) Date of Patent: Mar. 15, 2016

(54) PROCESS FOR THE PREPARATION OF IMIDAZO[2,1-B][1,3]BENZOTHIAZOLE DERIVATIVES

(75) Inventors: Timothy David Gross, San Diego, CA (US); Rathan Prasad Achampeta, Secunderabad-A.P (IN); Janakiram Rao Citineni, Florence, SC (US)

(73) Assignee: Ambit Biosciences Corporation, San Diego, CA (US)

( * ) Notice: Subject to any disclaimer, the term of this patent is extended or adjusted under 35 U.S.C. 154(b) by 651 days.

(21) Appl. No.: 13/508,020

(22) PCT Filed: Nov. 4, 2010

(86) PCT No.: PCT/US2010/055399
§ 371 (c)(1),
(2), (4) Date: Sep. 14, 2012

(87) PCT Pub. No.: WO2011/056939
PCT Pub. Date: May 12, 2011

(65) Prior Publication Data
US 2013/0005966 A1    Jan. 3, 2013

Related U.S. Application Data

(60) Provisional application No. 61/258,550, filed on Nov. 5, 2009.

(51) Int. Cl.
*C07D 265/30* (2006.01)
*C07D 513/04* (2006.01)

(52) U.S. Cl.
CPC .................................... *C07D 513/04* (2013.01)

(58) Field of Classification Search
CPC ............. C07D 295/023; C07D 265/30; C07D 213/02; C07D 213/74; C07D 295/027
USPC .................... 544/106, 135; 548/151
See application file for complete search history.

(56) References Cited

U.S. PATENT DOCUMENTS

| 7,820,657 B2 | 10/2010 | Bhagwat et al. |
| 7,968,543 B2 | 6/2011 | James et al. |
| 8,129,374 B2 | 3/2012 | Bhagwat et al. |
| 2007/0232604 A1* | 10/2007 | Bhagwat ............ C07D 513/04 514/232.8 |
| 2009/0131426 A1 | 5/2009 | Bhagwat et al. |
| 2012/0129850 A1 | 5/2012 | Bhagwat et al. |

FOREIGN PATENT DOCUMENTS

| WO | WO 2009/038757 | 3/2009 |
| WO | WO 2010/054058 | 5/2010 |

OTHER PUBLICATIONS

Chao et al., 2009, "Identification of N-(5-*tert*-Butyl-isoxazol-3-yl)-N$^1$-{4-[7-(2-morpholin-4-yl-ethoxy)imidazol[2,1-b][1,3]benzothiazol-2-yl]phenyl}urea Dihydrochloride (AC220), a Uniquely Potent, Selective, and Efficacious FMS-Like Tyrosine Kinase-3 (FLT3) Inhibitor," Journal of Medicinal Chemistry, 52, 7808-7816.

* cited by examiner

*Primary Examiner* — Nyeemah A Grazier
*Assistant Examiner* — Sagar Patel
(74) *Attorney, Agent, or Firm* — Jones Day

(57) ABSTRACT

Provided herein are process for the preparation of N-(5-ferf-butyl-isoxazol-3-yl)-N'-{4-[7-(2-morpholin-4-yl-ethoxy)imidazo[2,1-fe][1,3]benzothiazol-2-yl]phenyl}urea, or a pharmaceutically acceptable salt, solvate, hydrate, or polymorph thereof. N-(5-tert-Butyl-isoxazol-3-yl)-N'-{4-[7-(2-morpholin-4-yl-ethoxy)imidazo[2,1-&][1,3]benzo-thiazol-2-yl]phenyl}urea is useful for treating, preventing, and/or managing diseases or conditions, including but not limited to, proliferative diseases, FLT-3 mediated diseases, and cancers. N-(5-ferf-Butyl-isoxazol-3-yl)-N'-{4-[7-(2-morpholin-4-yl-ethoxy)imidazo[2,1-&][1,3]benzothiazol-2-yl]phenyl}urea is represented by the structure:

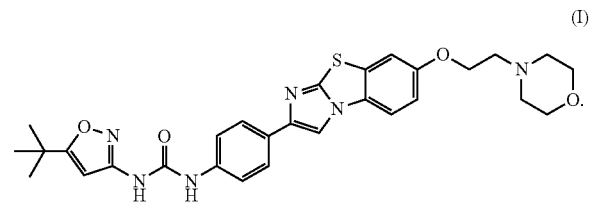

(I)

50 Claims, 25 Drawing Sheets

Method Info : Method: AMB003H
Column: Waters XTerra RP18 5 μm, 4.6 x 150 mm
Mobile Phase: (A) 0.1% H3PO4 in H2O   (B) 0.1% H3PO4 in ACN
Column Temp.: 40 °C
Wavelength: 230 nm
Injection Volume: 5 μL
Flow Rate: 1.0 ml/min Sample Info : 25 mg/50 ml DMSO + 40 drops of water ---->1ml aliqout taken then added 8 drops of mobile phase a

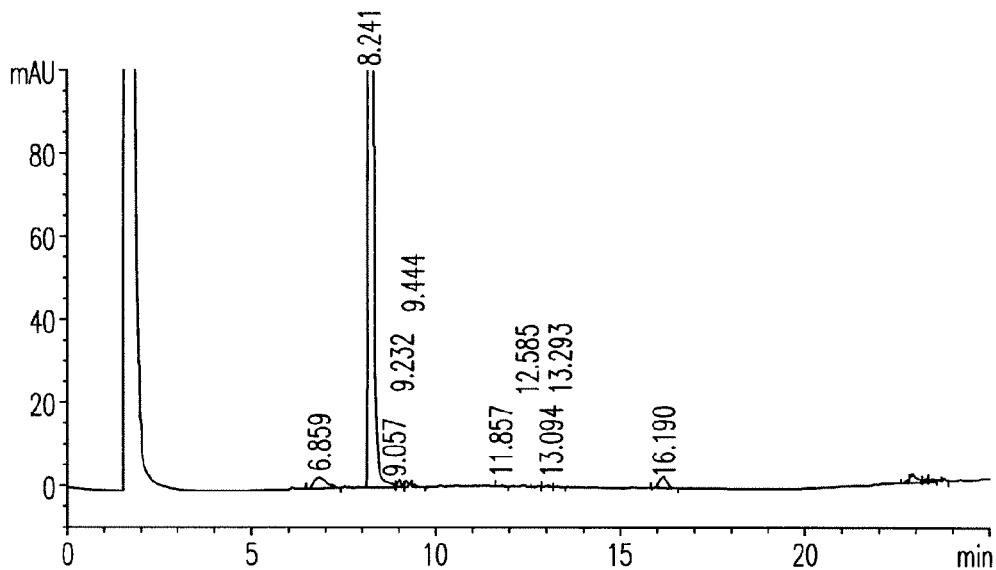

Signal 1: VWD1 A, Wavelength=230 nm

| Peak # | RetTime [min] | Type | Width [min] | Area mAU *s | Height [mAU] | Area % |
|---|---|---|---|---|---|---|
| 1 | 6.859 | MF | 0.3885 | 60.76836 | 2.60669 | 0.7876 |
| 2 | 8.241 | MF R | 0.0968 | 7517.27832 | 1293.71741 | 97.4277 |
| 3 | 9.057 | MF | 0.0975 | 11.17697 | 1.91105 | 0.1449 |
| 4 | 9.232 | MF | 0.0824 | 8.55049 | 1.73048 | 0.1108 |
| 5 | 9.444 | MF | 0.1475 | 6.57199 | 7.42414e-1 | 0.0852 |
| 6 | 11.857 | MF | 0.2002 | 3.76734 | 3.13612e-1 | 0.0488 |
| 7 | 12.585 | MF | 0.3250 | 6.99195 | 3.58530e-1 | 0.0906 |
| 8 | 13.094 | MF | 0.2197 | 5.40773 | 4.10274e-1 | 0.0701 |
| 9 | 13.293 | MF | 0.2499 | 4.44889 | 2.96713e-1 | 0.0577 |
| 10 | 16.190 | MM | 0.2212 | 35.89286 | 2.70495 | 0.4652 |
| 11 | 22.830 | MF | 0.1144 | 6.30667 | 9.19064e-1 | 0.0817 |
| 12 | 22.929 | FM | 0.1914 | 27.26313 | 2.37431 | 0.3533 |
| 13 | 23.291 | FM | 0.1366 | 7.70603 | 9.40003e-1 | 0.0999 |
| 14 | 23.358 | FM | 0.0789 | 3.45483 | 7.29610e-1 | 0.0448 |
| 15 | 23.508 | FM | 0.1191 | 5.37376 | 7.51835e-1 | 0.0696 |
| 16 | 23.778 | FM | 0.1003 | 4.78815 | 7.95536e-1 | 0.0621 |

Totals :                                       7715.74746    1311.30247

FIG.10

Method Info  : Method: AMB003H
　　　　　　　Column: Waters XTerra RP18 5 μm, 4.6 x 150 mm
　　　　　　　Mobile Phase: (A) 0.1% H3PO4 in H2O  (B) 0.1% H3PO4 in ACN
　　　　　　　Column Temp.: 40 °C
　　　　　　　Wavelength: 230 nm
　　　　　　　Injection Volume: 5 μL
　　　　　　　Flow Rate: 1.0 ml/min
Sample Info  : 30.42 mg/100 mL 3:1 mpa:mpb Signal 1: VWD1 A, Wavelength=230 nm

| Peak # | RetTime [min] | Type | Width [min] | Area mAU *s | Height [mAU] | Area % |
|---|---|---|---|---|---|---|
| 1 | 1.487 | FM | 0.0756 | 14.10570 | 3.11132 | 0.2642 |
| 2 | 3.202 | MF | 0.1989 | 5225.44336 | 437.82986 | 97.8587 |
| 3 | 4.039 | FM | 0.0853 | 36.50433 | 7.13237 | 0.6836 |
| 4 | 4.416 | FM | 0.0910 | 5.08042 | 9.30318e-1 | 0.0951 |
| 5 | 4.624 | FM | 0.0784 | 4.33624 | 9.21674e-1 | 0.0812 |
| 6 | 4.697 | FM | 0.0661 | 2.70796 | 6.83231e-1 | 0.0507 |
| 7 | 8.000 | FM | 0.1540 | 3.07774 | 3.33154e-1 | 0.0576 |
| 8 | 8.282 | FM | 0.0833 | 48.52591 | 9.70672 | 0.9088 |
| Totals : | | | | 5339.78166 | 460.64866 | |

Method Info : Method: AMB003H
Column: Waters XTerra RP18 5 μm, 4.6 x 150 mm
Mobile Phase: (A) 0.1% H3PO4 in H2O  (B) 0.1% H3PO4 in ACN
Column Temp.: 40 °C
Wavelength: 230 nm
Injection Volume: 5 μL
Flow Rate: 1.0 ml/min Sample Info : 24.95 mg/50 mL diluent Signal 1: VWD1 A, Wavelength=230 nm

| Peak # | RetTime [min] | Type | Width [min] | Area mAU *s | Height [mAU] | Area % |
|---|---|---|---|---|---|---|
| 1 | 17.335 | MF | 0.2341 | 4507.15771 | 320.83109 | 99.7756 |
| 2 | 18.214 | FM | 0.3415 | 3.80539 | 1.85738e-1 | 0.0842 |
| 3 | 21.904 | FM | 0.1004 | 6.32988 | 1.05067 | 0.1401 |

Totals : 4517.29299  322.06750

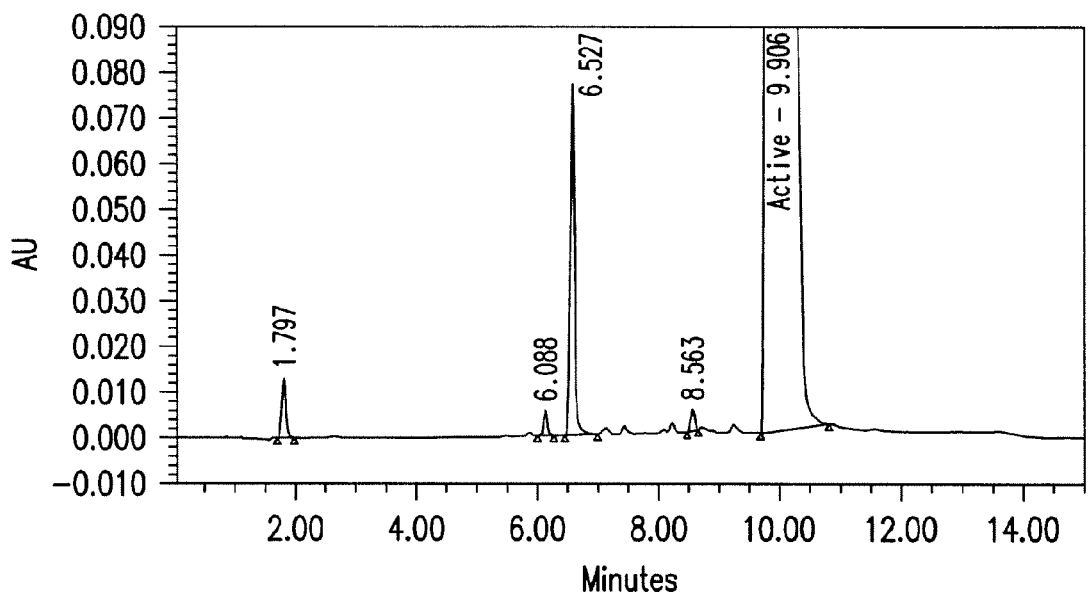
| | RRT | RT | Area | Height |
|---|---|---|---|---|
| 1 | 0.18 | 1.797 | 62207 | 12974 |
| 2 | 0.60 | 6.088 | 25460 | 5591 |
| 3 | 0.64 | 6.527 | 367619 | 76785 |
| 4 | 0.84 | 8.563 | 21995 | 4651 |
| 5 | Active | 9.906 | 49498261 | 2786037 |
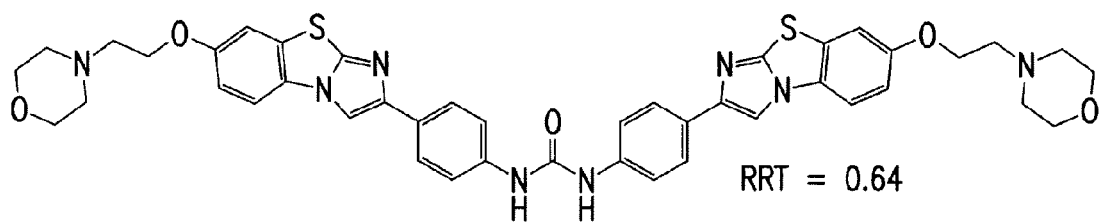
RRT = 0.64
FIG. 17

Method Info : Method: AMB003H
Column: Waters XTerra RP18 5 μm, 4.6 x 150 mm
Mobile Phase: (A) 0.1% H3PO4 in H2O  (B) 0.1% H3PO4 in ACN
Column Temp.: 40 °C
Wavelength: 230 nm
Injection Volume: 5 μL
Flow Rate: 1.0 ml/min Sample Info : 30.53 mg/50 mL diluent Signal 1: VWD1 A, Wavelength=230 nm

| Peak # | RetTime [min] | Type | Width [min] | Area mAU *s | Height [mAU] | Area % |
|---|---|---|---|---|---|---|
| 1 | 7.232 | MM | 0.0712 | 1.62116 | 3.79667e-1 | 0.0225 |
| 2 | 8.385 | MM | 0.0864 | 3.44859e-1 | 6.65311e-2 | 4.789e-3 |
| 3 | 8.739 | MM | 0.0960 | 9.41554e-1 | 1.63473e-1 | 0.0131 |
| 4 | 9.482 | MF | 0.0934 | 7186.62598 | 1282.05469 | 99.8072 |
| 5 | 10.643 | MF | 0.0901 | 2.82761 | 5.22984e-1 | 0.0393 |
| 6 | 10.745 | FM | 0.0891 | 1.61736 | 3.02592e-1 | 0.0225 |
| 7 | 20.973 | MM | 0.2294 | 1.81145 | 1.01955e-1 | 0.0252 |
| 8 | 22.912 | MF | 0.1194 | 2.21065 | 3.08700e-1 | 0.0307 |
| 9 | 23.004 | FM | 0.0661 | 3.33909e-1 | 8.42000e-2 | 4.637e-3 |
| 10 | 23.712 | MM | 0.0767 | 2.17176 | 4.71896e-1 | 0.0302 |

Totals :                                7200.50628    1284.45669

Method Info : Method: AMB003H
Column: Waters XTerra RP18 5 μm, 4.6 x 150 mm
Mobile Phase: (A) 0.1% H3PO4 in H2O  (B) 0.1% H3PO4 in ACN
Column Temp.: 40 °C
Wavelength: 230 nm
Injection Volume: 5 μL
Flow Rate: 1.0 ml/min Sample Info : 30.60 mg/50 mL diluent Signal 1: VWD1 A, Wavelength=230 nm

| Peak # | RetTime [min] | Type | Width [min] | Area mAU *s | Height [mAU] | Area % |
|---|---|---|---|---|---|---|
| 1 | 7.228 | MM | 0.0728 | 1.93663 | 4.43618e-1 | 0.0265 |
| 2 | 8.379 | MM | 0.0796 | 3.36725e-1 | 7.05237e-2 | 4.600e-3 |
| 3 | 8.743 | MF | 0.1018 | 1.01066 | 1.65446e-1 | 0.0138 |
| 4 | 8.956 | FM | 0.0733 | 1.31567e-1 | 2.99323e-2 | 1.797e-3 |
| 5 | 9.476 | MF | 0.0932 | 7306.32959 | 1305.95142 | 99.8145 |
| 6 | 10.435 | MM | 0.0729 | 3.23988e-1 | 7.40464e-2 | 4.426e-3 |
| 7 | 10.634 | MF | 0.0880 | 2.70181 | 5.11437e-1 | 0.0369 |
| 8 | 10.736 | FM | 0.0811 | 1.36080 | 2.79695e-1 | 0.0186 |
| 9 | 21.077 | MM | 0.2086 | 1.91172 | 1.18510e-1 | 0.0261 |
| 10 | 22.903 | MM | 0.1115 | 1.83010 | 2.73525e-1 | 0.0250 |
| 11 | 23.709 | MM | 0.0735 | 2.03110 | 4.60706e-1 | 0.0277 |
| Totals : | | | | 7319.90468 | 1308.37886 | |

US 9,284,332 B2

PROCESS FOR THE PREPARATION OF IMIDAZO[2,1-B][1,3]BENZOTHIAZOLE DERIVATIVES

I. CROSS REFERENCE TO RELATED APPLICATION

This application is a §371 national phase application of International Patent Application No. PCT/US2010/055399, filed Nov. 4, 2010, which claims priority to U.S. Provisional Patent Application No. 61/258,550, filed Nov. 5, 2009, the contents of both of which are is hereby incorporated by reference herein in their entireties.

II. FIELD

Provided herein are processes for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt, solvate, hydrate, or polymorph thereof. N-(5-tert-Butyl-isoxazol-3-yl)-N'-{4-[7-(2-morpholin-4-yl-ethoxy)imidazo[2,1-b][1,3]benzothiazol-2-yl]phenyl}urea is useful for treating, preventing, and/or managing diseases or conditions, including but not limited to, proliferative diseases, FLT-3 mediated diseases, and cancers.

III. BACKGROUND

Protein kinases are enzymes that catalyze the phosphorylation of hydroxyl groups on tyrosine, serine, and/or threonine residues of proteins. Protein kinases, for example, receptor tyrosine kinases (RTKs), may act as growth factor receptors and play a central role in signal transduction pathways regulating cellular functions, such as cell cycle, cell growth, cell differentiation, and cell death. Aberrant or excessive activity or disregulation of the activity of RTKs has been observed in many disease states, including benign and malignant proliferative disorders, as well as inflammatory disorders and immune system disorders that result from inappropriate activation of the immune system to cause, for example, autoimmune diseases.

Inhibitors of certain kinases may also have utility in the treatment of diseases where the kinase, although not misregulated, is essential for the maintenance of the disease state. In these cases, inhibition of the kinase activity would act either as a palliative or as a cure for these diseases. For example, many viruses, such as human papilloma virus, disrupt the cell cycle and drive cells into the S-phase of the cell cycle. See, e.g., Vousden, FASEB J. 7, 872-879 (1993). Inhibition of essential S-phase initiating activities by kinase inhibitors prevents cells from entering the DNA synthesis phase after viral infection, thereby disrupting the virus life cycle and preventing virus replication. The same principle may also be used to protect normal cells of the body from the toxicity of cell-cycle-specific chemotherapeutic agents. See, e.g., Stone et al., Cancer Res. 56, 3199-3202 (1996); Kohn et al., J. Cell. Biochem. 54, 44-52 (1994).

Fms-like tyrosine kinase 3 (FLT3), which is also known as FLK-2 (fetal liver kinase 2) and STK-1 (stem cell kinase 1), plays an important role in the proliferation and differentiation of hematopoietic stem cells. FLT3 receptor kinase is expressed in normal hematopoietic cells, placenta, gonads, and brain. This kinase is expressed at very high levels on the cells of more than 80% of myeloid patients and a fraction of acute lymphoblastic leukemia patients. This enzyme can also be found on the cells from patients with chronic myeloid leukemia in lymphoid blast crisis.

In addition, FLT3 kinase is mutated in 30% of acute myeloid leukemia (AML) and in a subset of acute lymphoblastic leukemia (ALL). See, e.g., Gilliland et al., Blood 100, 1532-1542 (2002); Stirewalt et al., Nat. Rev. Cancer 3, 650-665 (2003). The most common activating mutations in FLT3 are internal tandem duplications within the juxtamembrane region. Point mutations, insertions, or deletions in the kinase domain are less common. Some of these mutant FLT3 kinases are constitutively active. FLT3 mutations have been associated with a poor prognosis. See, e.g., Malempati et al., Blood 104, 11 (2004).

More than a dozen known FLT3 inhibitors are being developed and some have shown promising clinical effects against AML. See, e.g., Levis et al. Int. J. Hematol. 82, 100-107 (2005). It has been reported that some small-molecule FLT3 inhibitors are effective in inducing apoptosis in cell lines with FLT3-activating mutations and prolonging survival of mice that express mutant FLT3 in their bone marrow cells. See, e.g., Levis et al., Blood 99, 3885-3891 (2002); Kelly et al., Cancer Cell 1, 421-432 (2002); Weisberg et al., Cancer Cell 1, 433-443 (2002); Yee et al., Blood 100, 2941-2949 (2002).

In addition, cancer is a major public health problem worldwide. In the United States alone, approximately 560,000 people died of cancer in 2006. See, e.g., U.S. Mortality Data 2006, National Center for Health Statistics, Centers for Disease Control and Prevention (2009). Many types of cancer have been described in the medical literature. Examples include, but are not limited to, cancer of the blood, bone, skin, lung, colon, breast, prostate, ovary, brain, kidney, bladder, pancreas, and liver. The incidence of cancer continues to climb as the general population ages and as new forms of cancer develop. A continuing need exists for effective therapies to treat subjects with cancer.

Kinase inhibitors are currently being explored for the treatment of diseases such as proliferative diseases, FLT-3 mediated diseases, and cancers. Despite the success in identification of small molecules that inhibit kinases, there continues to be a need for new kinase inhibitor compounds and safe, efficient, scalable, and/or economically viable processes to prepare these kinase inhibitor compounds, such as, for example, processes to prepare kinase inhibitors on a commercial scale suitable for human use, and/or processes having other potential advantages.

Provided herein are new processes to prepare N-(5-tert-butyl-isoxazol-3-yl)-N'-{4-[7-(2-morpholin-4-yl-ethoxy)imidazo[2,1-b][1,3]benzothiazol-2-yl]phenyl}urea. N-(5-tert-Butyl-isoxazol-3-yl)-N'-{4-[7-(2-morpholin-4-yl-ethoxy)imidazo[2,1-b][1,3]benzothiazol-2-yl]phenyl}urea is disclosed in U.S. Patent Application Publication Nos. 2007/0232604, 2009/0123418, and 2009/0131426, each of which is incorporated herein by reference in their entireties.

Citation of any references in this Section of the application is not to be construed as an admission that such references is prior art to the present application.

IV. SUMMARY

Provided herein are processes useful for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea (I), or a pharmaceutically acceptable salt, solvate, hydrate, or polymorph thereof. N-(5-tert-Butyl-isoxazol-3-yl)-N'-{4-[7-(2-morpholin-4-yl-ethoxy)imidazo[2,1-b][1,3]benzothiazol-2-yl]phenyl}urea is represented by the structure:

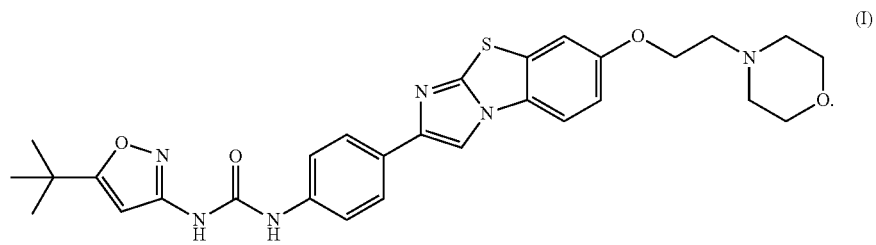 [SMILES: CC(C)(C)c1cc(NC(=O)Nc2ccc(-c3cn4c(n3)sc3cc(OCCN5CCOCC5)ccc34)cc2)no1]

In one embodiment, provided herein are, inter alia, safe, efficient, cost effective, and/or readily scaleable processes useful for the preparation of N-(5-tert-butyl-isoxazol-3-yl)-N'-{4-[7-(2-morpholin-4-yl-ethoxy)imidazo[2,1-b][1,3] benzothiazol-2-yl]phenyl}urea, or a pharmaceutically acceptable salt, solvate, hydrate, or polymorph thereof. In one embodiment, provided herein are processes useful for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt, solvate, hydrate, or polymorph thereof, that is substantially pure. In one embodiment, provided herein are processes useful for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt, solvate, hydrate, or polymorph thereof, that is suitable for use in humans.

In one embodiment, provided herein are processes for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea, or a pharmaceutically acceptable salt, solvate, hydrate, or polymorph thereof, comprising the step of reacting 7-(2-morpholin-4-yl-ethoxy)-2-(4-aminophenyl) imidazo[2,1-b]benzothiazole with a 5-tert-butylisoxazol-3-ylcarbamate derivative to yield N-(5-tert-butyl-isoxazol-3-yl)-N'-{4-[7-(2-morpholin-4-yl-ethoxy)imidazo[2,1-b][1,3] benzo-thiazol-2-yl]phenyl}urea. In one embodiment, the 5-tert-butylisoxazol-3-ylcarbamate derivative is phenyl 5-tert-butylisoxazol-3-ylcarbamate.

In one embodiment, the processes provided herein comprise any one, two, three, four, five, six, or seven of Steps A, B, C, D, E, F, and G described herein elsewhere.

In one embodiment, the process provided herein comprises the step ("Step A") of converting 2-amino-6-alkoxybenzothiazole (II), wherein $R^1$ is a suitable phenolic hydroxyl protecting group, to 2-amino-6-hydroxybenzothiazole (III). Suitable phenolic hydroxyl protecting groups are described, for example, in Greene & Wuts, "Protective Groups in Organic Synthesis," 4th Edition, Wiley Interscience, 2006, and Kocienski, "Protecting Groups," 3rd Edition, Thieme, 2005, each of which is incorporated herein by reference. In one embodiment, $R^1$ is optionally substituted $C_1$-$C_6$ alkyl. In one embodiment, $R^1$ is unsubstituted $C_1$-$C_6$ alkyl. In one embodiment, $R^1$ is methyl or ethyl. In one embodiment, $R^1$ is methyl. In one embodiment, the reaction of Step A is carried out under conditions suitable for deprotecting the phenolic hydroxyl protecting group. See, e.g., Greene & Wuts, "Protective Groups in Organic Synthesis," 4th Edition, Wiley Interscience, 2006; Kocienski, "Protecting Groups," 3rd Edition, Thieme, 2005. In one embodiment, the reaction of Step A is carried out in the presence of hydrobromic acid (HBr), boron tribromide ($BBr_3$), hydroiodic acid (HI), or iodotrimethylsilane (TMSI). In one embodiment, the reaction of Step A is carried out in the presence of hydrobromic acid. In one embodiment, the reaction of Step A is carried out in aqueous HBr. In one embodiment, the reaction of Step A is carried out in aqueous HBr under a refluxing condition. In one embodiment, the reaction of Step A is carried out at a temperature of between about 105° C. and about 110° C. In one embodiment, the product of Step A is collected by filtration or centrifuge.

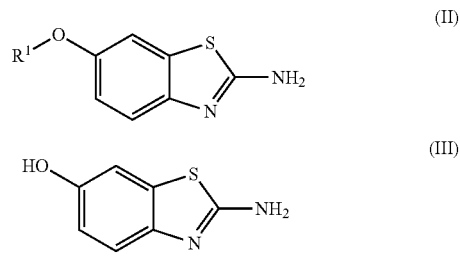

In one embodiment, the process provided herein comprises the step ("Step B") of reacting 2-amino-6-hydroxybenzothiazole (III) with compound (IV), wherein $X^1$ is a leaving group, to yield 2-(4-nitrophenyl)imidazo[2,1-b]benzothiazol-7-ol (V). In one embodiment, $X^1$ is halo, alkylsulfonate, or arylsulfonate. See, e.g., Prakash, et al., *Synlett* 1994, 221; Moriarty, et al., *Synthesis* 1992, 845. In one embodiment, $X^1$ is halo. In one embodiment, compound (IV) is 2-bromo-4'-nitroacetophenone. In one embodiment, the reaction of Step B is carried out in the presence of base. In one embodiment, the reaction of Step B is carried out in the presence of an organic or inorganic base. In one embodiment, the reaction of Step B is carried out in the presence of one or more carbonate or bicarbonate salts. In one embodiment, the reaction of Step B is carried out in the presence of sodium bicarbonate. In one embodiment, the reaction of Step B is carried out in a polar solvent. In one embodiment, the reaction of Step B is carried out in a protic solvent. In one embodiment, the reaction of Step B is carried out in alcoholic solvent. In one embodiment, the reaction of Step B is carried out in n-butanol. In one embodiment, the reaction of Step B is carried out in alcohol in the presence of base. In one embodiment, the reaction of Step B is carried out in alcohol in the presence of one or more carbonate or bicarbonate salts. In one embodiment, the reaction of Step B is carried out in n-butanol in the presence of base. In one embodiment, the reaction of Step B is carried out in n-butanol in the presence of one or more carbonate or bicarbonate salts. In one embodiment, the reaction of Step B is carried out in n-butanol under a refluxing condition. In one embodiment, the reaction of Step B is carried out at a temperature of between about 110° C. and about 115° C. In one embodiment, the product of Step B is collected by filtration or centrifuge.

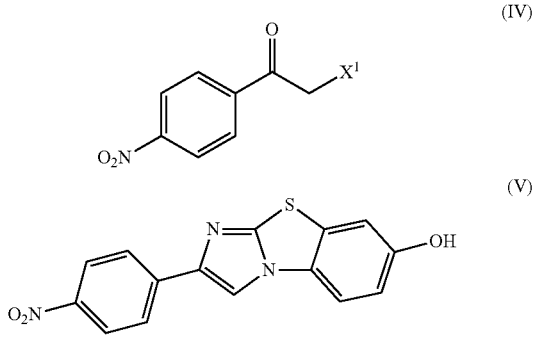

In one embodiment, the process provided herein comprises the step ("Step C") of reacting 2-(4-nitrophenyl)imidazo[2,1-b]benzothiazol-7-ol (V) with compound (VI), wherein $X^2$ is a leaving group, to yield 7-(2-morpholin-4-yl-ethoxy)-2-(4-nitrophenyl)imidazo[2,1-b]benzothiazole (VII). In one embodiment, $X^2$ is halo, alkylsulfonate, or arylsulfonate. See, e.g., Prakash, et al., *Synlett* 1994, 221; Moriarty, et al., *Synthesis* 1992, 845. In one embodiment, $X^2$ is halo. In one embodiment, $X^2$ is tosylate, nosylate, mesylate, or triflate. In one embodiment, compound (VI) is 4-(2-chloroethyl)morpholine. In one embodiment, the reaction of Step C is carried out in the presence of base. In one embodiment, the reaction of Step C is carried out in the presence of an organic or inorganic base. In one embodiment, the reaction of Step C is carried out in the presence of one or more carbonate or bicarbonate salts. In one embodiment, the reaction of Step C is carried out in the presence of potassium carbonate. In one embodiment, the reaction of Step C is carried out in the presence of tetrabutylammonium iodide. In one embodiment, the reaction of Step C is carried out in the presence of potassium carbonate and tetrabutylammonium iodide. In one embodiment, the reaction of Step C is carried out in a polar solvent. In one embodiment, the reaction of Step C is carried out in N,N-dimethylformamide (DMF). In one embodiment, the reaction of Step C is carried out at a temperature of between about 90° C. and about 110° C. In one embodiment, the reaction of Step C is carried out at a temperature of about 110° C. In one embodiment, the product of Step C is collected by filtration or centrifuge.

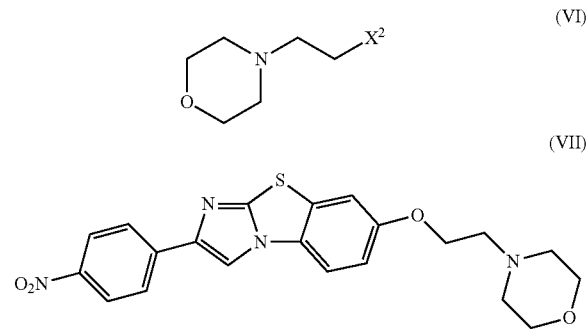

In one embodiment, the process provided herein comprises the step ("Step D") of reducing 7-(2-morpholin-4-yl-ethoxy)-2-(4-nitrophenyl)imidazo[2,1-b]benzothiazole (VII) to yield 7-(2-morpholin-4-yl-ethoxy)-2-(4-aminophenyl)imidazo[2,1-b]benzothiazole (VIII). In one embodiment, the reaction of Step D is carried out in the presence of hydrogen, or a hydrogen transfer reagent, including but not limited to, formic acid, ammonium formate, and cyclohexadiene. In one embodiment, the reaction of Step D is carried out in the presence of hydrogen. In one embodiment, the reaction of Step D is carried out in the presence of a reducing agent, including but not limited to, tin chloride, metallic tin or iron in the presence of acid, lithium aluminum hydride, sodium dithionite, and metallic samarium in the presence of a pyridinium catalyst. In one embodiment, the reaction of Step D is carried out in the presence of a reducing catalyst, including but not limited to, a palladium catalyst, a rhodium catalyst, and a ruthenium catalyst. In one embodiment, the reaction of Step D is carried out in the presence of a reducing catalyst, including but not limited to, palladium on carbon, palladium hydroxide on carbon, and Raney nickel (Raney Ni). In one embodiment, the reaction of Step D is carried out in the presence of Raney Ni. In one embodiment, the reaction of Step D is carried out in the presence of Raney Ni under hydrogen atmosphere. In one embodiment, the reaction of Step D is carried out in the presence of Raney Ni under about 150 psi hydrogen atmosphere. In one embodiment, the reaction of Step D is carried out in a polar solvent. In one embodiment, the reaction of Step D is carried out in methanol. In one embodiment, the reaction of Step D is carried out in tetrahydrofuran (THF). In one embodiment, the reaction of Step D is carried out in a mixture of methanol and THF. In one embodiment, the reaction of Step D is carried out in the presence of water. In one embodiment, the reaction of Step D is carried out at ambient temperature. In one embodiment, the reaction of Step D is carried out at a temperature of about 50° C. In one embodiment, the product of Step D is collected by filtration or centrifuge. In one embodiment, the product of Step D is collected by filtration or centrifuge in the presence of a non-polar solvent, such as heptane.

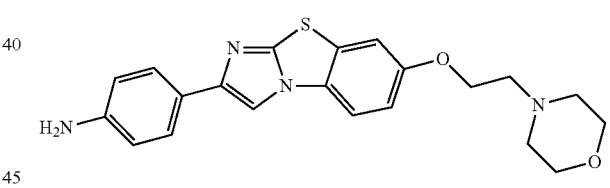

In one embodiment, the process provided herein comprises the step ("Step E") of converting 3-amino-5-tert-butyl isoxazole (IX) to a 5-tert-butylisoxazol-3-ylcarbamate derivative (X), wherein $R^2$ is optionally substituted aryl, heteroaryl, alkyl, or cycloalkyl. In one embodiment, $R^2$ is optionally substituted with one or more halo, nitro, cyano, alkyl, or alkoxyl. In one embodiment, $R^2$ is optionally substituted aryl or heteroaryl. In one embodiment, $R^2$ is aryl or heteroaryl optionally substituted with one or more halo, nitro, cyano, alkyl, or alkoxyl. In one embodiment, $R^2$ is optionally substituted phenyl. In one embodiment, $R^2$ is phenyl optionally substituted with one or more electron withdrawing substituents. In one embodiment, $R^2$ is phenyl optionally substituted with one or more halo, nitro, or cyano. In one embodiment, $R^2$ is phenyl optionally substituted with one or more halo or nitro. In one embodiment, $R^2$ is nitrophenyl. In one embodiment, $R^2$ is phenyl. In one embodiment, compound (X) is phenyl 5-tert-butylisoxazol-3-ylcarbamate. In one embodiment, the reaction of Step E is carried out in the presence of a carbamate forming reagent. In one embodiment, the reaction of Step E is carried out in the presence of a chloroformate reagent. In one embodiment, the reaction of Step E is carried out in the presence of phenyl chloroformate. In one embodiment, the reaction of Step E is carried out in the presence of base. In one embodiment, the reaction of Step E is carried out in the presence of one or more carbonate or bicarbonate salts. In one embodiment, the reaction of Step E is carried out in the presence of potassium carbonate. In one embodiment, the reaction of Step E is carried out in a polar solvent. In one embodiment, the reaction of Step E is carried out in THF. In one embodiment, the reaction of Step E is carried out at ambient temperature. In one embodiment, the reaction of Step E is carried out at a temperature of about 20° C. In one embodiment, the product of Step E is collected by filtration or centrifuge. In one embodiment, the product of Step E is collected by filtration or centrifuge in the presence of an anti-solvent, such as, e.g., a mixture of water and ethanol.

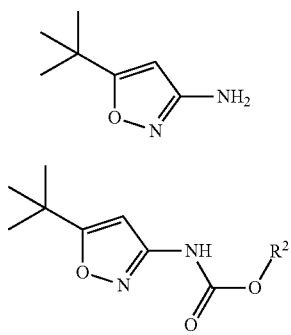

In one embodiment, the process provided herein comprises the step ("Step F") of reacting 7-(2-morpholin-4-yl-ethoxy)-2-(4-aminophenyl)imidazo[2,1-b]benzothiazole (VIII) with a 5-tert-butylisoxazol-3-ylcarbamate derivative (X) to yield N-(5-tert-butyl-isoxazol-3-yl)-N'-{4-[7-(2-morpholin-4-yl-ethoxy)imidazo[2,1-b][1,3]benzothiazol-2-yl]phenyl}urea (I). In one embodiment, the reaction of Step F is carried out in the presence of base. In one embodiment, the reaction of Step F is carried out in the presence of an organic or inorganic base. In one embodiment, the reaction of Step F is carried out in the presence of a tertiary amine. In one embodiment, the reaction of Step F is carried out in the presence of triethylamine. In one embodiment, the reaction of Step F is carried out in the presence of catalyst. In one embodiment, the reaction of Step F is carried out in the presence of 4-dimethylaminopyridine (DMAP). In one embodiment, the reaction of Step F is carried out in an aprotic solvent. In one embodiment, the reaction of Step F is carried out in dichloromethane. In one embodiment, the reaction of Step F is carried out at a temperature of about 40° C. In one embodiment, the reaction of Step F is carried out in dichloromethane under a refluxing condition. In one embodiment, the molar ratio of compound (X) relative to compound (VIII) used in the reaction of Step F is about 0.8 (i.e., [Compound (X)]/[Compound (VIII)]=0.8), about 0.9, about 1.0, about 1.1, about 1.2, about 1.3, about 1.4, about 1.5, about 1.6, about 1.7, about 1.8, about 1.9, or about 2.0. In one embodiment, the molar ratio of compound (X) relative to compound (VIII) used in the reaction of Step F is about 1.0, about 1.1, about 1.2, or about 1.3. In one embodiment, the molar ratio of compound (X) relative to compound (VIII) used in the reaction of Step F is between about 1.0 and about 1.5. In one embodiment, the product of Step F is collected by filtration or centrifuge.

In one embodiment, the process provided herein comprises the step ("Step G") of converting N-(5-tert-butyl-isoxazol-3-yl)-N'-{4-[7-(2-morpholin-4-yl-ethoxy)imidazo[2,1-b][1,3]benzothiazol-2-yl]phenyl}urea to an acid addition salt of N-(5-tert-butyl-isoxazol-3-yl)-N'-{4-[7-(2-morpholin-4-yl-ethoxy)imidazo[2,1-b][1,3]benzothiazol-2-yl]phenyl}urea. In one embodiment, the acid addition salt is a hydrochloride salt of N-(5-tert-butyl-isoxazol-3-yl)-N'-{4-[7-(2-morpholin-4-yl-ethoxy)imidazo[2,1-b][1,3]benzothiazol-2-yl]phenyl}urea. In one embodiment, the acid addition salt is N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride. In one embodiment, the salt formation reaction of Step G is carried out in a polar solvent. In one embodiment, the salt formation reaction of Step G is carried out in a protic solvent. In one embodiment, the salt formation reaction of Step G is carried out in methanol. In one embodiment, the salt formation reaction of Step G is carried out in the presence of aqueous hydrochloric acid. In one embodiment, the salt formation reaction of Step G is carried out at a temperature of about 65° C. In one embodiment, the salt formation reaction of Step G is carried out in methanol under a refluxing condition. In one embodiment, the salt formation reaction of Step G is carried out in the presence of greater than two equivalents of acid relative to the free base. In one embodiment, the molar ratio of the acid, e.g. hydrochloric acid, used in the reaction of Step G, relative to the free base, is about 1.0, about 1.5, about 2.0, about 2.5, or about 3.0. In one embodiment, the molar ratio of the acid, e.g. hydrochloric acid, used in the reaction of Step G, relative to the free base, is about 2.0, about 2.5, or about 3.0. In one embodiment, the product of the reaction of Step G is collected by filtration or centrifuge.

In one embodiment, the reaction of Step A, B, C, D, E, F, or G is carried to substantial completion. In one embodiment, the reaction of any one of the Steps described herein is monitored by methods, including but not limited to, HPLC, GC, or TLC.

V. BRIEF DESCRIPTION OF THE FIGURES

FIGS. 1a and 1b provide a synthetic scheme for Compound (I).

FIG. 10 represents an HPLC chromatogram of 7-(2-morpholin-4-yl-ethoxy)-2-(4-nitrophenyl)imidazo[2,1-b]benzothiazole (VII).

FIG. 17 represents an HPLC chromatogram of N-(5-tert-butyl-isoxazol-3-yl)-N'-{4-[7-(2-morpholin-4-yl-ethoxy)imidazo[2,1-b][1,3]benzothiazol-2-yl]phenyl}urea (I) prepared using a process disclosed previously, e.g., in U.S. Patent Publication 2009/0131426 (FIG. 66).

VI. DETAILED DESCRIPTION

Figure 1A:
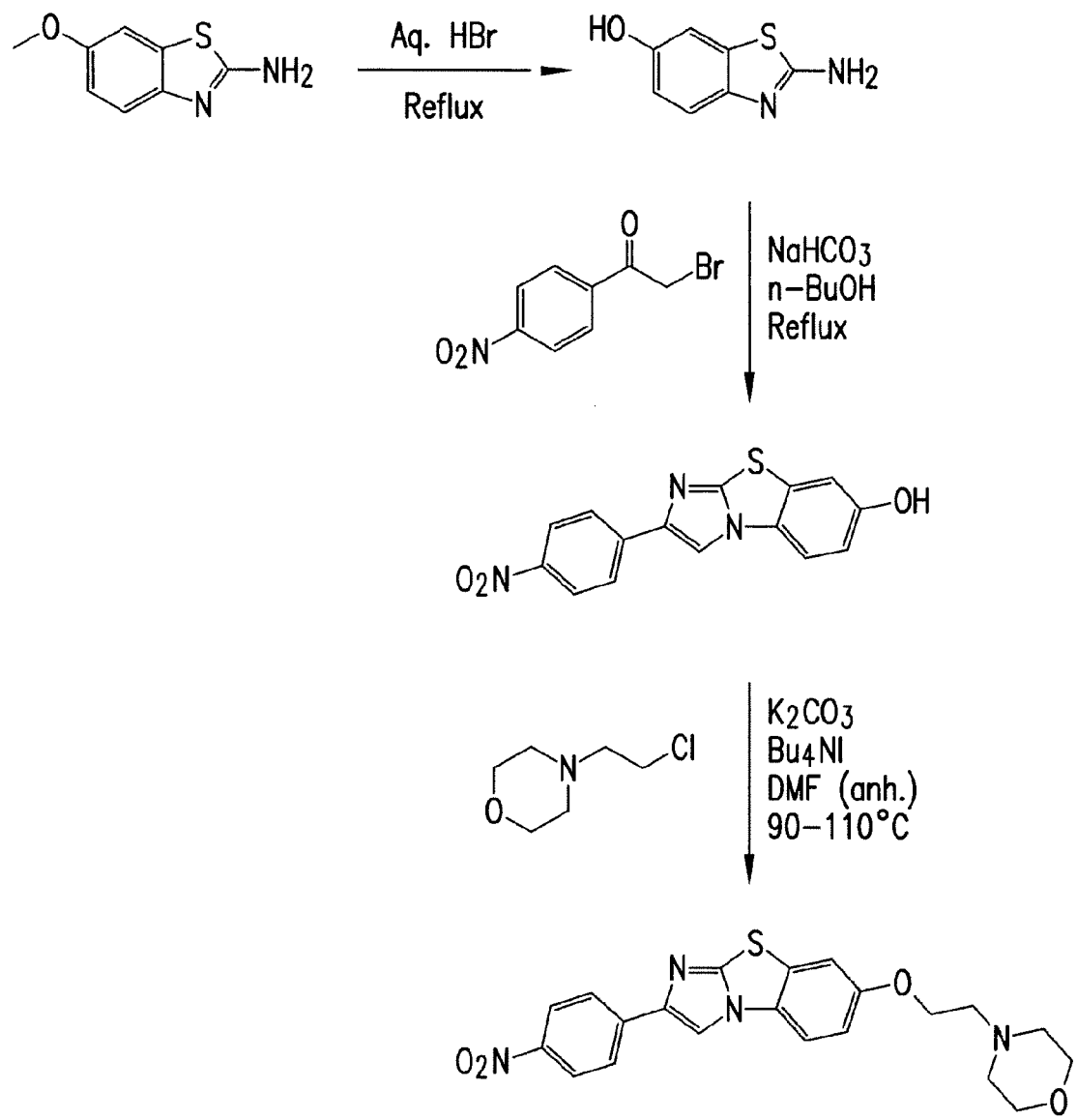
Figure 1B:
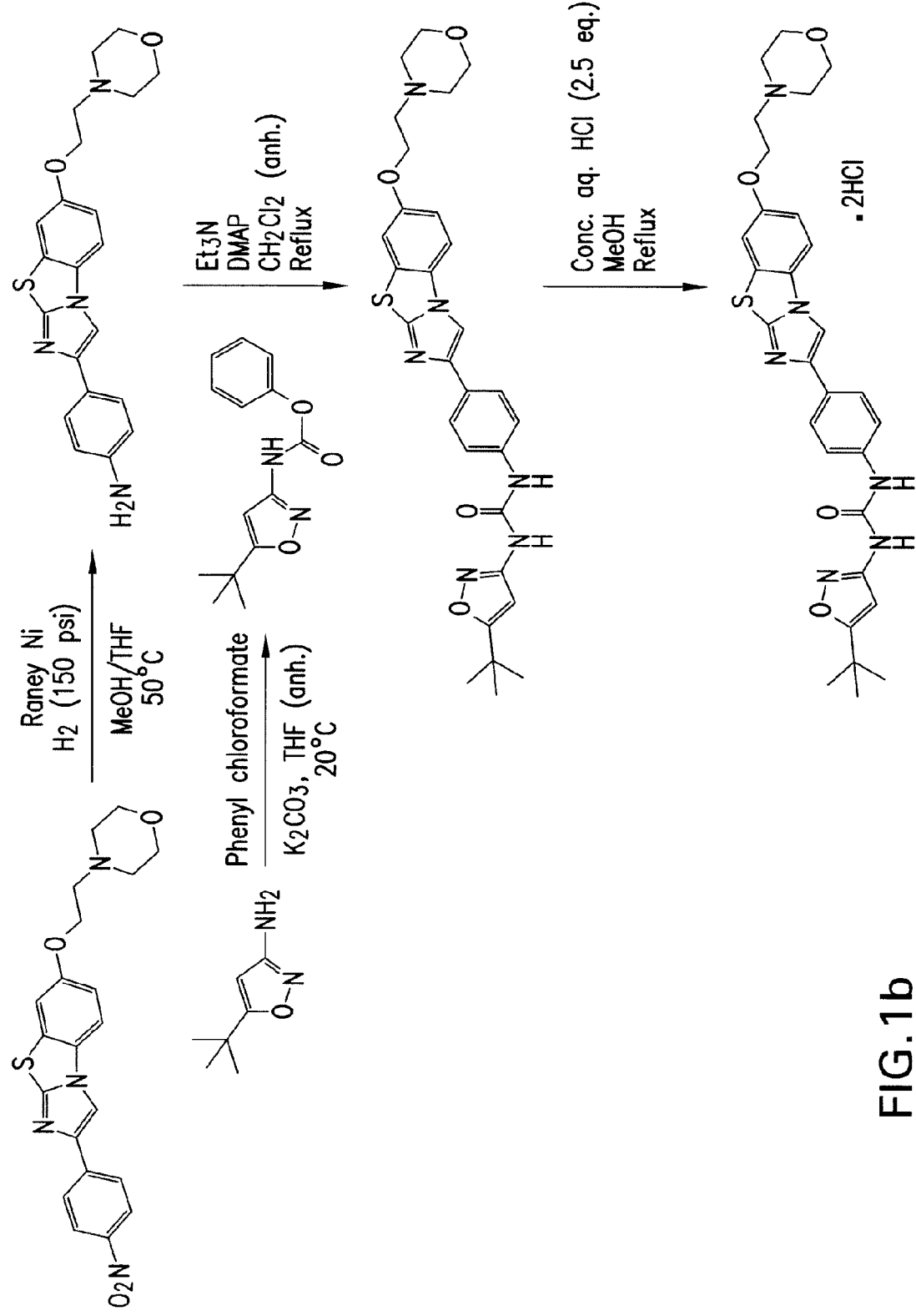
Figure 2:
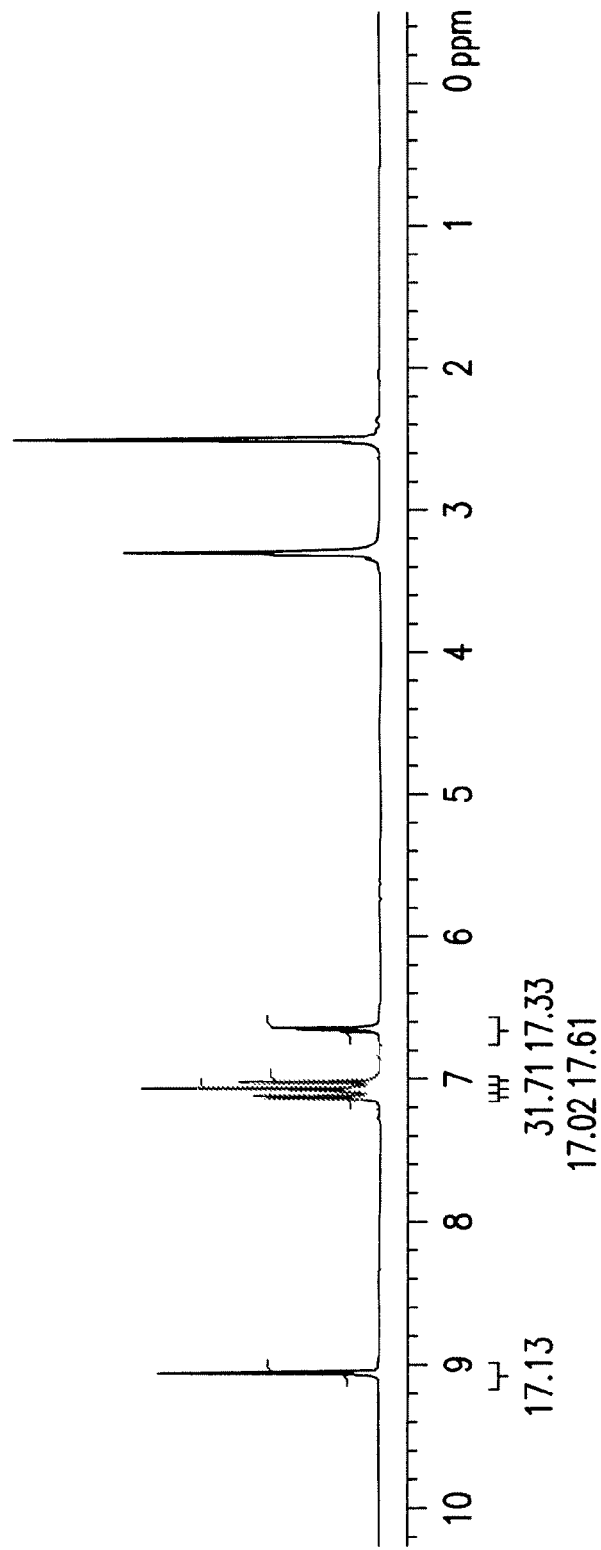
FIG. 2 represents a $^1$H NMR spectrum of 2-amino-6-hydroxybenzothiazole (III) in DMSO-$d_6$.
Figure 3:
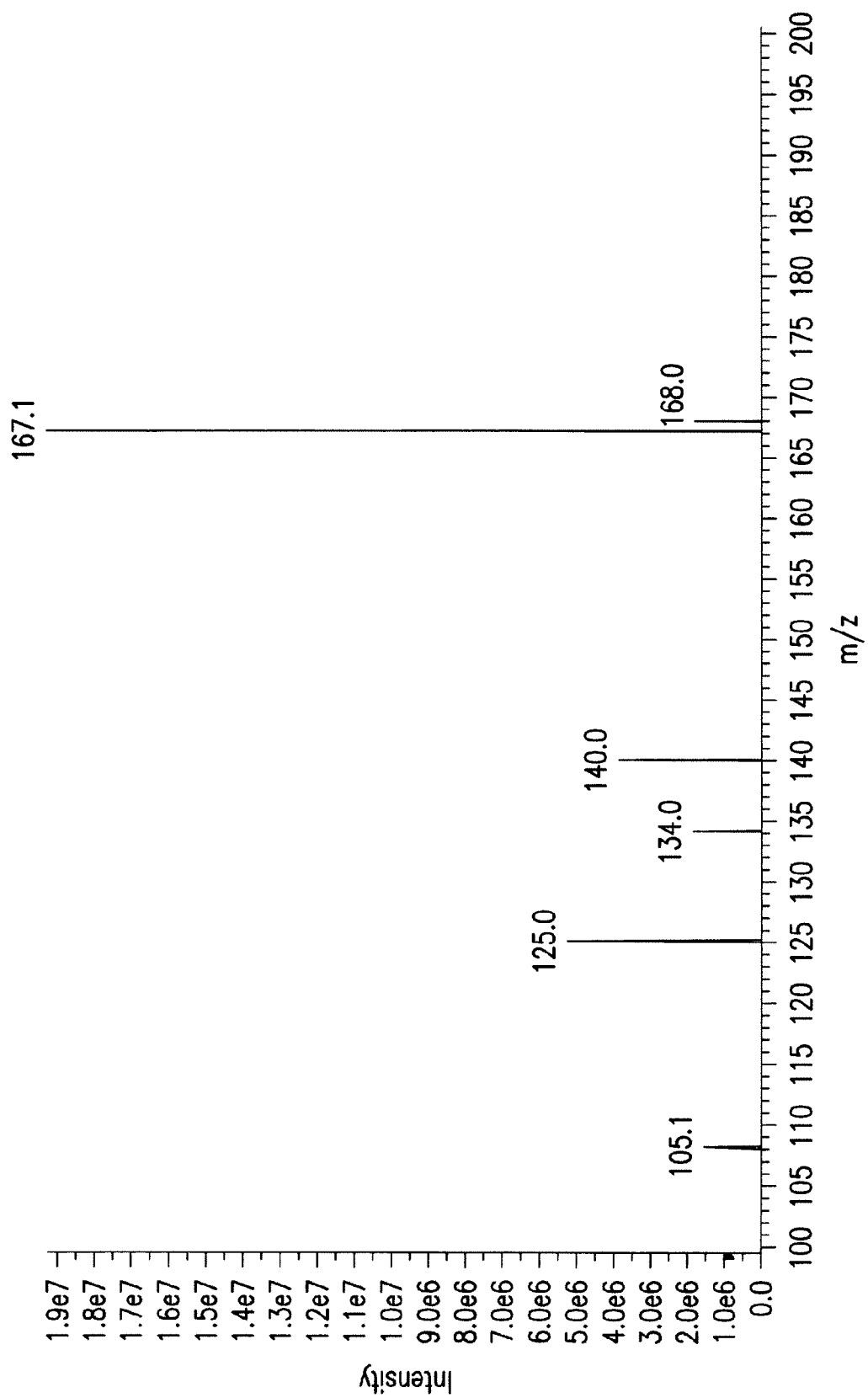
FIG. 3 represents an MS spectrum of 2-amino-6-hydroxybenzothiazole (III).
Figure 4:
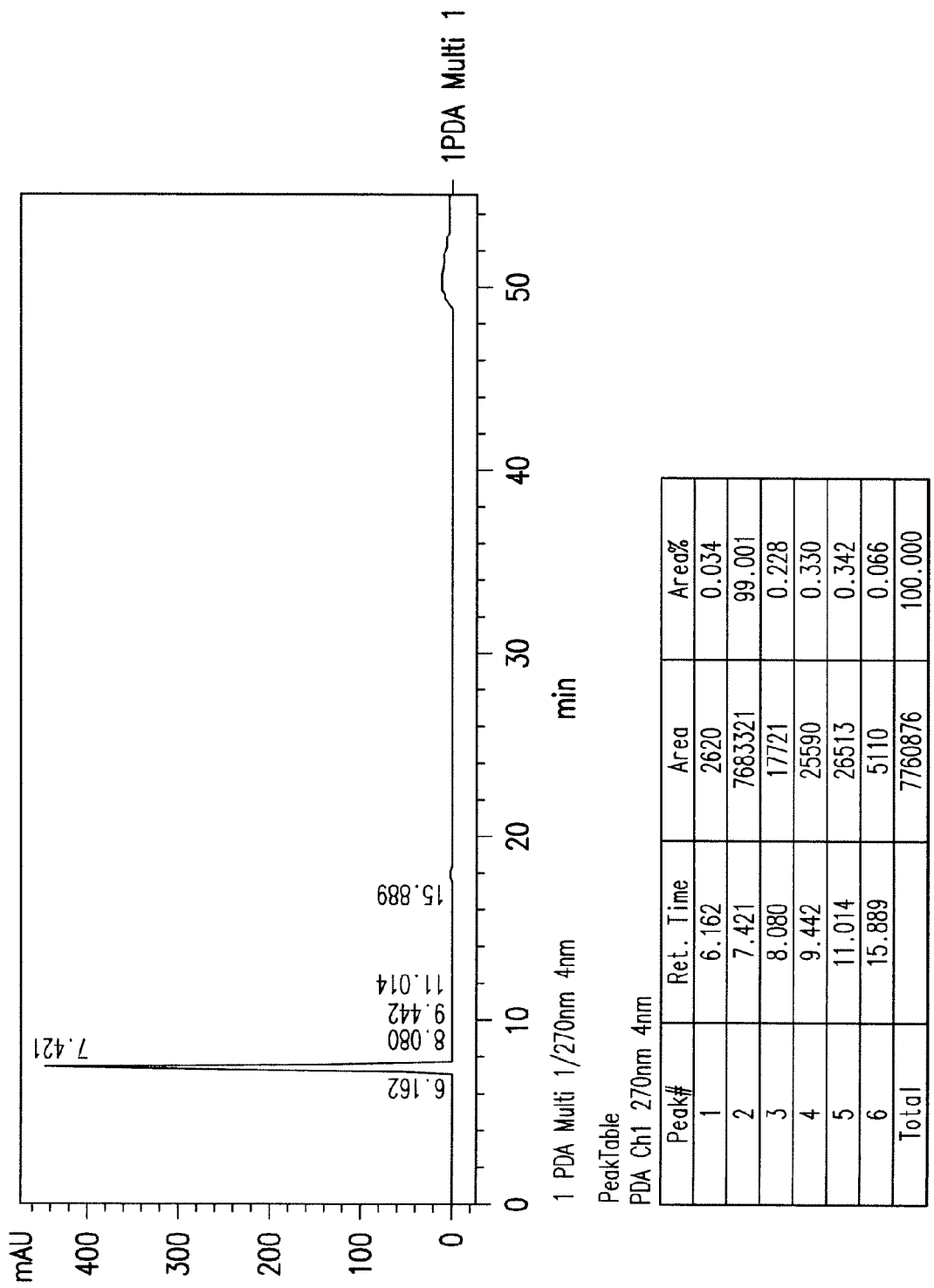
FIG. 4 represents an HPLC chromatogram of 2-amino-6-hydroxybenzothiazole (III).
Figure 5:
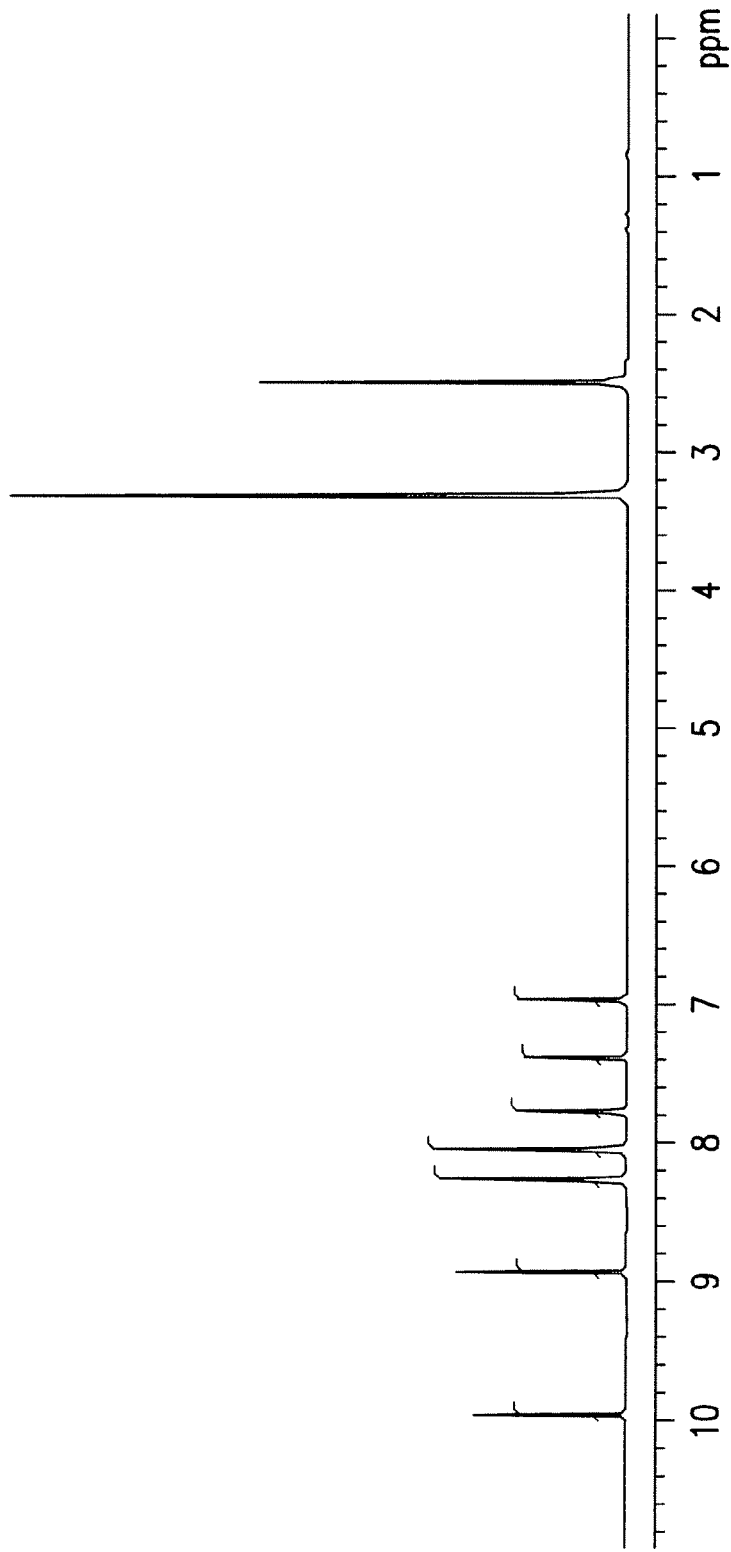
FIG. 5 represents a $^1$H NMR spectrum of 2-(4-nitrophenyl)imidazo[2,1-b]benzothiazol-7-ol (V) in DMSO-$d_6$.
Figure 6:
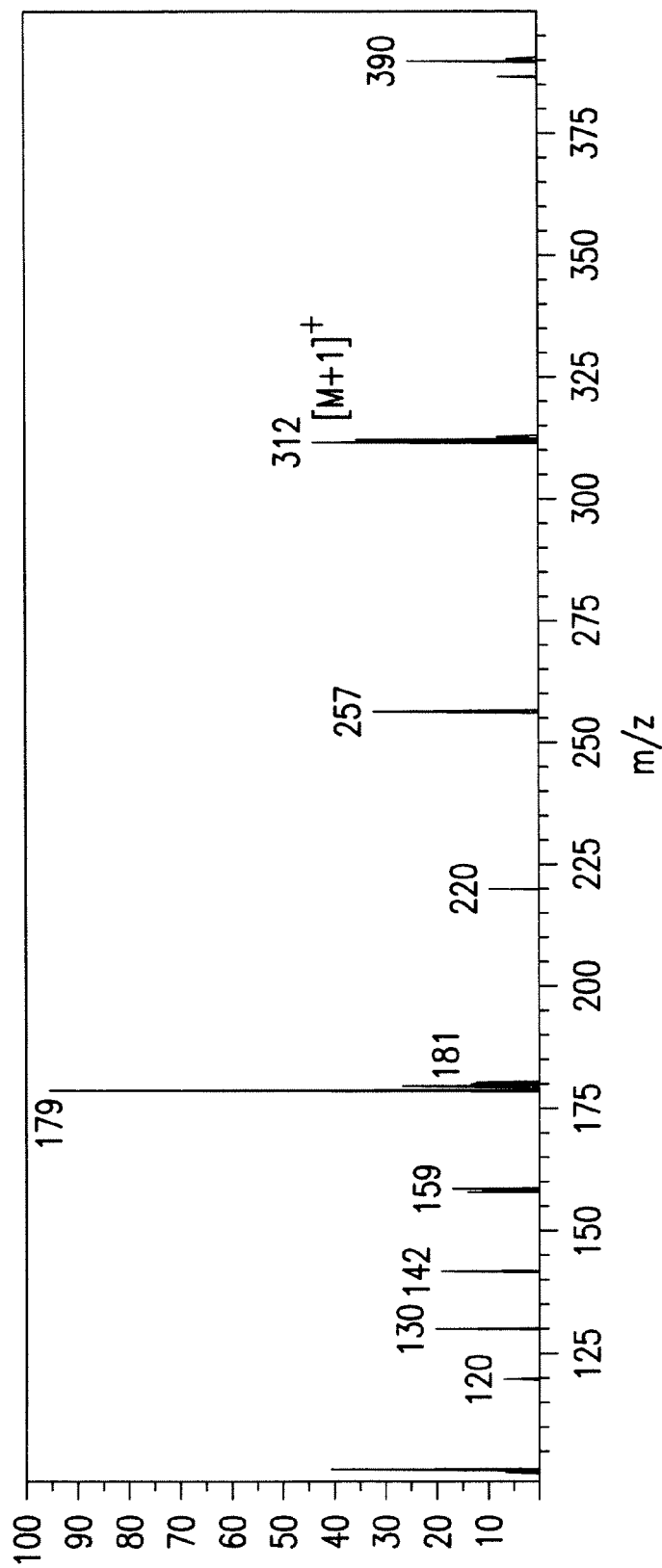
FIG. 6 represents an MS spectrum of 2-(4-nitrophenyl)imidazo[2,1-b]benzothiazol-7-ol (V).
Figure 7:
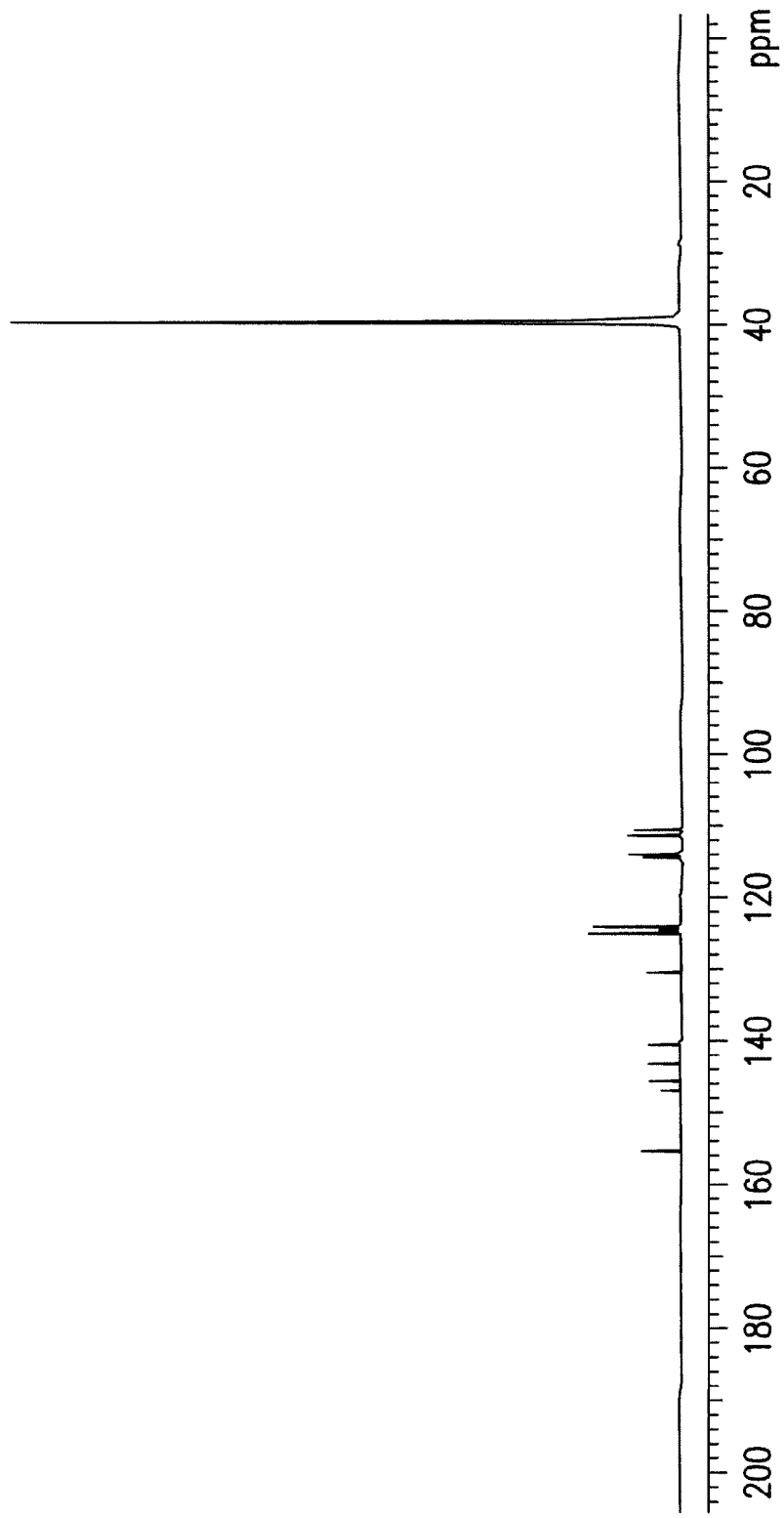
FIG. 7 represents a $^{13}$C NMR spectrum of 2-(4-nitrophenyl)imidazo[2,1-b]benzothiazol-7-ol (V) in DMSO-$d_6$.
Figure 8:
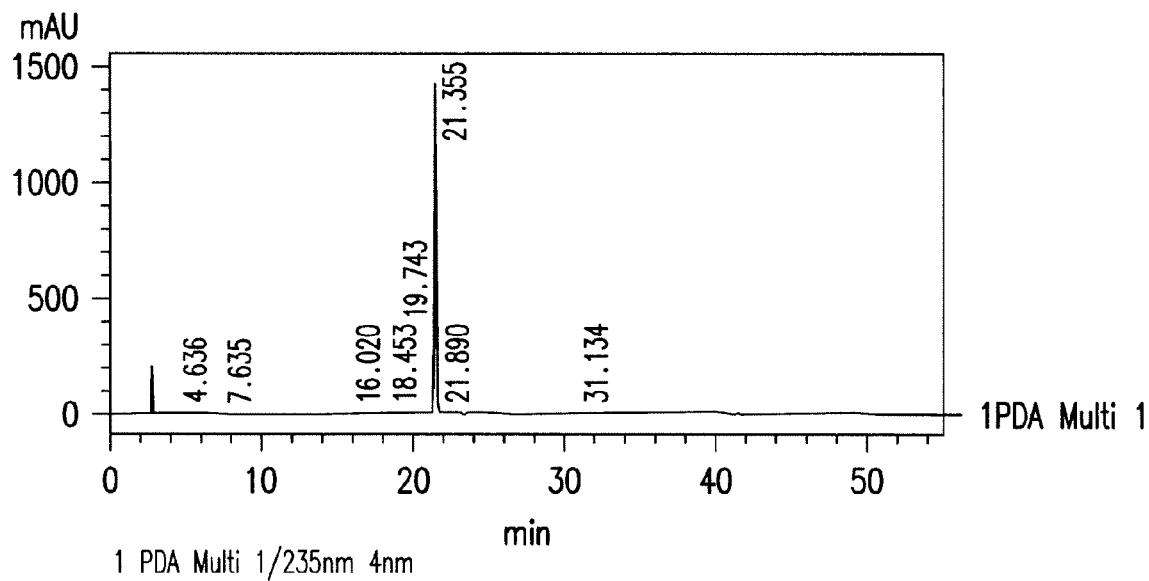
FIG. 8 represents an HPLC chromatogram of 2-(4-nitrophenyl)imidazo[2,1-b]benzothiazol-7-ol (V).
Figure 9:
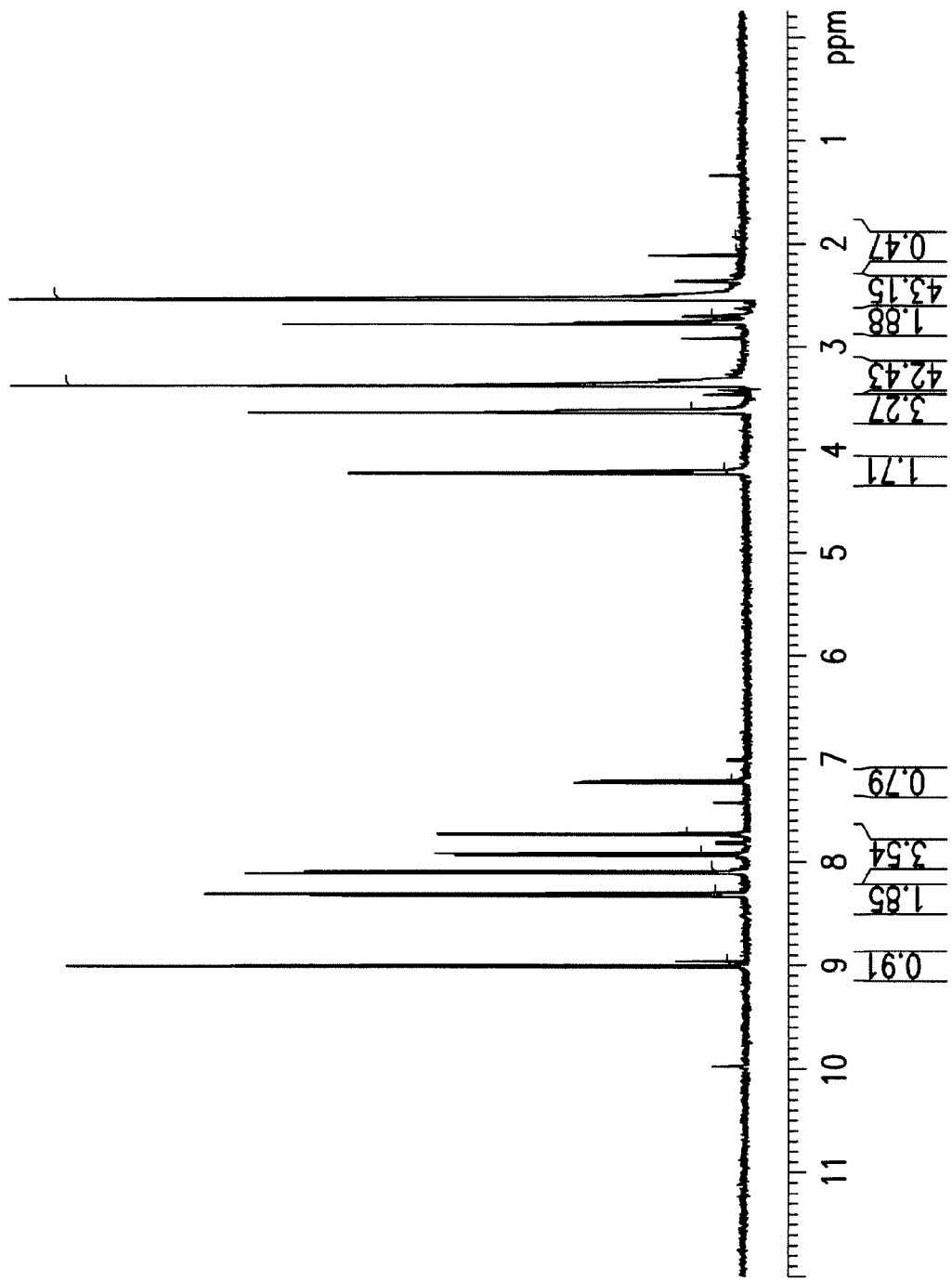
FIG. 9 represents a $^1$H NMR spectrum of 7-(2-morpholin-4-yl-ethoxy)-2-(4-nitrophenyl)imidazo[2,1-b]benzothiazole (VII) in DMSO-$d_6$.
Figure 11:
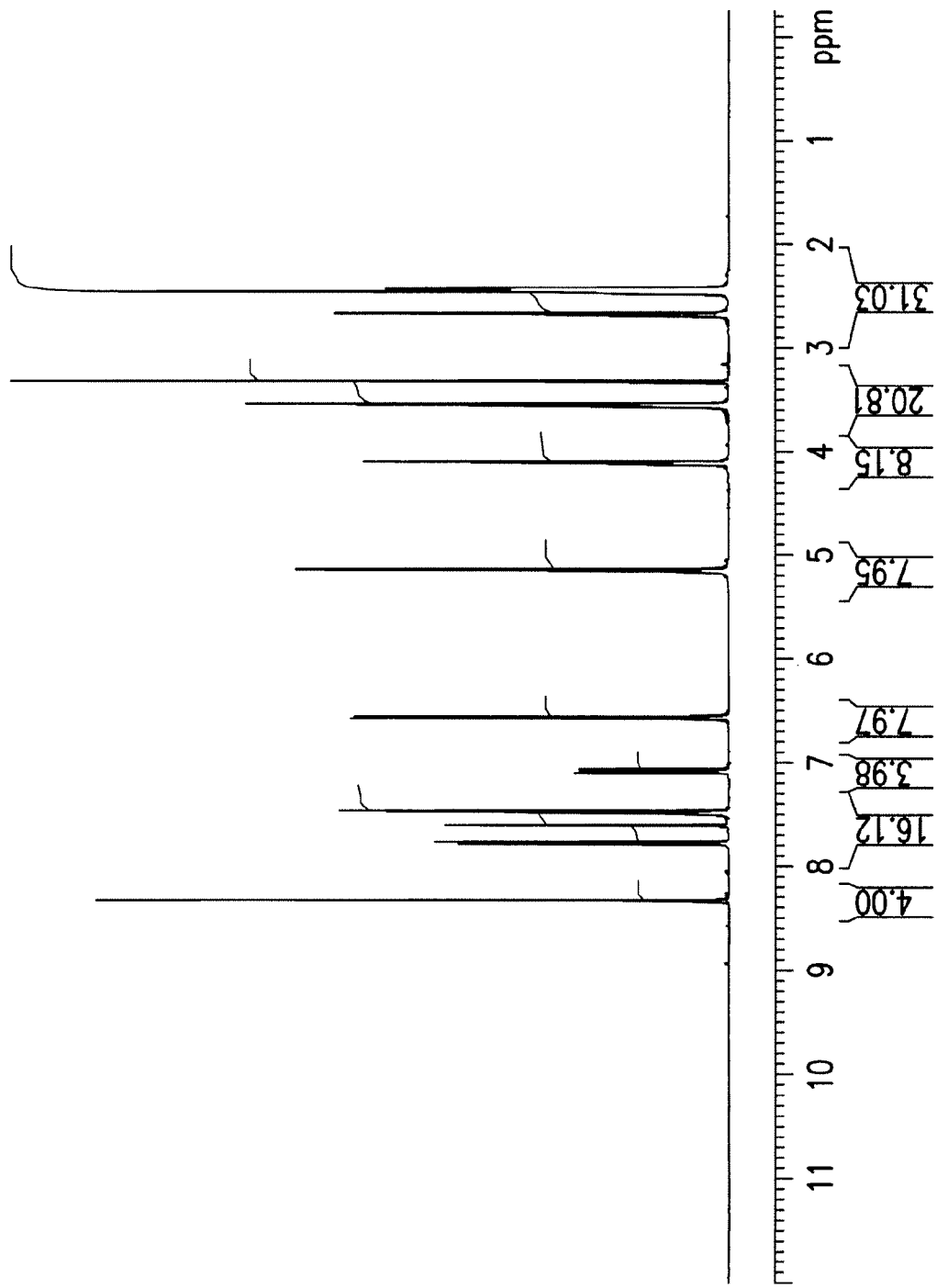
FIG. 11 represents a $^1$H NMR spectrum of 7-(2-morpholin-4-yl-ethoxy)-2-(4-aminophenyl)imidazo[2,1-b]benzothiazole (VIII) in DMSO-$d_6$.
Figure 12:
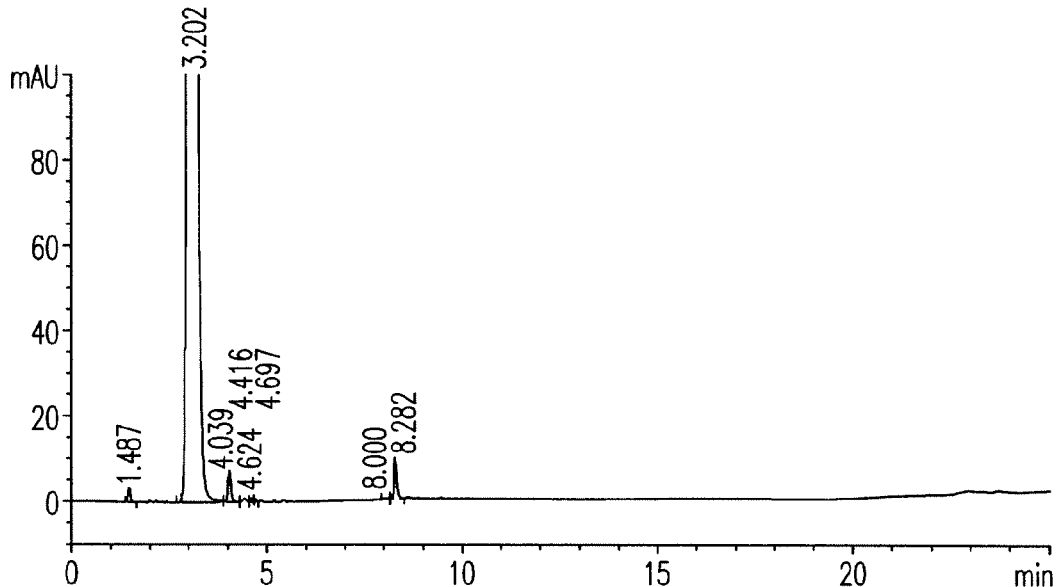
FIG. 12 represents an HPLC chromatogram of 7-(2-morpholin-4-yl-ethoxy)-2-(4-aminophenyl)imidazo[2,1-b]benzothiazole (VIII).
Figure 13:
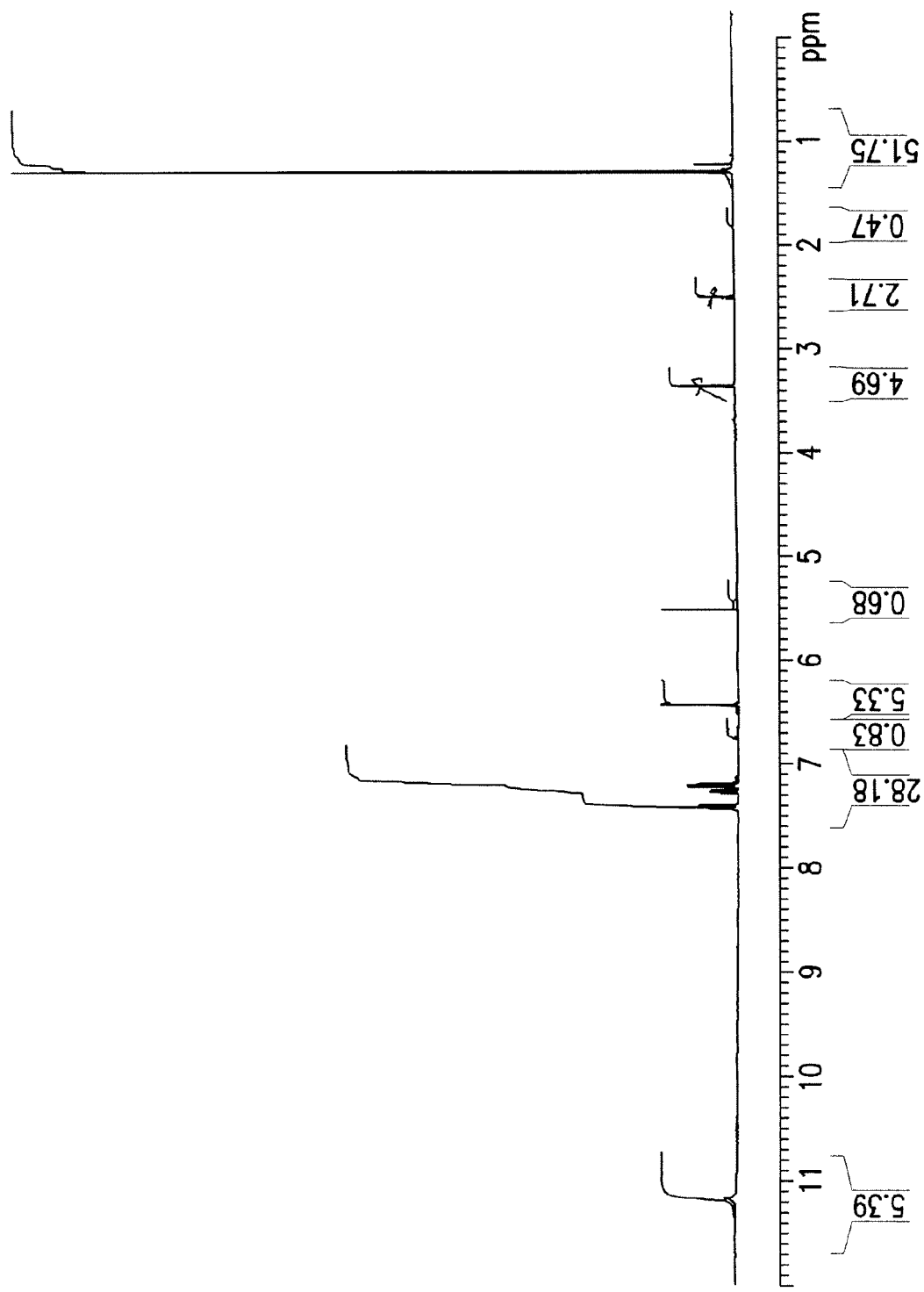
FIG. 13 represents a $^1$H NMR spectrum of phenyl 5-tert-butylisoxazol-3-ylcarbamate (X) in DMSO-$d_6$.
Figure 14:
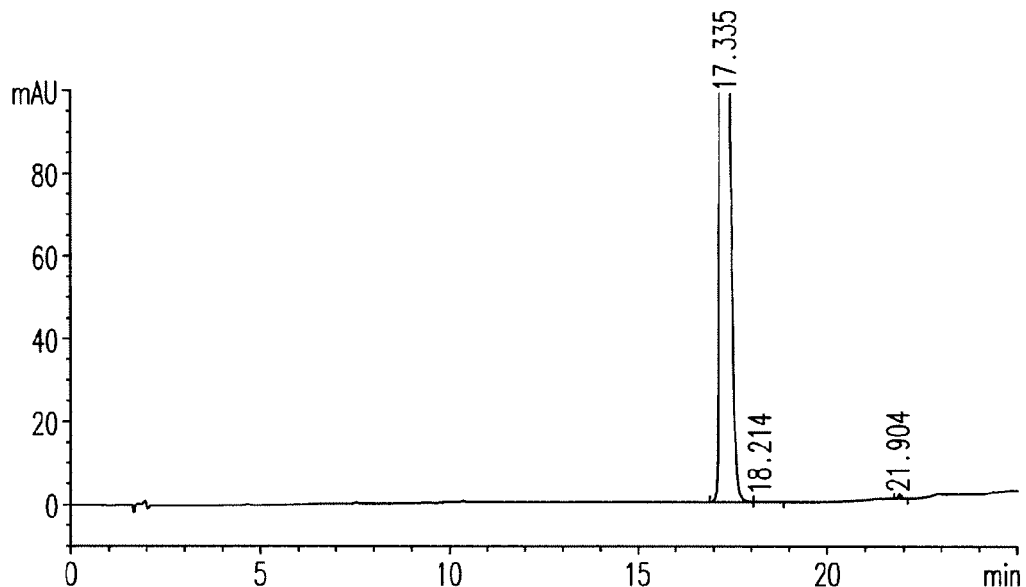
FIG. 14 represents an HPLC chromatogram of phenyl 5-tert-butylisoxazol-3-ylcarbamate (X).
Figure 15:
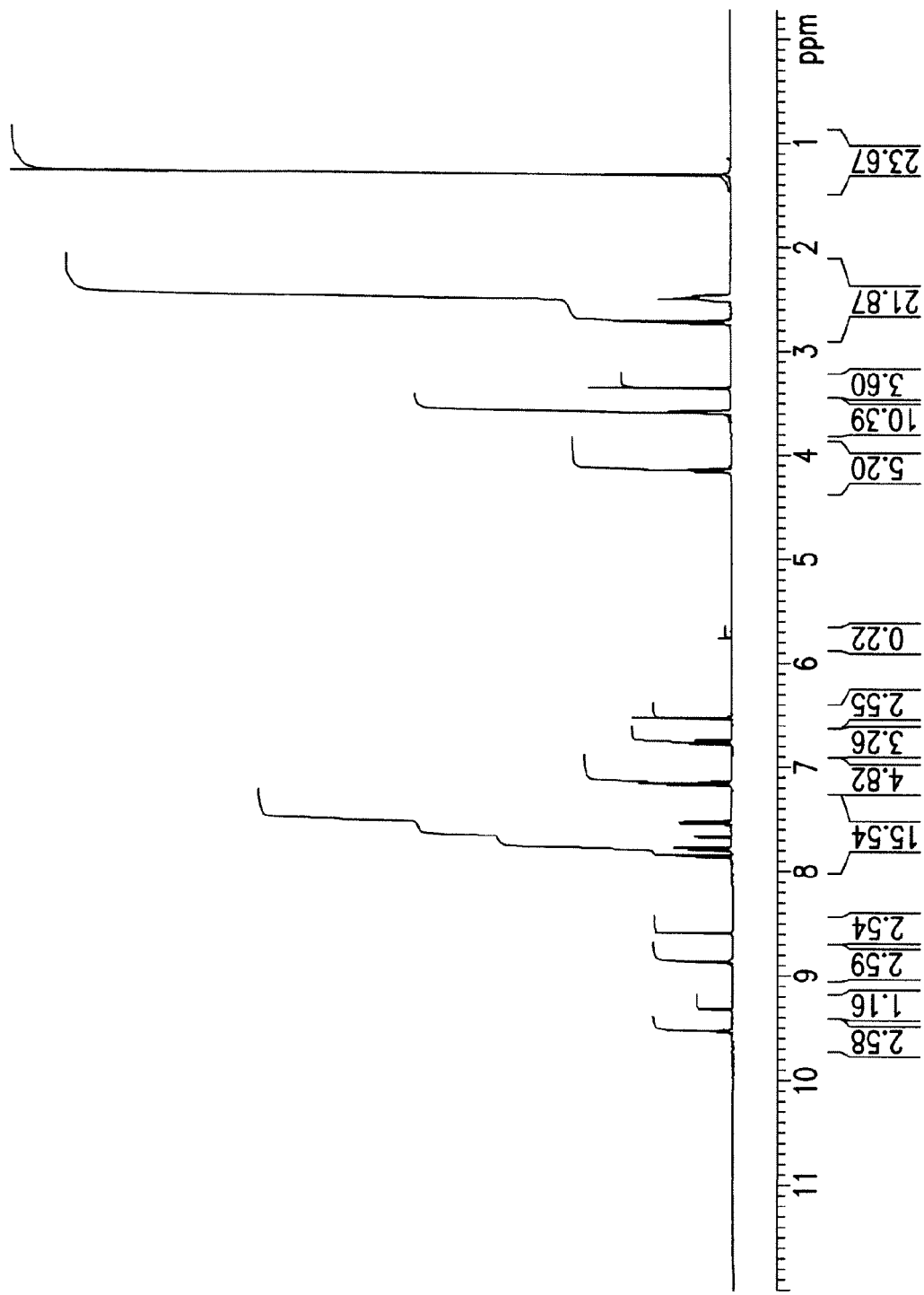
FIG. 15 represents a $^1$H NMR spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea (I) in DMSO-$d_6$ prepared using the processes described herein.
Figure 16:
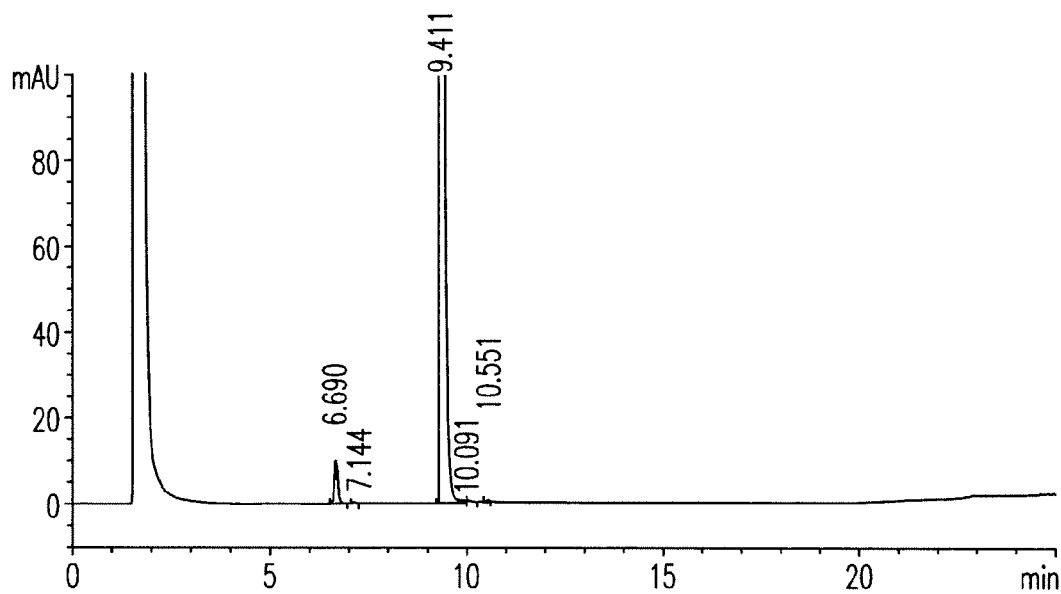
FIG. 16 represents an HPLC chromatogram of N-(5-tert-butyl-isoxazol-3-yl)-N'-{4-[7-(2-morpholin-4-yl-ethoxy)imidazo[2,1-b][1,3]benzothiazol-2-yl]phenyl}urea (I) prepared using the processes described herein.

Unless defined otherwise, all technical and scientific terms used herein have the same meaning as those commonly understood by one of ordinary skill in the art. Abbreviations are as defined in *J. Org. Chem.* 2007, 72, 23A. All publications and patents referred to herein are incorporated by reference herein in their entireties.

A. Definitions

As used herein, and unless otherwise indicated, the term "process" refers to the methods disclosed herein which are useful for preparing a compound provided herein. Modifications to the methods disclosed herein (e.g., starting materials, reagents, protecting groups, solvents, temperatures, reaction times, purification) that are well known to those of ordinary skill in the art are also encompassed by the present disclosure.

As used herein, and unless otherwise indicated, the term "adding," "reacting," "mixing," or the like means contacting one reactant, reagent, solvent, catalyst, reactive group, or the like with another reactant, reagent, solvent, catalyst, reactive group, or the like. Unless otherwise specified, reactants, reagents, solvents, catalysts, reactive group, or the like can be added individually, simultaneously, or separately, or can be added in any order. They can be added in the presence or absence of heat, and can optionally be added under an inert atmosphere. "Reacting" can refer to in situ formation or intramolecular reaction where the reactive groups are in the same molecule.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise indicated, a reaction that is "substantially complete" or is driven to "substantial completion" means that the reaction contains more than about 50% by percent yield, more than about 60% by percent yield, more than about 70% by percent yield, more than about 80% by percent yield, more than about 90% by percent yield, more than about 95% by percent yield, or more than about 97% by percent yield of the desired product. Alternatively, the terms "substantially complete" or "substantial completion" means that the reaction contains less than about 50% of a starting material relative to its starting amount, less than about 40%, less than about 30%, less than about 20%, less than about 10%, less than about 5%, less than about 3%, less than about 1%, less than about 0.5%, less than about 0.1%, less than about 0.05%, or less than about 0.01% of a starting material relative to its starting amount.

As used herein, and unless otherwise specified, a composition that is "substantially free" of a compound means that the composition contains less than about 20% by weight, less than about 10% by weight, less than about 5% by weight, less than about 3% by weight, less than about 1% by weight, less than about 0.1% by weight, less than about 0.01% by weight, less than about 0.001% by weight, or less than about 0.0001% by weight of the compound.

As used herein, and unless otherwise specified, a composition that is "substantially pure" means that the composition has a purity level of greater than about 80% by weight, greater than about 90% by weight, greater than about 95% by weight, greater than about 97% by weight, greater than about 99% by weight, greater than about 99.5% by weight, greater than about 99.9% by weight, greater than about 99.95% by weight, greater than about 99.99% by weight, greater than about 99.995% by weight, greater than about 99.999% by weight, greater than about 99.9995% by weight, or greater than about 99.9999% by weight.

As used herein, and unless otherwise specified, a composition that is "substantially chemically pure" means that the composition has a chemical purity level of greater than about 80% by weight, greater than about 90% by weight, greater than about 95% by weight, greater than about 97% by weight, greater than about 99% by weight, greater than about 99.5% by weight, greater than about 99.9% by weight, greater than about 99.95% by weight, greater than about 99.99% by weight, greater than about 99.995% by weight, greater than about 99.999% by weight, greater than about 99.9995% by weight, or greater than about 99.9999% by weight. In other words, the composition is substantially free of one or more chemical impurities.

As used herein, and unless otherwise specified, a composition that is "substantially physically pure" means that the composition has a physical purity level, such as, e.g., a crystal form purity level, of greater than about 80% by weight, greater than about 90% by weight, greater than about 95% by weight, greater than about 97% by weight, greater than about 99% by weight, greater than about 99.5% by weight, greater than about 99.9% by weight, greater than about 99.95% by weight, greater than about 99.99% by weight, greater than about 99.995% by weight, greater than about 99.999% by weight, greater than about 99.9995% by weight, or greater than about 99.9999% by weight. In other words, the composition is substantially free of one or more physical impurities, such as, e.g., polymorphs or crystal forms.

As used herein, and unless otherwise specified, the term "organic group" refers to a group containing at least one carbon atom. Examples of the organic group include, but are not limited to, alkyl, alkenyl, alkynyl, carboxyl, acyl, cycloalkyl, aryl, heteroaryl, heteroalkyl, and heterocycloalkyl.

As used herein, and unless otherwise specified, the term "leaving group" refers to a stable moiety that can be detached from a molecule in a bond-breaking step. In one embodiment, the leaving group includes, but is not limited to, fluoro, chloro, bromo, iodo, methanesulfonate, ethanesulfonate, trifluoromethanesulfonate, benzenesulfonate, 4-methylbenzenesulfonate, and bromobenzenesulfonate.

Unless otherwise specified, the compounds described herein, including intermediates useful for the preparation of the compounds, which contain reactive functional groups (such as, without limitation, carboxy, hydroxy, and amino moieties), also encompass suitable protected derivatives thereof. "Protected derivatives" are those compounds in which a reactive site or sites are blocked with one or more protecting groups (also known as blocking groups). Suitable protecting groups for carboxy moieties include benzyl, t-butyl, and the like. Suitable protecting groups for amino and amido groups include acetyl, t-butyloxycarbonyl, benzyloxycarbonyl, silyl, and the like. Suitable protecting groups for hydroxy include methyl, benzyl, acetyl, silyl, and the like. Other suitable protecting groups are well known to those of ordinary skill in the art. The choice and use of protecting groups and the reaction conditions to install and remove protecting groups are described, for example, in Greene & Wuts, "Protective Groups in Organic Synthesis", 4th Edition, Wiley Interscience, 2006; Kocienski, "Protecting Groups," 3rd Edition, Thieme, 2005.

As used herein, and unless otherwise specified, the term "hydrogen" encompasses proton ($^1$H), deuterium ($^2$H), tritium ($^3$H), and/or mixtures thereof.

As used herein, and unless otherwise specified, the term "halo," "halogen," or "halide" refers to fluorine, chlorine, bromine, and/or iodine.

As used herein, and unless otherwise specified, the term "methylene" refers to a divalent —CH$_2$— group.

As used herein, and unless otherwise specified, the term "carbonyl" refers to a divalent —C(=O)— group.

As used herein, and unless otherwise specified, the term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, i-propyl, butyl (including all isomeric forms), n-butyl, i-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl(tetralinyl). In certain embodiments, aryl may also be optionally substituted with one or more substituents.

As used herein, and unless otherwise specified, the term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl groups may be optionally substituted with one or more substituents.

As used herein, and unless otherwise specified, the term "heteroalkyl" or "heteroalkyl group" refers to a univalent group derived from an alkyl group, where at least one methylene group is replaced by a heteroatom or a hetero-group such as O, S, or NR, where R is H or an organic group.

As used herein, and unless otherwise specified, the term "alkoxy" or "alkoxy group" refers to an alkyl group that is linked to another group via an oxygen atom (i.e., —O—alkyl). An alkoxy group can be unsubstituted or substituted with one or more suitable substituents. Examples of alkoxy groups include, but are not limited to, $(C_1-C_6)$alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, —O—3-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl, and —O-hexyl. An alkoxy group can be unsubstituted or substituted with one or two suitable substituents. In some embodiments, the alkyl chain of an alkyloxy group is straight or branched, and has from 1 to 8 carbon atoms, referred to herein as "$(C_1-C_8)$alkoxy".

As used herein, and unless otherwise specified, the term "aryloxy" or "aryloxy group" refers to an O-aryl group, wherein aryl is as defined herein elsewhere. An aryloxy group can be unsubstituted or substituted with one or two suitable substituents. In some embodiments, the aryl ring of an aryloxy group is a monocyclic ring, wherein the ring comprises 6 carbon atoms, referred to herein as "$(C_6)$aryloxy."

As used herein, and unless otherwise specified, the term "alkoxycarbonyl" or "alkoxycarbonyl group" refers to a monovalent group of the formula —C(=O)-alkoxy. In some embodiments, the hydrocarbon chain of an alkoxycarbonyl group is straight or branched, and has from 1 to 8 carbon atoms, referred to herein as a "lower alkoxycarbonyl" group.

As used herein, and unless otherwise specified, the term "acyloxy" or "acyloxy group" refers to a monovalent group of the formula —O—C(=O)-alkyl or —O—C(=O)— aryl, wherein alkyl and aryl are as defined herein elsewhere.

As used herein, and unless otherwise specified, the term "acyl" or "acyl group" refers to a monovalent group of the formula —C(=O)H, —C(=O)-alkyl, or —C(=O)— aryl, wherein alkyl and aryl are as defined herein elsewhere.

As used herein, and unless otherwise specified, the term "alkenyl" refers to a linear or branched monovalent hydrocarbon radical, which contains one or more (in specific embodiments, one to five) carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more (in specific embodiments, one to five) carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the term "cycloalkyl" refers to a cyclic saturated bridged and/or non-bridged monovalent hydrocarbon radical, which may be optionally substituted one or more substituents as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

As used herein, and unless otherwise specified, the term "arylalkyl" or "aralkyl" refers to a monovalent alkyl group substituted with aryl. In certain embodiments, both alkyl and aryl may be optionally substituted with one or more substituents.

As used herein, and unless otherwise specified, the term "heterocycloalkyl," "heterocyclyl," or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may be optionally substituted with one or more substituents.

As used herein, and unless otherwise specified, the term "optionally substituted" is intended to mean that a group, such as an alkyl, alkenyl, alkynyl, cycloalkyl, aryl, aralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more (in specific embodiments, one, two, three, or four) substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more (in specific embodiments, one, two, three, or four) substituents $Q^1$; or (iii) R$^b$ and R$^c$ together with the N atom to which they are attached form heteroaryl or heterocyclyl, optionally substituted with one or more (in specific embodiments, one, two, three, or four) substituents $Q^1$. As used herein, all groups that can be substituted are "optionally substituted," unless otherwise specified.

In specific embodiments, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

When a compound provided herein contains one or more acidic or basic moieties, the compound may exist as a salt. As used herein, and unless otherwise specified, the term "salt" or "salts" of a compound refers to salt(s) of a compound having basic or acidic groups, and the salts are prepared from the compound and one or more acids, including inorganic acids and organic acids; or one or more bases, including inorganic bases and organic bases. In certain embodiments, the compounds provided herein are basic in nature and are capable of forming salts with various inorganic or organic acids. The acids that may be used to prepare salts of such basic compounds are described herein elsewhere. In certain embodiments, the compounds provided herein are acidic in nature and are capable of forming salts with various inorganic or organic bases. Non-limiting examples of such salts with inorganic bases include alkali metal or alkaline earth metal salts. In certain embodiments, the salt of a compound provided herein comprises one or more acidic or basic counter-ions, including, but not limited to: acetate, ascorbate, benzenesulfonate, benzoate, bicarbonate, bitartrate, bromide, calcium edetate, camsylate, carbonate, chloride, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, malonate, mandelate, mesylate, methanesulfonate, muscate, napsylate, nitrate, oxalate, pantothenate, phosphate, diphosphate, polygalacturonate, salicylate, stearate, succinate, sulfate, bisulfate, sulfite, tannate, tartrate, teoclate, triethiodide, and/or pamoate, and the like; or lithium, sodium, potassium, magnesium, calcium, zinc, iron, and/or ammonium ions, and the like; or N,N-dicyclohexylmethyl amine, diisopropylamine, diisopropylethyl amine, ethanolamine, 2,6-lutidine, N-methylmorpholine, pyridine, and/or triethylamine, and the like; or amino acids, and/or protected amino acids, and the like.

When a compound provided herein contains an acidic or basic moiety, it may also be provided as a pharmaceutically acceptable salt (see, e.g., "Handbook of Pharmaceutical Salts, Properties, and Use," Stahl and Wermuth, Ed.; Wiley-VCH and VHCA, Zurich, 2002). As used herein, and unless otherwise specified, the term "pharmaceutically acceptable salts" refers to salts prepared from pharmaceutically acceptable non-toxic acids, including inorganic acids and organic acids, or pharmaceutically acceptable non-toxic bases, including inorganic bases and organic bases. In one embodiment, suitable acids for use in the preparation of pharmaceutically acceptable salt include, but are not limited to, acetic, adipic, L-ascorbic, L-aspartic, capric, carbonic, citric, fumaric, galactaric, D-glucoheptanoic, D-gluconic, D-glucuronic, glutamic, glutaric, glycerophosphoric, hippuric, hydrochloric, DL-lactic, lauric, maleic, (−)-L-malic, phosphoric, sebacic, succinic, sulphuric, (+)-L-tartaric, and thiocyanic. In one embodiment, suitable acids for use in the preparation of pharmaceutically acceptable salt include, but are not limited to, alginic, benzenesulfonic, benzoic, (+)-camphoric, caprylic, cyclamic, dodecylsulfuric, ethane-1,2-disulfonic, methanesulfonic, ethanesulfonic, 2-hydroxy-, gentisic, 2-oxo glutaric, isobutyric, lactobionic, malonic, methanesulfonic, naphthalene-1,5-disulfonic, naphthalene-2-sulfonic, 2-napthoic 1-hydroxy, nicotinic, oleic, orotic, oxalic, pamoic, propionic, (−)-L-pyroglutamic and p-toluenesulfonic acids.

In one embodiment, suitable acids for use in the preparation of salts include, but are not limited to, acetic, 2,2-dichloroacetic, acylated amino, adipic, alginic, anthranilic, ascorbic, aspartic, L-aspartic, D-aspartic, benzenesulfonic, benzoic, 4-acetamidobenzoic, boric, camphoric, (+)-camphoric, (−)-camphoric, camphorsulfonic, (1R)-(−)-10-camphorsulfonic, (1S)-(+)-10-camphorsulfonic, capric, caproic, caprylic, cinnamic, citric, cyclamic, cyclohexanesulfamic, dodecylsulfuric, ethane-1,2-disulfonic, ethenesulfonic, 2-hydroxy-ethanesulfonic, formic, fumaric, furoic, galactaric, galacturonic, gentistic, glucarenic, glucoheptonic, gluconic, D-gluconic, L-gluconic, glucuronic, D-glucuronic, L-glucuronic, glutamic, D-glutamic, L-glutamic, glutaric, oxoglutaric, α-oxoglutaric, β-oxoglutaric, glycolic, glycidic, hippuric, hydrobromic, hydrochloric, hydroiodic, isethionic, lactic, D-lactic, L-lactic, lactobionic, lauric, maleic, malic, D-malic, L-malic, malonic, mandelic, (+)-mandelic, (−)-mandelic, methanesulfonic, mucic, naphthalene-2-sulfonic, naphthalene-1,5-disulfonic, 1-hydroxy-2-naphthoic, nicotinic, nitric, oleic, orotic, oxalic, palmitic, pamoic, pantothenic, perchloric, phenylacetic, phosphoric, propionic, pyroglutamic, L-pyroglutamic, D-pyroglutamic, saccharic, salicylic, 4-aminosalicylic, sebacic, stearic, succinic, sulfanilic, sulfuric, tannic, tartaric, DL-tartaric, D-tartaric, L-tartaric, thiocyanic, p-toluenesulfonic, trifluoroacetic, trifluoromethanesulfonic, undecylenic, and valeric acid.

In one embodiment, suitable bases for use in the preparation of salts including, but not limited to, inorganic bases, such as magnesium hydroxide, calcium hydroxide, potassium hydroxide, zinc hydroxide, lithium hydroxide, or sodium hydroxide; and organic bases, such as primary, secondary, tertiary, and quaternary, aliphatic and aromatic amines, including L-arginine, benethamine, benzathine, choline, deanol, N,N-dicyclohexylmethyl amine, diethanolamine, diethylamine, dimethylamine, dipropylamine, diisopropylamine, diisopropylethyl amine, 2-(diethylamino)-ethanol, ethanolamine, ethylamine, ethylenediamine, isopropylamine, N-methyl-glucamine, hydrabamine, 1H-imidazole, L-lysine, 2,6-lutidine, morpholine, N-methyl-morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, "salt," "salts" or "pharmaceutically acceptable salt" of Compound (I) refers to acid addition salt(s) of Compound (I), derived from inorganic acids and/or organic acids, as described herein elsewhere. In one embodiment, the salt is formed from hydrochloric acid. In one embodiment, the salt is a dihydrochloride salt. In one embodiment, the salt is formed from hydrochloric, hydrobromic, boric, phosphoric, or sulfuric acid. In one embodiment, the salt is formed from acetic, citric, fumaric, maleic, malic, malonic, oxalic, succinic, tartaric, p-toluenesulfonic, methanesulfonic, ethanesulfonic, trifluoromethanesulfonic, benzenesulfonic, bromobenzenesulfonic, or trifluoroacetic acid.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate (e.g., mono-hydrate, dihydrate, trihydrate, tetrahydrate, and the like).

As used herein, and unless otherwise indicated, the term "polymorph" refers to a solid crystalline form of a compound provided herein or a salt or complex thereof. Different polymorphs of the same compound can exhibit different physical, chemical, biological, and/or spectroscopic properties, among others.

It should be noted that where structural isomers are interconvertible, the compound provided herein may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

As used herein, and unless otherwise specified, the terms "drug" and "therapeutic agent" refer to a compound, or a pharmaceutical composition thereof, which is administered to a subject for treating, preventing, managing, and/or ameliorating one or more symptoms of a condition, disorder, or disease.

As used herein, and unless otherwise specified, the terms "active ingredient," "active substance," or "active pharmaceutical ingredient" refers to a compound or a substance, which is administered, alone or in combination with other pharmaceutically active compound(s), and/or one or more pharmaceutically acceptable excipients, to a subject for treating, preventing, and/or ameliorating one or more symptoms of a condition, disorder, or disease. As used herein, "active ingredient," "active substance," and "active pharmaceutical ingredient" may be a pharmaceutically acceptable salt, solvate, hydrate, polymorph, or optically active isomer of a compound described herein.

As used herein, and unless otherwise specified, the term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins (2005); *Handbook of Pharmaceutical Excipients,* 5th Edition, Rowe et al., eds., The Pharmaceutical Press and the American Pharmaceutical Association (2005); and *Handbook of Pharmaceutical Additives,* 3rd Edition, Ash & Ash eds., Gower Publishing Company (2007); *Pharmaceutical Preformulation and Formulation,* 2nd Edition, Gibson ed., CRC Press (2009).

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human.

As used herein, and unless otherwise indicated, the term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

As used herein, and unless otherwise indicated, the term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma, carcinoma, bladder cancer, brain cancer, breast cancer, cervical cancer, colorectal cancer, esophageal cancer, head and neck cancer, gastric cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancies, such as leukemia, acute leukemia, acute myeloblastic leukemia, promyelocytic leukemia, acute lymphoblastic leukemia, and Philadelphia positive leukemia.

As used herein, and unless otherwise indicated, the term "hematologic malignancy" refers to cancer of the bone marrow derived cells including the blood, bone marrow and lymphatic tissue. Examples of hematological malignancies include, for instance, myelodysplasia, lymphomas, leukemias, lymphomas (non-Hodgkin's lymphoma), Hodgkin's disease (also called Hodgkin's lymphoma), and myeloma, such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

As used herein, and unless otherwise indicated, the term "leukemia" refers to malignant neoplasms of the blood-forming tissues either of the lymphoid or myeloid lineage, including, but not limited to, chronic lymphocytic leukemia, chronic myelocytic leukemia, acute lymphoblastic leukemia, acute myeloid leukemia and acute myeloblastic leukemia. The leukemia can be relapsed, refractory, or resistant to conventional therapy.

As used herein, and unless otherwise indicated, the term "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of parts of chromosomes 15 and 17.

As used herein, and unless otherwise indicated, the term "acute lymphocytic leukemia," "acute lymphoblastic leukemia," or "ALL" refers to a malignant disease caused by the abnormal growth and development of early nongranular white blood cell or lymphocytes.

As used herein, and unless otherwise indicated, the term "T-cell leukemia" refers to a disease in which certain cells of the lymphoid system called T lymphocytes or T cells are malignant. T cells are white blood cells that normally can attack virus-infected cells, foreign cells, and cancer cells; and produce substances that regulate the immune response.

As used herein, and unless otherwise indicated, the term "relapsed" refers to a situation where a subject or a mammal, which has had a remission of cancer after therapy has a return of cancer cells.

As used herein, and unless otherwise indicated, the term "refractory or resistant" refers to a circumstance where a subject or a mammal, even after intensive treatment, has residual cancer cells in his body.

As used herein, and unless otherwise indicated, the term "anticancer agent" is meant to include anti-proliferative agents and chemotherapeutic agents, including, but not limited to, antimetabolites (e.g., pyrimidine analogs including but not limited to 5-fluoro uracil, floxuridine, capecitabine, clofarabine; fludarabine, 5-azacytidine; cytosine arabinoside (including but not limited to cytarabine, Ara-C, HDAC (high dose cytarabine)); folic acid analogs including but not limited to methotrexate; antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitibine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, doxorubicin, daunorubicin (including but not limited to, daunomycin, rubidomycin, or cerubidine), and mitoxantrone), topoisomerase inhibitors (e.g., etoposide and camptothecins), purine antagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxins, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monocolonal antibodies (e.g., gemtuzumab ozogamicin, alemtuzumab, rituximab, and yttrium-90-ibritumomab tiuxetan), immunomodulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), other kinase inhibitors (e.g., erlotinib, gefitinib, sunitinib, and sorafenib), hormone agonists or antagonists, partial agonists or partial antagonists, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthemia and cryotherapy, and agents to attenuate any adverse effects (e.g., antiemetics).

As used herein, and unless otherwise indicated, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired. As used herein, the term "drug resistance" is meant to include imatinib-resistance, erlotinib-resistance, sorafenib-resistance, sunitinib-resistance, dasatinib-resistance, and/or nilotinib-resistance.

As used herein, unless otherwise specified "Compound (I)" or "AC220" refers to the following compound:

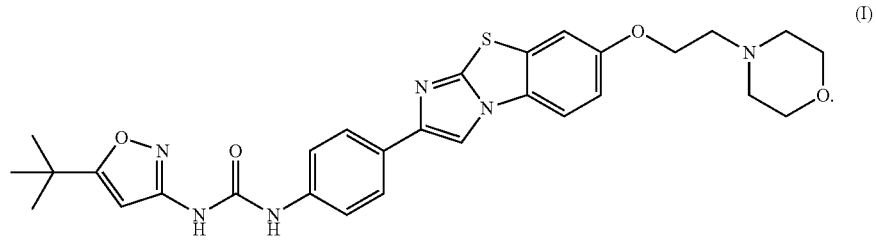 [SMILES: CC(C)(C)c1cc(NC(=O)Nc2ccc(-c3cn4c(n3)sc3cc(OCCN5CCOCC5)ccc34)cc2)no1]

If there is a discrepancy between a depicted structure and a name given that structure, the depicted structure is to be accorded more weight.

B. Processes

Provided herein are processes for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea (I), or a pharmaceutically acceptable salt, solvate, hydrate, or polymorph thereof. In general, the processes provided herein encompasses safe, efficient, cost effective, and/or readily scaleable processes useful for the large scale or commercial production of N-(5-tert-butyl-isoxazol-3-yl)-N'-{4-[7-(2-morpholin-4-yl-ethoxy)imidazo[2,1-b][1,3]benzothiazol-2-yl]phenyl}urea (I), or a pharmaceutically acceptable salt, solvate, hydrate, or polymorph thereof.

In one embodiment, provided herein are processes for the production of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially pure. In one embodiment, provided herein are processes for the production of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially chemically pure. In one embodiment, provided herein are processes for the production of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially physically pure. In one embodiment, provided herein are processes for the production of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is suitable for use in humans, such as for treating, preventing, and/or managing diseases or conditions, including but not limited to, proliferative diseases, FLT-3 mediated diseases, and cancers.

In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, on a scale of greater than 1 gram, greater than 10 gram, greater than 50 gram, greater than 100 gram, greater than 500 gram, greater than 1,000 gram, greater than 5,000 gram, greater than 10,000 gram, greater than 50,000 gram, greater than 100,000 gram, or greater than 500,000 gram.

In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, in an overall yield of greater than about 10%, greater than about 15%, greater than about 20%, greater than about 25%, greater than about 30%, greater than about

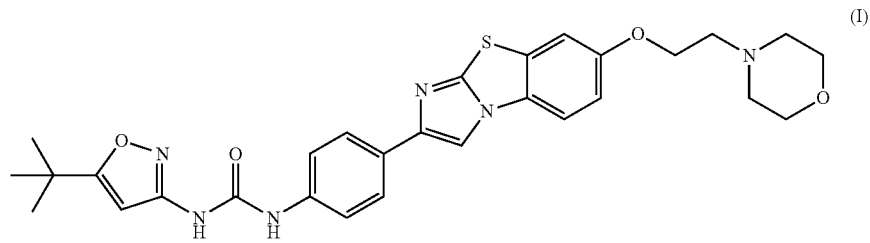 [SMILES: CC(C)(C)c1cc(NC(=O)Nc2ccc(-c3cn4c(n3)sc3cc(OCCN5CCOCC5)ccc34)cc2)no1]

35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95%, wherein the yield is calculated based on starting material, such as, e.g., 3-amino-5-tert-butyl isoxazole (IX), compound (II), compound (IV), or compound (VI), which are described herein elsewhere. In one embodiment, the yield is calculated based on starting material, such as, e.g., 3-amino-5-tert-butyl isoxazole, 2-amino-6-methoxybenzothiazole, 2-bromo-4'-nitroacetophenone, or 4-(2-chloroethyl)morpholine.

In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially pure. In one embodiment, the purity of the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

In one embodiment, the total impurities in the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, produced by a process provided herein, is less than about 5% w/w, less than about 4% w/w, less than about 3% w/w, less than about 2% w/w, less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, or less than about 0.001% w/w relative to the total batch.

In one embodiment, an individual impurity component in the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, produced by a process provided herein, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, less than about 0.01% w/w, less than about 0.005% w/w, less than about 0.001% w/w, less than about 0.0005% w/w, or less than about 0.0001% w/w relative to the total batch.

In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially physically and/or chemically pure. In one embodiment, the processes provided herein produce a polymorph or a crystalline form of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, or hydrate thereof, that is substantially physically pure. In one embodiment, the processes provided herein produce a polymorph or a crystalline form of N-(5-tert-butyl-isoxazol-3-yl)-N'-{4-[7-(2-morpholin-4-yl-ethoxy)imidazo[2,1-b][1,3]benzo-thia-zol-2-yl]phenyl}urea (I), or a pharmaceutically acceptable salt, solvate, or hydrate thereof, that is substantially chemically pure. In one embodiment, the physical purity of the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch. In one embodiment, the chemical purity of the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch.

Figure 18:
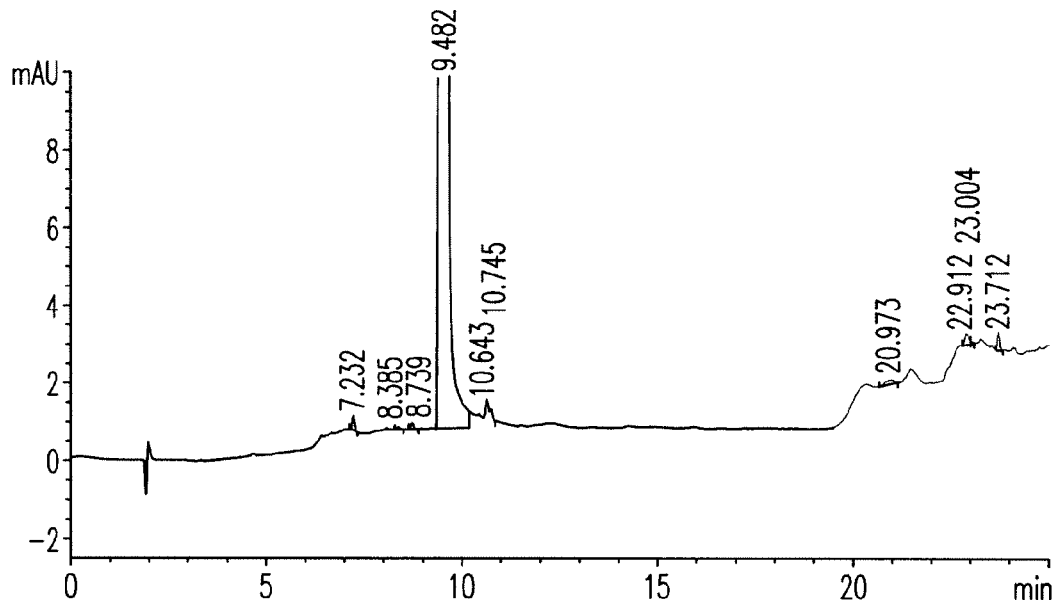
FIG. 18 represents an HPLC chromatogram of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride prepared using the processes described herein.
Figure 19:
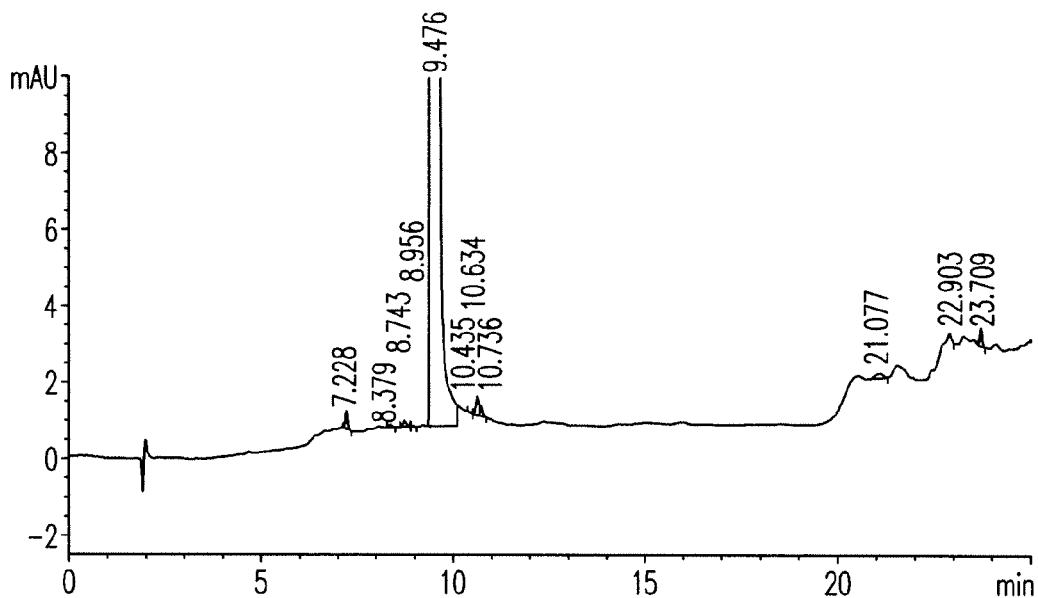
FIG. 19 represents an HPLC chromatogram of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride prepared using the processes described herein.
Figure 20:
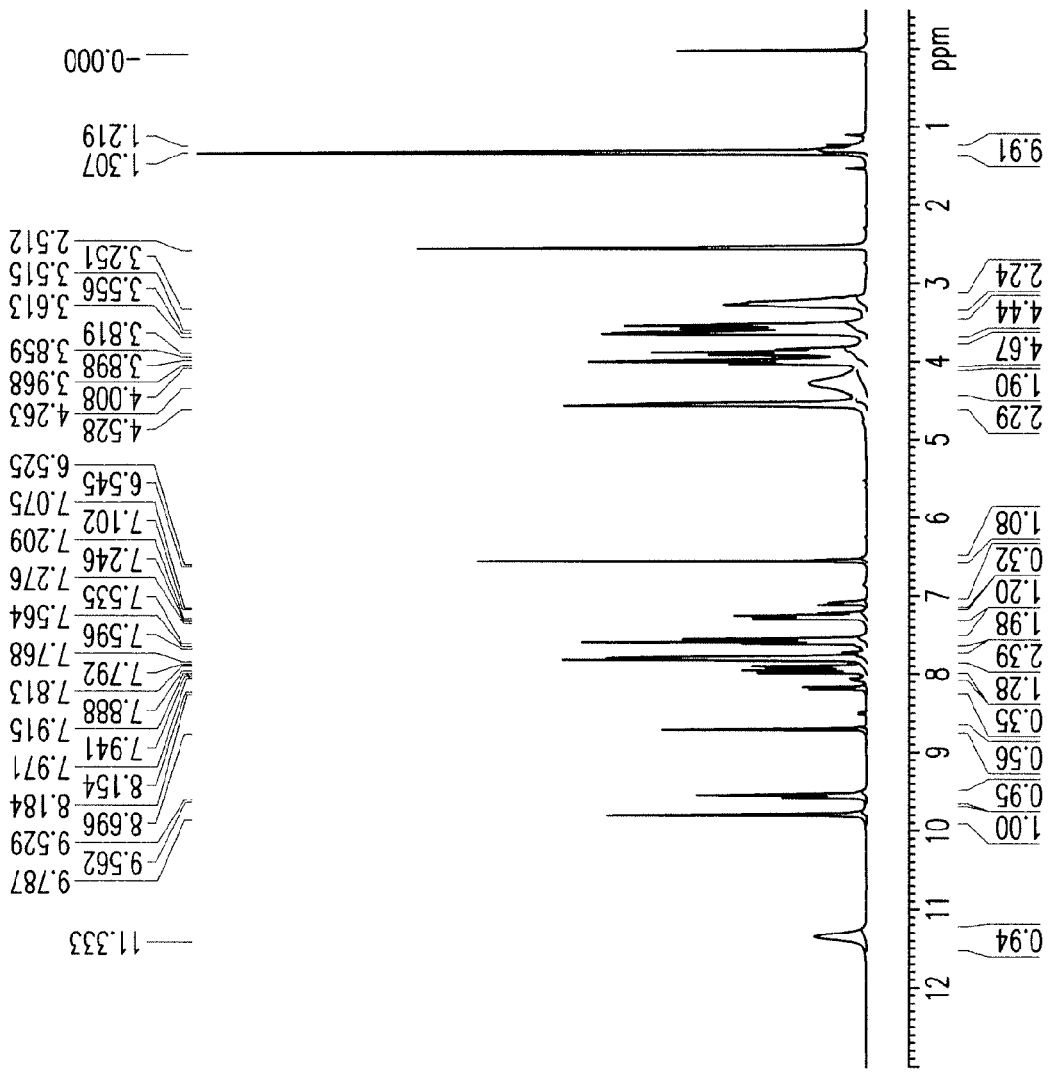
FIG. 20 represents a $^1$H NMR spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride in DMSO-$d_6$ prepared using the processes described herein.
Figure 21:
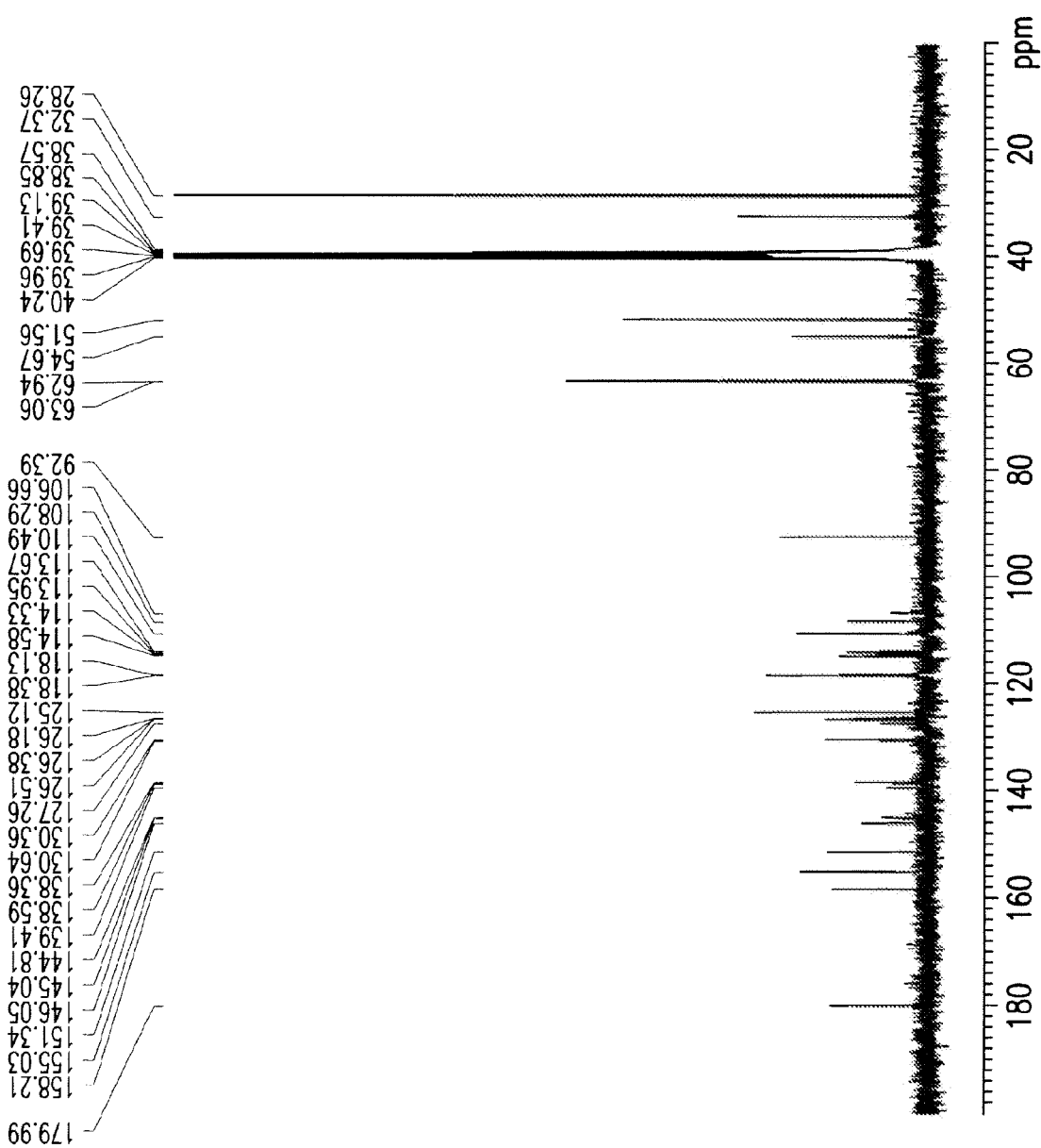
FIG. 21 represents a $^{13}$C NMR spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride in DMSO-$d_6$ prepared using the processes described herein.
Figure 22:
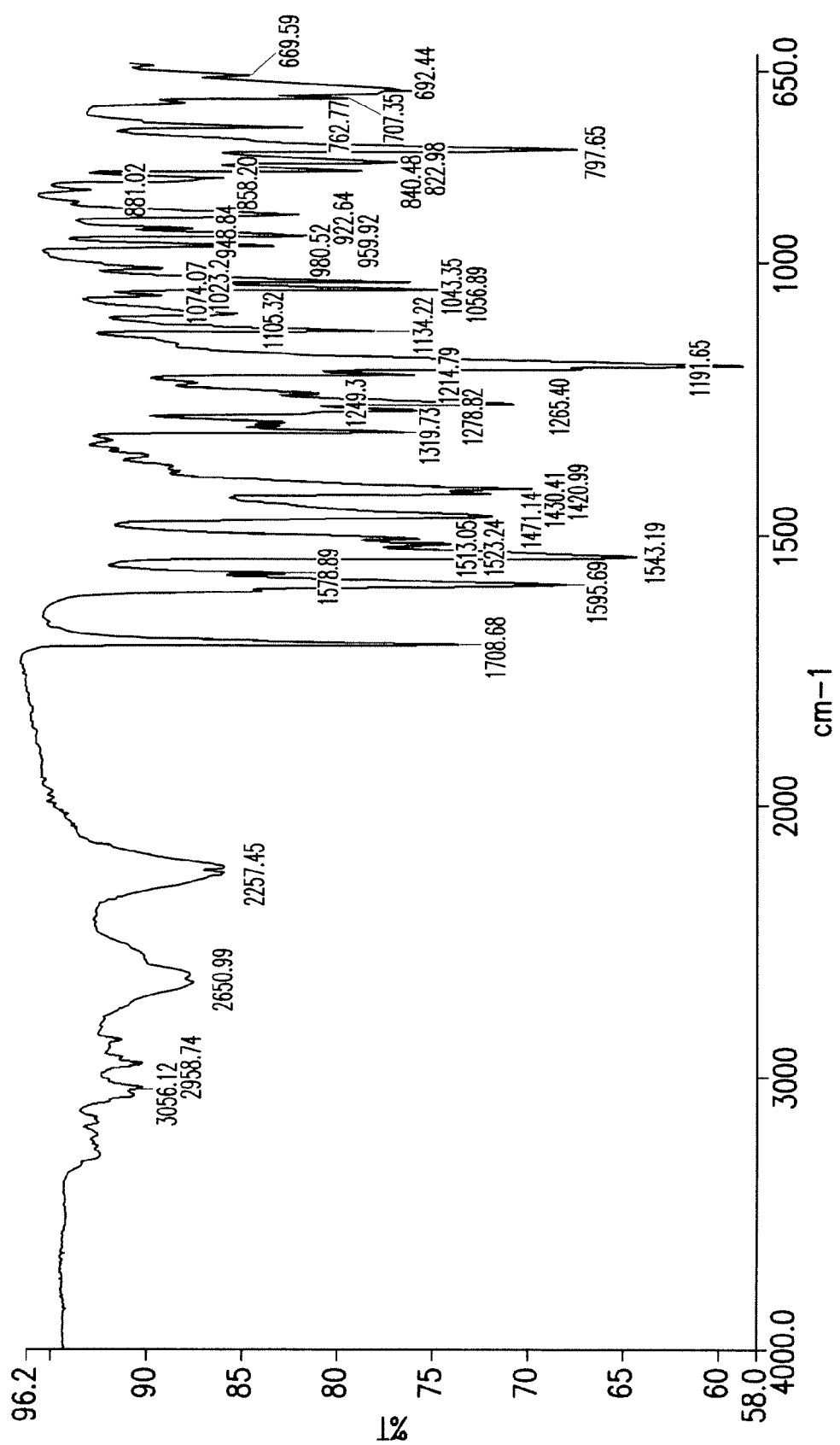
FIG. 22 represents a FTIR spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride in DMSO-$d_6$ prepared using the processes described herein.
Figure 23:
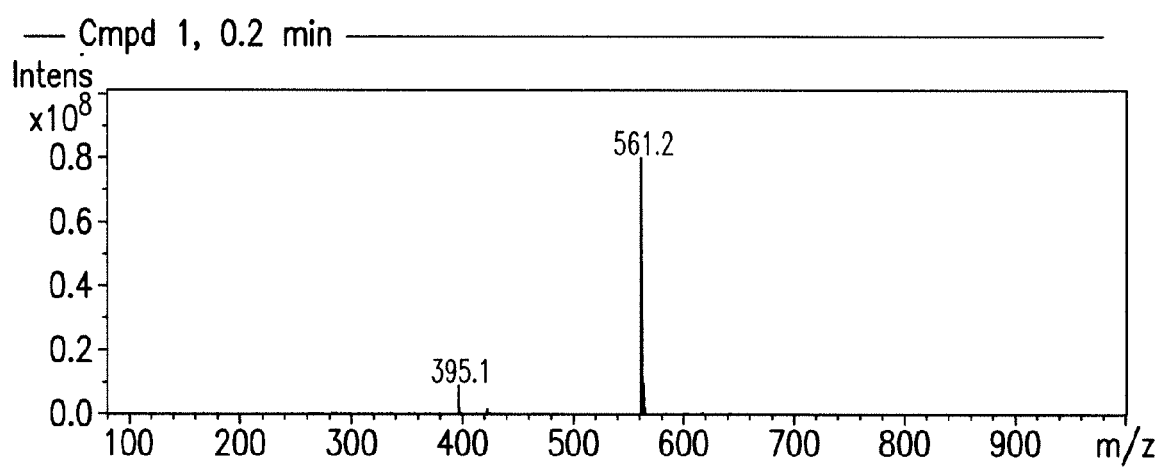
FIG. 23 represents a MS spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride in DMSO-$d_6$ prepared using the processes described herein.
Figure 24:
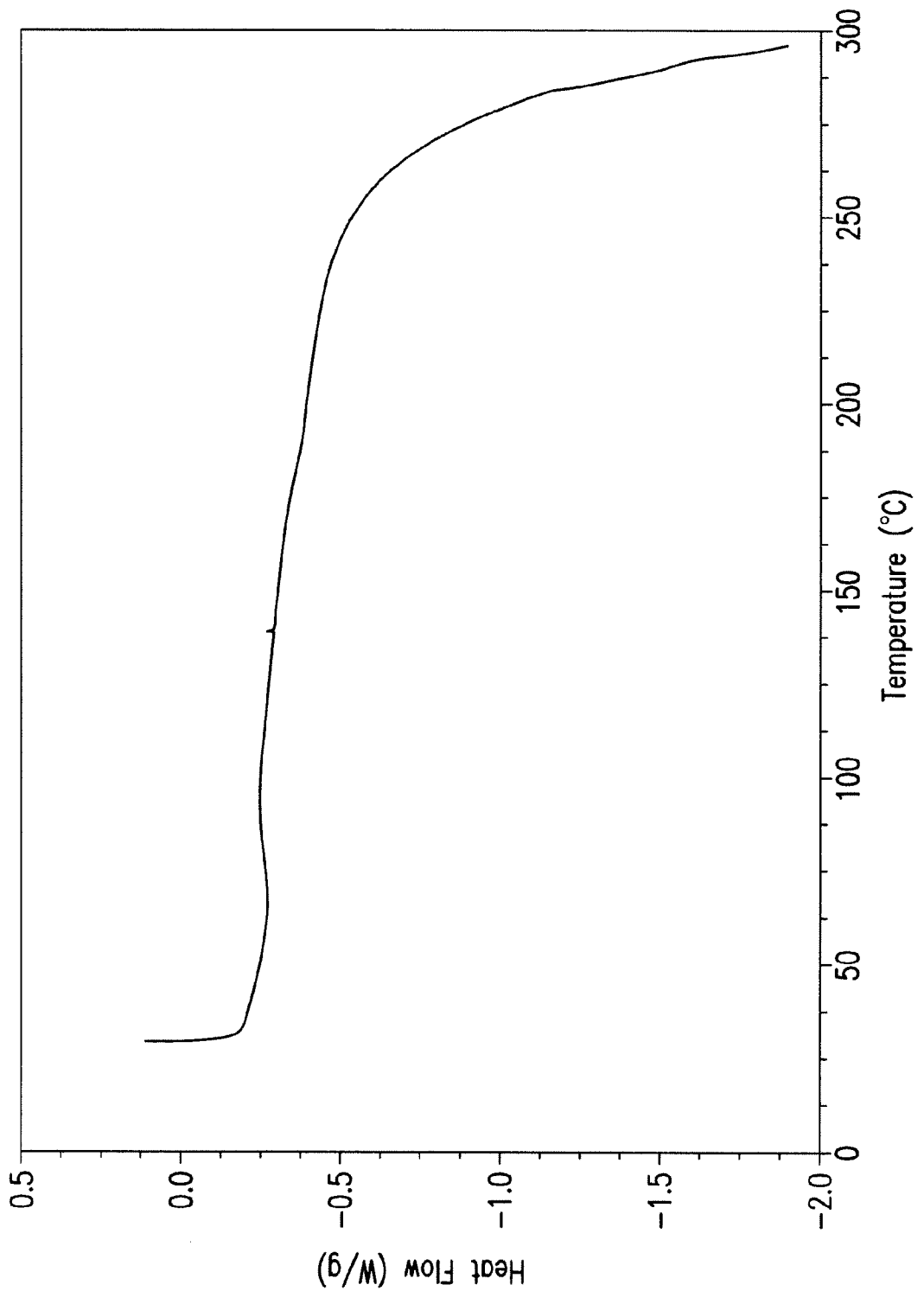
FIG. 24 represents a DSC spectrum of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride in DMSO-$d_6$ prepared using the processes described herein.

In one embodiment, the purity profile of a reaction mixture or an isolated product of the processes provided herein is analyzed by one or more analytical method(s), such as, e.g., HPLC (high performance liquid chromatography), GC (gas chromatography), and TLC (thin layer chromatography), as described herein elsewhere. In one embodiment, an impurity is detectable by an analytical method, such as, e.g., HPLC, GC, or TLC. In one embodiment, a contemplated impurity is below the level of detection, i.e., undetectable, by an analytical method, such as, e.g., HPLC, GC, or TLC. In one embodiment, the impurity or contemplated impurity in the reaction mixture or isolated product of the processes provided herein includes, but is not limited to, the starting material used in the reaction or the starting material used in the proceeding steps. In one embodiment, the impurity or contemplated impurity in the reaction mixture or isolated product of Steps F and G includes, but is not limited to, N-{4-[7-(2-morpholin-4-ylethoxy)(4-hydroimidazo[2,1-b]benzothiazol-2-yl)]-phe-nyl}({4-[7-(2-morpholin-4-ylethoxy)(4-hydroimidazol[2,1-b]benzothiazol-2-yl)]-phenyl}amino)carboxamide (XI), among others. In one embodiment, when phenyl chloroformate is used as the starting material in Step F, the impurity or contemplated impurity in the reaction mixture or the isolated product is phenol. In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, wherein the symmetrical urea impurity (XI) is present at a level of about 0%, less than about 0.05%, less than about 0.1%, less than about 0.5%, less than about 0.8%, less than about 1%, less than about 2%, less than about 5%, less than about 6%, or less than about 7%, for example, as analyzed by HPLC (% area relative to total). In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, wherein the symmetrical urea impurity (XI) is present at a level of less than about 0.05%, for example, as analyzed by HPLC (% area relative to total). In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, wherein the symmetrical urea impurity (XI) is not detectable, such as, e.g., by HPLC analysis. In one embodiment, the processes provided herein produce N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, with a purity profile as shown in FIG. 18 or 19.

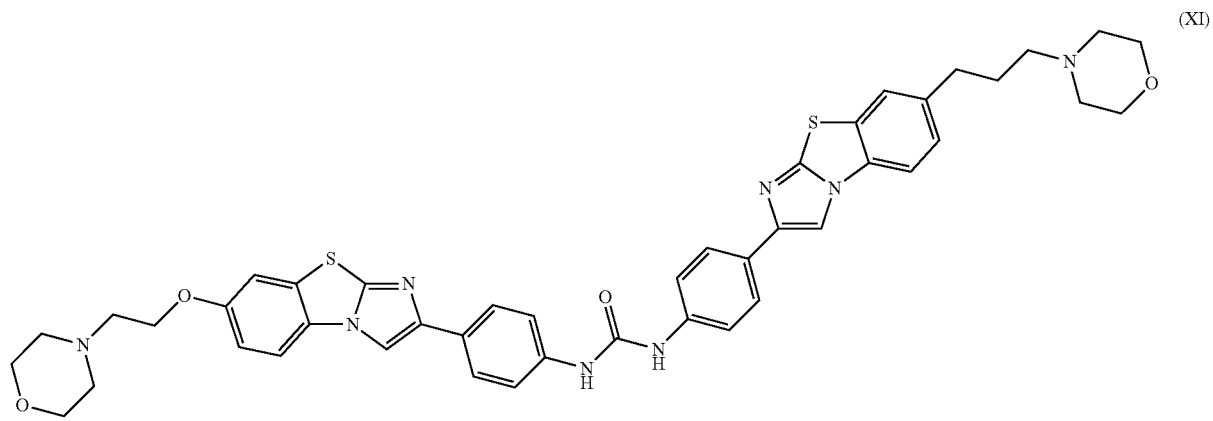 [SMILES: O=C(Nc1ccc(-c2cn3c(n2)sc2cc(CCCN4CCOCC4)ccc23)cc1)Nc1ccc(-c2cn3c(n2)sc2cc(OCCN4CCOCC4)ccc23)cc1]

In one embodiment, the reaction mixture or the isolated product of the processes provided herein contains no detectable impurity (XI), as monitored by a method, such as, e.g., HPLC. In one embodiment, the reaction mixture or the isolated product of the processes provided herein contains impurity (XI) at a level of less than about 0.5% w/w, less than about 0.2% w/w, less than about 0.1% w/w, less than about 0.05% w/w, less than about 0.02% w/w, less than about 0.01% w/w, less than about 0.005% w/w, less than about 0.002% w/w, less than about 0.001% w/w, less than about 0.0005% w/w, less than about 0.0002% w/w, or less than about 0.0001% w/w relative to the total batch.

In one embodiment, the impurity or contemplated impurity in an isolated product of the processes provided herein is a volatile organic compound, such as, e.g., methanol, dimethylformamide, dichloromethane, toluene, acetone, methyl t-butyl ether, ethanol, or tetrahydrofuran. In one embodiment, the impurity or contemplated impurity in an isolated product of the processes provided herein is an organic solvent, such as, e.g., methanol, dimethylformamide, dichloromethane, toluene, acetone, methyl t-butyl ether, ethanol, or tetrahydrofuran.

In one embodiment, the weight loss on drying (LOD) of the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, produced by a process provided herein, is less than about 5% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w relative to the total batch.

In one embodiment, the residue on ignition of the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, produced by a process provided herein, is less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w relative to the total batch.

In one embodiment, the total heavy-metal-based impurity in the N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, produced by a process provided herein, is less than about 500 ppm (parts per million) w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch.

In one embodiment, provided herein are processes for preparing N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that is substantially free of one or more residual solvents, including but not limited to, methanol, ethanol, dimethylformamide, toluene, dichloromethane, acetone, methyl t-butyl ether, and tetrahydrofuran. In one embodiment, the residual solvent or the contemplated residual solvent is less than about 5,000 ppm w/w, less than about 2,000 ppm w/w, less than about 1,000 ppm w/w, less than about 500 ppm w/w, less than about 200 ppm w/w, less than about 100 ppm w/w, less than about 50 ppm w/w, less than about 20 ppm w/w, less than about 10 ppm w/w, less than about 5 ppm w/w, less than about 2 ppm w/w, less than about 1 ppm w/w, less than about 0.5 ppm w/w, less than about 0.2 ppm w/w, or less than about 0.1 ppm w/w relative to the total batch. In one embodiment, the contemplated residual solvent, such as, e.g., methanol, ethanol, dimethylformamide, toluene, dichloromethane, acetone, methyl t-butyl ether, and tetrahydrofuran, cannot be detected.

In one embodiment, provided herein are processes for preparing N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that has a water content of less than about 5% w/w, less than about 4% w/w, less than about 3% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, or less than about 0.1% w/w relative to the total batch.

In one embodiment, provided herein are processes for preparing N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, that has the appearance of a white or off-white solid.

In one embodiment, one or more steps of the processes provided herein is carried out under GMP (Good Manufacturing Process) conditions. In one embodiment, one or more steps of the processes provided herein is carried under non-GMP conditions.

In one embodiment, provided herein are processes for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising the step of reacting 7-(2-morpholin-4-yl-ethoxy)-2-(4-aminophenyl)imidazo[2,1-b]benzothiazole (VIII) with a 5-tert-butylisoxazol-3-ylcarbamate derivative (X) to yield N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I). In one embodiment, the 5-tert-butylisoxazol-3-ylcarbamate derivative is phenyl 5-tert-butylisoxazol-3-ylcarbamate. In one embodiment, the 5-tert-butylisoxazol-3-ylcarbamate derivative is prepared from 3-amino-5-tert-butyl isoxazole (IX). In one embodiment, the isolated yield of the reaction of compound (VIII) with compound (X) is greater than about 70%, greater than about 80%, greater than about 85%, greater than about 90%, greater than about 95%, greater than about 98%, or greater than about 99%. In one embodiment, the purity of the isolated product (I) from the reaction of compound (VIII) with compound (X) is greater than about 95% w/w, greater than about 96% w/w, greater than about 97% w/w, greater than about 98% w/w, greater than about 99% w/w, greater than about 99.5% w/w, greater than about 99.8% w/w, greater than about 99.9% w/w, greater than about 99.95% w/w, greater than about 99.98% w/w, or greater than about 99.99% w/w relative to the total batch. In one embodiment, the isolated product (I) from the reaction of compound (VIII) with compound (X) is substantially free of one or more impurities or contemplated impurities. In one embodiment, the isolated product (I) from the reaction of compound (VIII) with compound (X) is substantially free of impurity (XI). In one embodiment, the isolated product (I) from the reaction of compound (VIII) with compound (X) contains no detectable impurity (XI). In one embodiment, the isolated product (I) from the reaction of compound (VIII) with compound (X) contains less than about 1% w/w, less than about 0.5% w/w, less than about 0.2% w/w, less than about 0.1% w/w, less than about 0.05% w/w, less than about 0.02% w/w, less than about 0.01% w/w, less than about 0.005% w/w, less than about 0.002% w/w, or less than about 0.001% w/w, of impurity (XI). In one embodiment, the molar ratio of compound (X) relative to compound (VIII) used in the reaction of compound (X) with compound (VIII) is about 0.8 (i.e., [Compound (X)]/[Compound (VIII)]=0.8), about 0.9, about 1.0, about 1.1, about 1.2, about 1.3, about 1.4, about 1.5, about 1.6, about 1.7, about 1.8, about 1.9, or about 2.0. In one embodiment, the molar ratio of compound (X) relative to compound (VIII) used in the reaction of compound (X) with compound (VIII) is about 1.0, about 1.1, about 1.2, or about 1.3. In one embodiment, the product (I) of the reaction of compound (VIII) with compound (X) is isolated by filtration or centrifuge. In one embodiment, the product (I) of the reaction of compound (VIII) with compound (X) is isolated without column chromatography.

In one embodiment, provided herein are processes for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising any one, two, three, four, five, six, seven of the steps of:

(A) converting 2-amino-6-alkoxybenzothiazole (II), wherein $R^1$ is a suitable phenolic hydroxyl protecting group, to 2-amino-6-hydroxybenzothiazole (III);

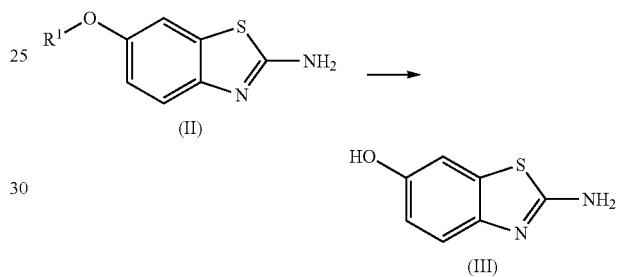

(B) reacting 2-amino-6-hydroxybenzothiazole (III) with compound (IV), wherein $X^1$ is a leaving group, to yield 2-(4-nitrophenyl)imidazo[2,1-b]benzothiazol-7-ol (V);

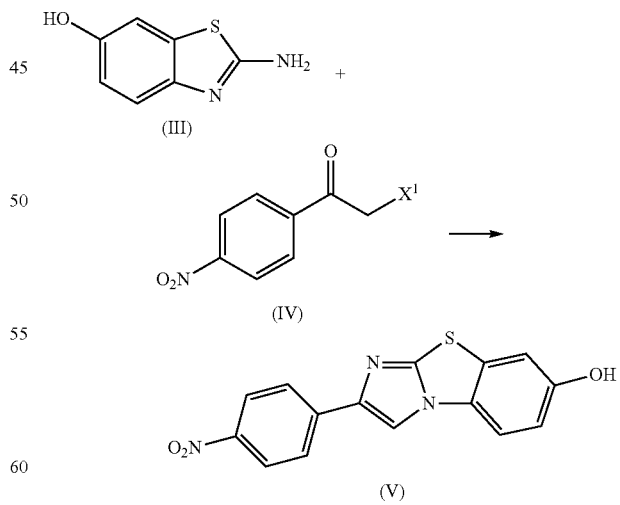

(C) reacting 2-(4-nitrophenyl)imidazo[2,1-b]benzothiazol-7-ol (V) with compound (VI), wherein $X^2$ is a leaving group, to yield 7-(2-morpholin-4-yl-ethoxy)-2-(4-nitrophenyl)imidazo[2,1-b]benzothiazole (VII);

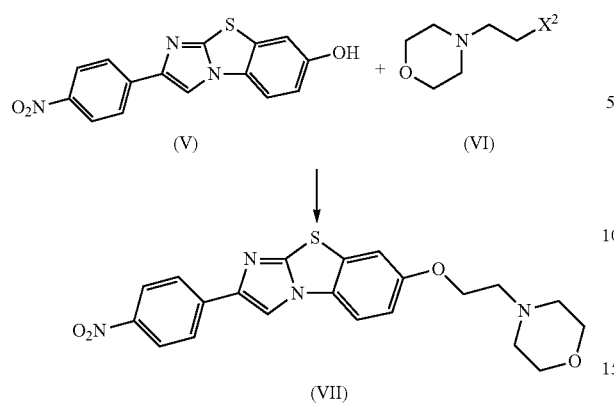

(V)  (VI)

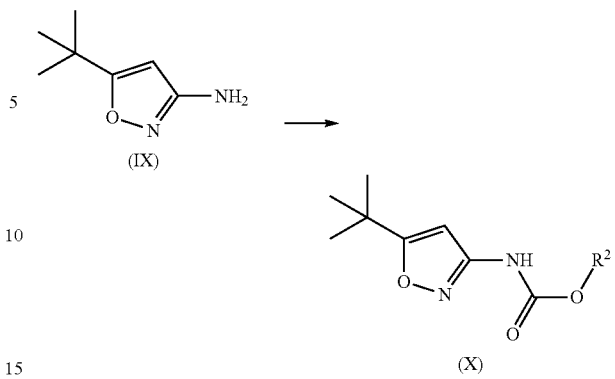

(IX)

(VII)

(X)

(D) reducing 7-(2-morpholin-4-yl-ethoxy)-2-(4-nitrophenyl) imidazo[2,1-b]benzothiazole (VII) to yield 7-(2-morpholin-4-yl-ethoxy)-2-(4-aminophenyl)imidazo[2,1-b]benzothiazole (VIII);

(F) reacting 7-(2-morpholin-4-yl-ethoxy)-2-(4-aminophenyl)imidazo[2,1-b]benzothiazole (VIII) with a 5-tert-butyl-isoxazol-3-ylcarbamate derivative (X) to yield N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I); and

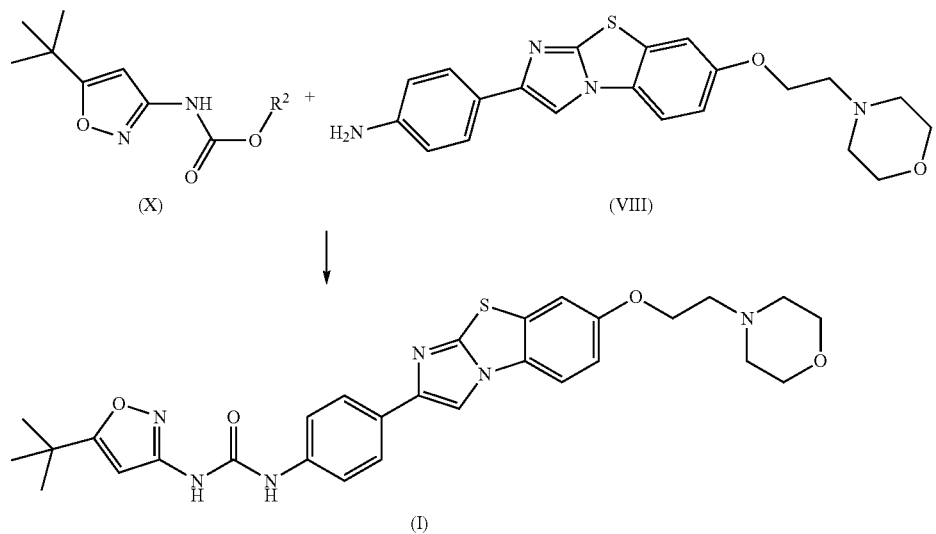

(X)  (VIII)

(I)

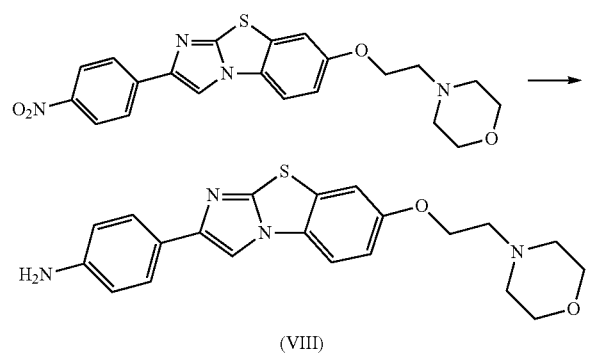

(VIII)

(E) converting 3-amino-5-tert-butyl isoxazole (IX) to a 5-tert-butylisoxazol-3-ylcarbamate derivative (X), wherein $R^2$ is optionally substituted aryl, heteroaryl, alkyl, or cycloalkyl;

(G) converting N-(5-tert-butyl-isoxazol-3-yl)-N'-{4-[7-(2-morpholin-4-yl-ethoxy)imidazo[2,1-b][1,3]benzo-thiazol-2-yl]phenyl}urea to an acid addition salt of N-(5-tert-butyl-isoxazol-3-yl)-N'-{4-[7-(2-morpholin-4-yl-ethoxy)imidazo [2,1-b][1,3]benzo-thiazol-2-yl]phenyl}urea.

In certain embodiments, provided herein are processes for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea, or a pharmaceutically acceptable salt, solvate, hydrate, or polymorph thereof, as depicted in Scheme 1, wherein $R^1$, $R^2$, $X^1$, and $X^2$ are defined herein elsewhere. In specific embodiments, provided herein are processes for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising any one, two, three, four, five, six, seven, of the Steps A, B, C, D, E, F, and G, as depicted in Scheme 1.

Scheme 1:
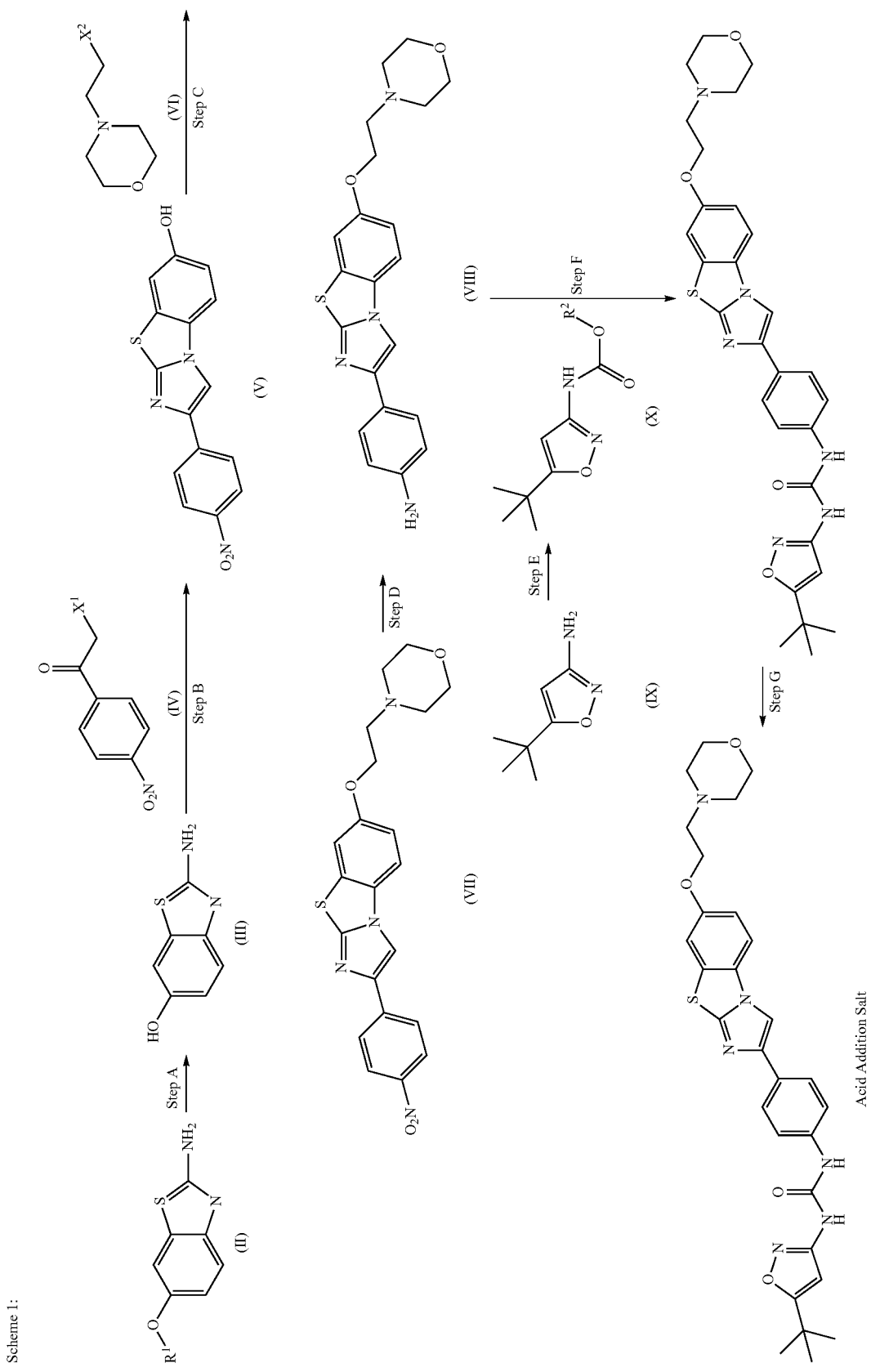

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step A. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step B. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step C. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step D. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step E. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step G.

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step E and Step F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step F and Step G. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step E, Step F, and Step G.

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step A and Step F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step B and Step F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step C and Step F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Step D and Step F.

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps D, E, and F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps C, D, E, and F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps B, C, D, E, and F. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps A, B, C, D, E, and F.

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps D, E, F, and G. In one embodiment, provided herein is a process for the preparation of N-(5-tert-butyl-isoxazol-3-yl)-N'-{-4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps C, D, E, F, and G. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps B, C, D, E, F, and G. In one embodiment, provided herein is a process for the preparation of N-(5-tert-butyl-isoxazol-3-yl)-N'-{4-[7-(2-morpholin-4-yl-ethoxy) imidazo[2,1-b][1,3]benzo-thiazol-2-yl]phenyl}urea (I), or a pharmaceutically acceptable salt, solvate, hydrate, or polymorph thereof, comprising Steps A, B, C, D, E, F, and G.

In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps B and C. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps A and B. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps A, B, and C. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzo-thiazol-2-yl]phenyl}urea (I), or a pharmaceutically acceptable salt, solvate, hydrate, or polymorph thereof, comprising Steps B, C, and D. In one embodiment, provided herein is a process for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea (I), or a pharmaceutically acceptable salt, solvate, hydrate, or polymorph thereof, comprising Steps A, B, C, and D.

Detailed descriptions of Steps A, B, C, D, E, F, and G are provided herein elsewhere.

1. Step A

In one embodiment, the 2-amino-6-alkoxybenzothiazole compound (II) used in the reaction of Step A is:

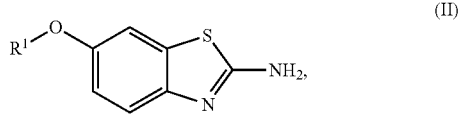

(II)

wherein $R^1$ is a suitable phenolic hydroxyl protecting group. Suitable phenolic hydroxyl protecting group are described, for example, in Greene & Wuts, "Protective Groups in Organic Synthesis," 4th Edition, Wiley Interscience, 2006; Kocienski, "Protecting Groups," 3rd Edition, Thieme, 2005. In one embodiment, $R^1$ is optionally substituted $C_1$-$C_6$ alkyl. In one embodiment, $R^1$ is unsubstituted $C_1$-$C_6$ alkyl. In some embodiments, $R^1$ is optionally substituted straight chain alkyl. In some embodiments, $R^1$ is optionally substituted branched chain alkyl. In some embodiments, $R^1$ is methyl or ethyl. In some embodiments, $R^1$ is methyl. In some embodiments, the 2-amino-6-alkoxybenzothiazole (II) is 2-amino-6-methoxybenzothiazole, which is represented by the structure:

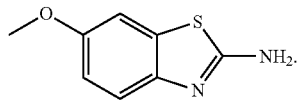

In one embodiment, 2-amino-6-methoxybenzothiazole is obtained from a commercial supplier, such as, e.g., Sigma-Aldrich®, Inc., Alfa Aesar, Apollo Scientific, Ltd., TCI America, and Du-Hope International Group, Nanjing, China.

In one embodiment, the reaction of Step A is performed by stirring a mixture of compound (I) and a deprotecting reagent in a suitable solvent at a suitable temperature in a reaction vessel until the reaction is substantially complete. In one embodiment, compound (I) is added to a stirred mixture of a deprotecting reagent in a suitable solvent. In one embodiment, a deprotecting reagent is added to a stirred mixture of compound (I) in a suitable solvent.

In one embodiment, the deprotecting reagent is a suitable reagent for deprotecting a phenolic hydroxyl protecting group. See, e.g., Greene & Wuts, *Protective Groups in Organic Synthesis*, 4th Edition, Wiley Interscience, 2006. In one embodiment, the deprotecting reagent is hydrobromic acid, boron tribromide, hydroiodic acid, or iodotrimethylsilane. In one embodiment, the deprotecting reagent is hydrobromic acid. In one embodiment, the deprotecting reagent is aqueous hydrobromic acid. In one embodiment, the deprotecting reagent is 48% w/w aqueous hydrobromic acid.

In one embodiment, a molar excess of the deprotecting reagent is used in the reaction of Step A. In one embodiment, the molar ratio of the deprotecting reagent relative to compound (II) used in the reaction of Step A is about 1 (i.e., [deprotecting reagent]/[compound (II)]=1), about 2, about 3, about 4, about 5, about 6, about 7, about 8, about 9, about 10, about 11, about 12, about 13, about 14, about 15, or greater than 15. In one embodiment, the molar ratio of the deprotecting reagent relative to compound (II) used in the reaction of Step A is about 10.

In one embodiment, the reaction is carried out in a protic solvent. In one embodiment, the reaction is carried out in an aprotic solvent. In one embodiment, the reaction is carried out in water.

In one embodiment, the reaction of Step A is carried out at ambient temperature. In one embodiment, the reaction of Step A is carried out at elevated temperature. In one embodiment, the reaction of Step A is carried out under a refluxing condition. In one embodiment the reaction of Step A is carried out at a temperature of about 20° C., about 30° C., about 40° C., about 50° C., about 60° C., about 70° C., about 80° C., about 90° C., about 100° C., about 110° C., about 120° C., or greater than about 120° C. In one embodiment, the reaction of Step A is carried out at a temperature of between about 105° C. and about 110° C.

The reaction time of the reaction of Step A can vary from about 1 hr to about 24 hr, depending on the reaction temperature, the reagents, and the equivalents and concentrations of reagents in the reaction mixture. In specific embodiments, the reaction time of Step A is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In some embodiments, the reaction time is about 2 hr, about 3 hr, about 4 hr, about 5 hr, or about 6 hr, at a reaction temperature of between about 105° C. and about 110° C., when the deprotecting reagent is aqueous hydrobromic acid. In some embodiments, the progress of the reaction is monitored, such as by taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that 2-amino-6-alkoxybenzothiazole is present at a level of less than about 2% (i.e., % area by HPLC<2%) in the reaction mixture.

In one embodiment, when the reaction of Step A is substantially complete, the reaction mixture is cooled to allow the precipitation of product (III). In one embodiment, the reaction mixture is cooled to a temperature of about 0° C., about 5° C., or about 10° C. In one embodiment, the reaction mixture is cooled to a temperature of between about 0° C. and about 5° C. In one embodiment, the reaction mixture is maintained at the cooling temperature (e.g., about 0° C., about 5° C., or about 10° C.) for about 15 min, about 30 min, about 45 min, about 1 hr, about 1.5 hr, or about 2 hr. In some embodiments, a counter-solvent is added to facilitate the precipitation of product (III). In other embodiments, no counter-solvent is added.

In one embodiment, the suspension containing the precipitated product (III) is filtered or centrifuged to separate the solid from the mixture. In some embodiments, the wet solid is pressed to remove any excess dealkylating reagent or other impurities. In one embodiment, the solid is re-suspended in a neutralizing solution, such as, e.g., saturated sodium bicarbonate solution, and then filtered. In one embodiment, the filter cake containing product (III) is washed with water. In one embodiment, the isolated solid containing product (III) is air dried. In one embodiment, the isolated solid containing product (III) is dried under vacuum. In some embodiments, the solid is dried in a vacuum oven. In one embodiment, the drying is carried out at ambient temperature. In one embodiment, the drying is carried out at a temperature of about 20° C., about 25° C., about 30° C., about 35° C., about 40° C., about 45° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr. In some embodiments, the isolated product of Step A may be further purified by re-crystallization.

In one embodiment, the yield of the isolated product of Step A is greater than about 60%, greater than about 70%, greater than about 80%, greater than about 85%, greater than about 90%, greater than about 95%, greater than about 98%, or greater than about 99%. In one embodiment, the purity of the isolated product of Step A is about 90% w/w, about 95% w/w, about 98% w/w, about 99% w/w, about 99.5% w/w, about 99.8% w/w, or about 99.9% w/w relative to the total batch. In one embodiment, the purity of the isolated product of Step A is greater than about 90% w/w, greater than about 95% w/w, greater than about 98% w/w, greater than about 99% w/w, greater than about 99.5% w/w, greater than about 99.8% w/w, or greater than about 99.9% w/w relative to the total batch.

2. Step B

In one embodiment, compound (IV) used in the reaction of Step B is:

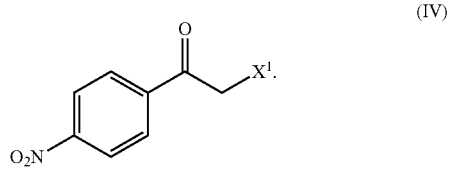

wherein $X^1$ is a leaving group. In one embodiment, $X^1$ is halo, alkylsulfonate, or arylsulfonate. See, e.g., Prakash, et al., *Synlett* 1994, 221; Moriarty, et al., *Synthesis* 1992, 845. In one embodiment, $X^1$ is halo. In one embodiment, $X^1$ is iodo. In one embodiment, $X^1$ is bromo. In one embodiment, $X^1$ is chloro. In one embodiment, $X^1$ is fluoro. In one embodiment, compound (IV) is 2-bromo-4'-nitroacetophenone, which is represented by the structure:

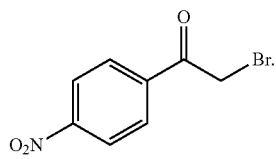

In one embodiment, compound (III) is obtained from Step A. In one embodiment, compound (III) is obtained from a commercial supplier. In one embodiment, 2-bromo-4'-nitroacetophenone is obtained from a commercial supplier, such as, e.g., Sigma-Aldrich®, Inc., Alfa Aesar, Betapharma Shanghai Co., Ltd., Oakwood Products, Inc., and Du-Hope International Group, Nanjing, China.

In one embodiment, the reaction of Step B is performed by stirring a mixture of compound (III) and compound (IV) in a suitable solvent at a suitable temperature until the reaction is substantially complete. In one embodiment, the reaction of Step B is carried out in the presence of base. In one embodiment, the base is added to a stirred mixture of compound (III) and compound (IV) in a suitable solvent, and the resulting mixture is stirred at a suitable temperature until the reaction is substantially complete.

In one embodiment, the reaction of Step B is carried out in the presence of an organic or inorganic base. In one embodiment, the reaction of Step B is carried out in the presence of one or more carbonate or bicarbonate salts. In one embodiment, the reaction of Step B is carried out in the presence of sodium bicarbonate.

In one embodiment, the molar ratio of compound (IV) relative to compound (III) used in the reaction of Step B is about 0.9 (i.e., [compound (IV)]/[compound (III)]=0.9), about 1.0, about 1.1, about 1.2, about 1.3, about 1.4, or about 1.5. In one embodiment, the molar ratio of compound (IV) relative to compound (III) used in the reaction of Step B is about 1.0, about 1.1, or about 1.2. In one embodiment, the molar ratio of compound (IV) relative to compound (III) used in the reaction of Step B is about 1.1.

In one embodiment, the molar ratio of the base used in the reaction of Step B relative to compound (III) is about 0.9 (i.e., [Base]/[compound (III)]=0.9), about 1.0, about 1.1, about 1.2, about 1.3, about 1.4, or about 1.5. In one embodiment, the molar ratio of the base used in the reaction of Step B relative to compound (III) is about 0.9, about 1.0, or about 1.1. In one embodiment, the molar ratio of the base used in the reaction of Step B relative to compound (III) is about 1.0.

In one embodiment, the reaction of Step B is carried out in a polar solvent. In one embodiment, the reaction of Step B is carried out in a non-polar solvent. In one embodiment, the reaction of Step B is carried out in a protic solvent. In one embodiment, the reaction of Step B is carried out in an aprotic solvent. In one embodiment, the reaction of Step B is carried out in an alcohol. In one embodiment, the reaction to Step B is carried out in ethanol. In one embodiment, the reaction of Step B is carried out in isopropanol or n-butanol. In one embodiment, the reaction of Step B is carried out in isopropanol. In one embodiment, the reaction of Step B is carried out in n-butanol.

In one embodiment, the reaction of Step B is carried out in alcohol in the presence of base. In one embodiment, the reaction of Step B is carried out in alcohol in the presence of one or more carbonate or bicarbonate salts. In one embodiment, the reaction of Step B is carried out in n-butanol in the presence of base. In one embodiment, the reaction of Step B is carried out in n-butanol in the presence of one or more carbonate or bicarbonate salts.

In one embodiment, the reaction of Step B is carried out at ambient temperature. In one embodiment, the reaction of Step B is carried out at elevated temperature. In one embodiment, the reaction of Step B is carried out under a refluxing condition. In one embodiment, the reaction of Step B is carried out at a temperature of about 20° C., about 30° C., about 40° C., about 50° C., about 60° C., about 70° C., about 80° C., about 90° C., about 95° C., about 100° C., about 110° C., about 120° C., about 130° C., about 140° C., about 150° C., or greater than about 150° C. In one embodiment, the reaction of Step B is carried out in n-butanol under a refluxing condition. In one embodiment, the reaction of Step B is carried out at a temperature of between about 110° C. and about 115° C.

The reaction time of the reaction of Step B can vary from about 1 hr to about 24 hr, depending on the reaction temperature, the reagents, and the equivalents and concentrations of reagents in the reaction mixture. In specific embodiments, the reaction time of Step B is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In some embodiments, the reaction time is about 1 hr, about 2 hr, about 3 hr, about 4 hr, or about 5 hr, when sodium bicarbonate is used as the base to facilitate the reaction in n-butanol at a reaction temperature of between about 110° C. and about 115° C. In some embodiments, the progress of the reaction is monitored, such as by taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that compound (III) is present at a level of less than about 2% (i.e., % area by HPLC<2%) in the reaction mixture.

In one embodiment, when the reaction of Step B is substantially complete, the reaction mixture is cooled to allow the precipitation of product (V). In one embodiment, the reaction mixture is cooled to a temperature of about 0° C., about 5° C., about 10° C., about 20° C., about 30° C., about 40° C., about 50° C., or about 60° C. In one embodiment, the reaction mixture is maintained at the cooling temperature for about 15 min, about 30 min, about 45 min, about 1 hr, about 1.5 hr, or about 2 hr. In one embodiment, when the reaction is carried out at a temperature of greater than about 100° C., the reaction mixture is slowly cooled to a temperature of between about 50° C. and about 60° C. first, and then slowly cooled to a temperature of between about 0° C. and about 5° C. and stirred for about 15 min. In some embodiments, a counter-solvent is added to facilitate the precipitation of product (V). In other embodiments, no counter-solvent is added.

In one embodiment, the suspension containing the precipitated product (V) is filtered or centrifuged to separate the solid from the mixture. In some embodiments, the wet solid is dried on the filter. In some embodiments, the solid is dried in a vacuum oven. In one embodiment, the solid obtained from the filtration of the reaction mixture is re-suspended in water, stirred for about 30 min, and then filtered. In one embodiment, the resulting solid is re-suspended and stirred in an organic solvent, such as, e.g., acetone, and then filtered. In one embodiment, the solid on the filter is washed with a solvent, such as, e.g., acetone. In one embodiment, the isolated solid is air dried. In one embodiment, the isolated solid containing product (V) is dried under vacuum. In one embodiment, the drying is carried out at ambient temperature. In one embodiment, the drying is carried out at a temperature of about 20° C., about 30° C., about 40° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr. In some embodiments, the isolated product of Step B may be further purified by re-crystallization.

In one embodiment, the yield of the isolated product of Step B is greater than about 60%, greater than about 70%, greater than about 75%, greater than about 80%, greater than about 85%, greater than about 90%, greater than about 95%, or greater than about 98%. In certain embodiments, the yield of the isolated product of Step B is greater than about 80%, or greater than about 85%. In one embodiment, the purity of the isolated product of Step B is about 90% w/w, about 95% w/w, about 98% w/w, about 99% w/w, about 99.5% w/w, about 99.8% w/w, or about 99.9% w/w relative to the total batch. In one embodiment, the purity of the isolated product of Step B is greater than about 90% w/w, greater than about 95% w/w, greater than about 98% w/w, greater than about 99% w/w, greater than about 99.5% w/w, greater than about 99.8% w/w, or greater than about 99.9% w/w relative to the total batch.

3. Step C

In one embodiment, compound (VI) used in the reaction of Step C is:

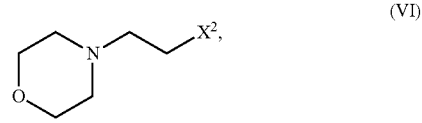

(VI)

wherein $X^2$ is a leaving group. In one embodiment, $X^2$ is halo, alkylsulfonate, or arylsulfonate. See, e.g., Prakash, et al., *Synlett* 1994, 221; Moriarty, et al., *Synthesis* 1992, 845. In one embodiment, $X^2$ is tosylate, nosylate, mesylate, or triflate. In one embodiment, $X^2$ is halo. In one embodiment, $X^2$ is iodo. In one embodiment, $X^2$ is bromo. In one embodiment, $X^2$ is chloro. In one embodiment, $X^2$ is fluoro. In one embodiment, compound (VI) is 4-(2-chloroethyl)morpholine, which is represented by the structure:

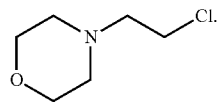

In some embodiments, 4-(2-chloroethyl)morpholine is supplied as its hydrochloride salt, which is used in Step C as a starting material. In one embodiment, 4-(2-chloroethyl) morpholine is obtained from a commercial supplier, such as, e.g., Sigma-Aldrich®, Inc., TCI America, Alfa Aesar, Pfaltz & Bauer, Inc., and Apollo Scientific, Ltd.

In one embodiment, the reaction of Step C is performed by stirring a mixture of compound (V) and compound (VI) in a suitable solvent at a suitable temperature until the reaction is substantially complete. In one embodiment, the reaction of Step C is carried out in the presence of base. In one embodiment, the reaction of Step C is carried out in the presence of a catalyst. In one embodiment, the reaction of Step C is carried out in the presence of a base and a catalyst. In one embodiment, the base and/or catalyst is added to a stirred mixture of compound (V) and compound (VI) in a suitable solvent, and the resulting mixture is stirred at a suitable temperature until the reaction is substantially complete.

In one embodiment, the reaction of Step C is carried out in the presence of an organic or inorganic base. In one embodiment, the reaction of Step C is carried out in the presence of one or more carbonate or bicarbonate salts. In one embodiment, the reaction of Step C is carried out in the presence of potassium carbonate.

In one embodiment, the reaction of Step C is carried out in the presence of a catalyst. In one embodiment, the catalyst is a phase-transfer reagent. In one embodiment, the catalyst is tetrabutylammonium iodide.

In one embodiment, the reaction of Step C is carried out in the presence of potassium carbonate and tetrabutylammonium iodide.

In one embodiment, the molar ratio of compound (VI) relative to compound (V) used in the reaction of Step C is about 1.0 (i.e., [compound (VI)]/[compound (V)]=1.0), about 1.5, about 2.0, about 2.5, about 3.0, about 3.5, about 4.0, or about 5.0. In one embodiment, the molar ratio of compound (VI) relative to compound (V) used in the reaction of Step C is about 2.5, about 3.0, or about 3.5. In one embodiment, the molar ratio of compound (VI) relative to compound (V) used in the reaction of Step C is about 3.0.

In one embodiment, the molar ratio of the base used in the reaction of step C relative to compound (V) is about 0.1 (i.e., [Base]/[compound (V)]=0.1), about 0.5, about 1.0, about 1.5, about 2.0, about 2.5, about 3.0, about 3.5, about 4.0, or about 5.0. In one embodiment, the molar ratio of the base used in the reaction of Step C relative to compound (V) is about 2.5, about 3.0, or about 3.5. In one embodiment, the molar ratio of the base used in the reaction of Step C relative to compound (V) is about 3.0.

In one embodiment, the molar ratio of the catalyst used in the reaction of step C relative to compound (V) is about 0.1 (i.e., [Catalyst]/[compound (V)]=0.1), about 0.2, about 0.3, about 0.4, about 0.5, or greater than about 0.5. In one embodiment, the molar ratio of the catalyst used in the reaction of Step C relative to compound (V) is about 0.1, about 0.2, or about 0.3. In one embodiment, the molar ratio of the catalyst used in the reaction of Step C relative to compound (V) is about 0.2.

In one embodiment, the reaction of Step C is carried out in a polar solvent. In one embodiment, the reaction of Step C is carried out in a non-polar solvent. In one embodiment, the reaction of Step C is carried out in an aprotic solvent. In one embodiment, the reaction of Step C is carried out in dichloromethane, ethyl acetate, tetrahydrofuran, acetone, methyl ethyl ketone, methyl t-butyl ether, acetonitrile, N-methylpyrrolidinone, or N,N-dimethylformamide, or the like. In one embodiment, the reaction of Step C is carried out in N,N-dimethylformamide (DMF). In one embodiment, the reaction of Step C is carried out in anhydrous DMF.

In one embodiment, the reaction of Step C is carried out at ambient temperature. In one embodiment, the reaction of Step C is carried out at elevated temperature. In one embodiment, the reaction of Step C is carried out at a temperature of about 20° C., about 30° C., about 40° C., about 50° C., about 60° C., about 70° C., about 80° C., about 90° C., about 95° C., about 100° C., about 110° C., about 120° C., about 130° C., about 140° C., about 150° C., or greater than about 150° C. In one embodiment, the reaction of Step C is carried out at a temperature of about 90° C., about 100° C., or about 110° C. In one embodiment, the reaction mixture of Step C is first heated to a temperature of about 90° C., stirred at 90° C. for at least about 15 min, and then heated to a temperature of about 110° C. In one embodiment, the reaction of Step C is carried out at a temperature of between about 90° C. and about 110° C. In one embodiment, the reaction of Step C is carried out at a temperature of about 105° C., about 110° C., or about 115° C. In one embodiment, the reaction of Step C is carried out at a temperature of about 110° C.

The reaction time of the reaction of Step C can vary from about 1 hr to about 24 hr, depending on the reaction temperature, the reagents, and the equivalents and concentrations of reagents in the reaction mixture. In specific embodiments, the reaction time of Step C is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In some embodiments, the reaction time is about 1 hr, about 2 hr, about 3 hr, about 4 hr, about 5 hr, about 6 hr, or about 7 hr, when potassium carbonate and tetrabutylammonium iodide is used as the base and catalyst, respectively, to facilitate the reaction in DMF at a reaction temperature of between about 105° C. and about 115° C. In some embodiments, the progress of the reaction is monitored, such as by taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that compound (V) is present at a level of less than about 1% (i.e., % area by HPLC<1%) in the reaction mixture. In some embodiments, if the reaction is not substantially complete after about 6 hr at a temperature of about 110° C. in DMF, additional compound (VI) may be added to the reaction mixture to react with any remaining compound (V).

In one embodiment, when the reaction of Step C is substantially complete, the reaction mixture is cooled. In one embodiment, the reaction mixture is cooled to a temperature of about 0° C., about 10° C., about 20° C., about 30° C., or about 40° C. In some embodiments, water and acetone are added to the cooled reaction mixture and the resulting mixture is stirred. In one embodiment, the mixture is stirred for about 30 min, about 1.0 hr, about 1.5 hr, about 2.0 hr, about 2.5 hr, about 3.0 hr, or greater than 3.0 hr. In one embodiment, the product (VII) of Step C precipitates out of the mixture as a solid.

In one embodiment, the suspension containing the precipitated product (VII) is filtered or centrifuged to separate the solid from the mixture. In some embodiments, the wet solid is dried on the filter. In some embodiments, the solid is dried in a vacuum oven. In one embodiment, the solid obtained from the filtration of the reaction mixture is washed with water and acetone. In one embodiment, the isolated solid is air dried. In one embodiment, the isolated solid containing product (VII) is dried under vacuum. In one embodiment, the drying is carried out at ambient temperature. In one embodiment, the drying is carried out at a temperature of about 20° C., about 30° C., about 35° C., about 40° C., about 45° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr, or to a constant weight. In some embodiments, the isolated product of Step C may be further purified by re-crystallization.

In one embodiment, the yield of the isolated product of Step C is greater than about 60%, greater than about 70%, greater than about 80%, greater than about 85%, greater than about 90%, greater than about 95%, greater than about 98%, or greater than about 99%. In certain embodiments, the yield of the isolated product of Step C is greater than about 85%, or greater than about 90%. In one embodiment, the purity of the isolated product of Step C is about 90% w/w, about 95% w/w, about 96% w/w, about 97% w/w, about 98% w/w, about 99% w/w, about 99.5% w/w, about 99.8% w/w, or about 99.9% w/w relative to the total batch. In one embodiment, the purity of the isolated product of Step C is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, or greater than about 99.9% w/w relative to the total batch.

In one embodiment, Step C is carried out under GMP conditions.

4. Step D

In one embodiment, the reaction of Step D is carried out in the presence of hydrogen, or a hydrogen transfer reagent, including but not limited to, formic acid, ammonium formate, and cyclohexadiene. In one embodiment, the reaction of Step D is carried out in the presence of hydrogen. In one embodiment, the reaction of Step D is carried out in the presence of a reducing agent, including but not limited to, tin chloride, metallic tin or iron in the presence of acid, lithium aluminum hydride, sodium dithionite, and metallic samarium in the presence of a pyridinium catalyst. In one embodiment, the reaction of Step D is carried out in the presence of a reducing catalyst, including but not limited to, a palladium catalyst, a rhodium catalyst, and a ruthenium catalyst. In one embodiment, the reaction of Step D is carried out in the presence of a reducing catalyst, including but not limited to, palladium on carbon, palladium hydroxide on carbon, and Raney Ni. In one embodiment, the reaction of Step D is carried out in the presence of Raney Ni. In one embodiment, the reaction of Step D is carried out in the presence of Raney Ni under hydrogen atmosphere. In one embodiment, the reaction of Step D is carried out in the presence of Raney Ni under about 150 psi hydrogen.

In one embodiment, the reaction of Step D is performed by stirring a mixture of compound (VII) and a reducing agent or catalyst in a suitable solvent at a suitable temperature, in some embodiments, in the presence of hydrogen or a hydrogen transfer reagent, until the reaction is substantially complete. In one embodiment, the reaction of Step D is performed by stirring a mixture of compound (VII) and a reducing catalyst in a suitable solvent at a suitable temperature under hydrogen atmosphere until the reaction is substantially complete. In one embodiment, the reaction of Step D is carried out in a high pressure reactor. In one embodiment, the high pressure reactor is charged with a mixture of compound (VII) in a suitable solvent which is flushed with nitrogen. In one embodiment, the reducing catalyst is added to a mixture of compound (VII) in a suitable solvent under vacuum or an inert atmosphere, such as, e.g., nitrogen. In one embodiment, the high pressure reactor containing a mixture of compound (VII) and the reducing catalyst in a suitable solvent is vented and heated to a suitable temperature, such as, e.g., 50° C. In one embodiment, the reactor is pressurized with hydrogen gas. In one embodiment, the content of the high pressure reactor under hydrogen atmosphere is agitated at a suitable temperature until the reaction is substantially complete.

In one embodiment, the reducing catalyst of Step D is a hydrogenation catalyst known in the art, such as, e.g., Raney nickel or palladium on carbon. In one embodiment, the reducing catalyst of Step D is Raney nickel. In one embodiment, the reaction of Step D is carried out in the presence of Raney nickel.

In one embodiment, the reaction of Step D is carried out under hydrogen atmosphere. In one embodiment, the reaction of Step D is carried out under about 150 psi hydrogen. In one embodiment, the progress of the reaction is monitored by a hydrogen uptake test, i.e., by pressurizing the reactor containing the reaction mixture to a certain positive pressure of hydrogen, such as, e.g., 150 psi, checking the pressure after a period of time, such as, e.g., 1 hr. If the hydrogen pressure drops, such as, e.g., by about 5 psi, the above process is repeated, i.e., re-pressurizing the reactor with hydrogen and checking the pressure after a period of time. If the hydrogen pressure remains about the same, such as, e.g., within about 5 psi of the initial pressure, the reactor is vented and the reaction mixture sampled, such as, e.g., analyzed by HPLC.

In one embodiment, the weight ratio of the reducing agent relative to compound (VII) used in the reaction of Step D is about 1.0 (i.e., [reducing agent]/[compound (VII)]=1.0), about 1.5, about 2.0, about 2.5, about 3.0, about 3.5, about 4.0, or greater than about 4.0. In one embodiment, the weight ratio of the reducing catalyst relative to compound (VII) used in the reaction of Step D is about 0.01 (i.e., [reducing catalyst]/[compound (VII)]=0.01), about 0.05, about 0.1, about 0.2, about 0.3, about 0.4, about 0.5, or greater than about 0.5. In one embodiment, the weight ratio of the reducing catalyst relative to compound (VII) used in the reaction of Step D is about 0.10, about 0.15, about 0.20, or about 0.25. In one embodiment, the weight ratio of the reducing catalyst relative to compound (VII) used in the reaction of Step D is about 0.18.

In one embodiment, the reaction of Step D is carried out in a polar solvent. In one embodiment, the reaction of Step D is carried out in a non-polar solvent. In one embodiment, the reaction of Step D is carried out in a protic solvent. In one embodiment, the reaction of Step D is carried out in an aprotic solvent. In one embodiment, the reaction of Step D is carried out in a mixture of two or more solvents. In one embodiment, the reaction of Step D is carried out in dichloromethane, ethyl acetate, tetrahydrofuran, methyl t-butyl ether, methanol, ethanol, or the like. In one embodiment, the reaction of Step D is carried out in methanol. In one embodiment, the reaction of Step D is carried out in tetrahydrofuran. In one embodiment, the reaction of Step D is carried out in a mixture of methanol and tetrahydrofuran. In one embodiment, the reaction of Step D is carried out in the presence of water.

In one embodiment, the reaction of Step D is carried out at ambient temperature. In one embodiment, the reaction of Step D is carried out at elevated temperature. In one embodiment, the reaction of Step D is carried out at a temperature of about 0° C., about 10° C., about 20° C., about 30° C., about 40° C., about 50° C., about 60° C., about 70° C., about 80° C., or greater than about 80° C. In one embodiment, the reaction of Step D is carried out at a temperature of about 50° C. In one embodiment, the internal temperature of the reaction mixture of Step D is controlled at below about 55° C. through the course of the reaction.

In one embodiment, the reaction of Step D is carried out under hydrogen atmosphere. In one embodiment, the pressure of the hydrogen atmosphere is between about 1 psi and about 3000 psi, between about 30 psi and about 200 psi, or between about 100 psi and about 200 psi. In one embodiment, the pressure of the hydrogen atmosphere is about 1, about 10, about 30, about 50, about 100, about 120, about 150, about 180, about 200, about 250, about 300, about 350, about 400, about 500, about 750, about 1000, about 2000, or about 3000 psi. In one embodiment, the pressure of the hydrogen atmosphere is about 150 psi.

The reaction time of the reaction of Step D can vary from about 1 hr to about 24 hr, depending on the reaction temperature, the hydrogen pressure, the reagents, and the equivalents and concentrations of reagents in the reaction mixture. In specific embodiments, the reaction time of Step D is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In some embodiments, the reaction time is about 2 hr, about 3 hr, about 4 hr, about 5 hr, about 6 hr, about 7 hr, about 8 hr, about 9 hr, or about 10 hr, when the reaction is carried out in a mixture of methanol and THF, in the presence of water, using Raney Ni as the reducing catalyst, under about 150 psi of hydrogen, at a reaction temperature of about 50° C. In some embodiments, the progress of the reaction is monitored using the hydrogen uptake test described herein elsewhere. In some embodiments, after the hydrogen uptake test shows about constant hydrogen pressure, the progress of the reaction is monitored using HPLC, such as by venting the reactor, taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that compound (VII) is present at a level of less than about 0.5% (i.e., % area by HPLC<0.5%) in the reaction mixture.

In one embodiment, when the reaction of Step D is substantially complete, the reaction mixture is filtered to remove the reducing agent or catalyst. In one embodiment, the filtration step is carried out at elevated temperature, such as, e.g., about 50° C., to ensure that most of the product (VIII) remains solubilized during the filtration. In one embodiment, the high pressure reactor is washed with additional solvent, such as, e.g., a mixture of THF and methanol, and the wash is filtered. In one embodiment, the filtrate is concentrated by vacuum distillation. In one embodiment, the filtrate is concentrated by vacuum distillation with internal temperature of less than about 40° C. In one embodiment, the filtrate is concentrated by vacuum distillation to a reduced volume, without completely removing the solvent. In one embodiment, the concentrated mixture containing product (VIII) is cooled. In one embodiment, the concentrated mixture containing product (VIII) is cooled to a temperature of about 0° C., about 10° C., about 20° C., or about 30° C. In one embodiment, the concentrated mixture containing product (VIII) is cooled to about 20° C. In some embodiments, an anti-solvent, such as, e.g., heptane, is added to the cooled mixture containing product (VIII) and the resulting mixture is vacuum distilled. In some embodiments, an anti-solvent, such as, e.g., heptane, is added to the vacuum distilled mixture containing product (VIII). In one embodiment, the mixture containing product (VIII) in the anti-solvent is stirred for at least about 1 hr at ambient temperature, such as, e.g., about 20° C. In one embodiment, the product (VIII) of Step D precipitates out of the mixture as a solid.

In one embodiment, the suspension containing the precipitated product (VIII) is filtered or centrifuged to separate the solid from the mixture. In one embodiment, the product of Step D is collected by filtration or centrifuge in the presence of a non-polar solvent, such as, e.g., heptane. In some embodiments, the solid obtained from filtration or centrifuge is washed with a non-polar solvent, such as, e.g., heptane. In some embodiments, the solid is air-dried. In some embodiments, the solid is dried in a vacuum oven. In one embodiment, the isolated solid containing product (VIII) is dried under vacuum. In one embodiment, the drying is carried out at ambient temperature. In one embodiment, the drying is carried out at a temperature of about 20° C., about 30° C., about 35° C., about 40° C., about 45° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr, or to a constant weight. In one embodiment, the drying is carried out under vacuum at a temperature of less than about 50° C., to a constant weight. In some embodiments, the isolated product of Step D may be further purified by re-crystallization.

In one embodiment, the yield of the isolated product of Step D is greater than about 50%, greater than about 60%, greater than about 70%, greater than about 75%, greater than about 80%, greater than about 85%, greater than about 90%, greater than about 95%, or greater than about 99%. In certain embodiments, the yield of the isolated product of Step D is greater than about 70%, greater than about 75%, or greater than about 80%. In one embodiment, the purity of the isolated product of Step D is about 90% w/w, about 95% w/w, about 96% w/w, about 97% w/w, about 98% w/w, about 99% w/w, about 99.5% w/w, about 99.8% w/w, or about 99.9% w/w relative to the total batch. In one embodiment, the purity of the isolated product of Step D is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, or greater than about 99.9% w/w relative to the total batch.

In one embodiment, Step D is carried out under GMP conditions.

5. Step E

In one embodiment, the 5-tert-butylisoxazol-3-ylcarbamate derivative (X) of Step (E) is:

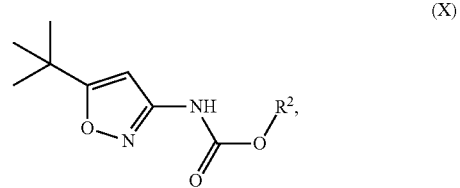

wherein $R^2$ is optionally substituted aryl, heteroaryl, alkyl, or cycloalkyl. In one embodiment, $R^2$ is optionally substituted with one or more halo, nitro, cyano, alkyl, or alkoxyl. In one embodiment, $R^2$ is optionally substituted alkyl, such as, e.g., methyl and ethyl. In one embodiment, $R^2$ is optionally substituted aryl or heteroaryl. In one embodiment, $R^2$ is aryl or heteroaryl optionally substituted with one or more halo, nitro, cyano, alkyl, or alkoxyl. In one embodiment, $R^2$ is unsubstituted aryl or heteroaryl. In one embodiment, $R^2$ is optionally substituted phenyl. In one embodiment, $R^2$ is phenyl optionally substituted with one or more electron withdrawing substituents. In one embodiment, $R^2$ is phenyl optionally substituted with one or more halo, nitro, or cyano. In one embodiment, $R^2$ is phenyl optionally substituted with one or more halo or nitro. In one embodiment, $R^2$ is nitrophenyl. In one embodiment, $R^2$ is phenyl. In one embodiment, the 5-tert-butylisoxazol-3-ylcarbamate derivative (X) is phenyl 5-tert-butylisoxazol-3-ylcarbamate, which is represented by the structure:

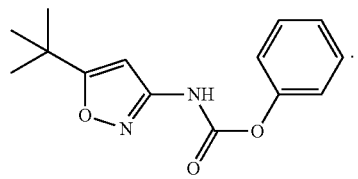 [SMILES: CC(C)(C)c1cc(NC(=O)Oc2ccccc2)no1]

In one embodiment provided herein is a compound of formula (X) wherein $R^2$ is defined herein elsewhere. In one embodiment, provided herein is phenyl 5-tert-butylisoxazol-3-ylcarbamate.

In one embodiment, 3-amino-5-tert-butyl isoxazole (IX), which is used in Step E as starting material, is obtained from a commercial supplier, such as, e.g., Sigma-Aldrich®, Inc., Matrix Scientific, Apollo Scientific, Ltd., Alfa Aesar, and Suzhou Yunan Pharmaceuticals & Intermediates Co., Ltd., China.

In one embodiment, the reaction of Step E is performed by stirring a mixture of compound (IX) and a suitable carbamate forming reagent in a suitable solvent at a suitable temperature until the reaction is substantially complete. In one embodiment, the reaction of Step E is carried out in the presence of a haloformate reagent. In one embodiment, the reaction of Step E is carried out in the presence of a chloroformate reagent, such as, e.g., phenyl chloroformate. In one embodiment, the reaction of Step E is carried out in the presence of base. In one embodiment, the reaction of Step E is carried out in the presence of both a haloformate reagent and a base. In one embodiment, the haloformate reagent is added to a stirred mixture of compound (IX) and the base in a suitable solvent, and the resulting mixture is stirred at a suitable temperature until the reaction is substantially complete.

In one embodiment, the reaction of Step E is carried out in the presence of a carbamate forming reagent known in the art. In one embodiment, the reaction of Step E is carried out in the presence of a haloformate reagent. In one embodiment, the reaction of Step E is carried out in the presence of a chloroformate reagent. In one embodiment, the reaction of Step E is carried out in the presence of phenyl chloroformate.

In one embodiment, the reaction of Step E is carried out in the presence of base. In one embodiment, the reaction of Step E is carried out in the presence of an organic or inorganic base. In one embodiment, the reaction of Step E is carried out in the presence of one or more carbonate or bicarbonate salts. In one embodiment, the reaction of Step E is carried out in the presence of potassium carbonate.

In one embodiment, the molar ratio of the carbamate forming reagent, such as, e.g., chloroformate, relative to compound (IX) used in the reaction of Step E is about 1.0 (i.e., [carbamate forming reagent]/[compound (IX)]=1.0), about 1.5, about 2.0, about 2.5, about 3.0, about 3.5, about 4.0, or about 5.0. In one embodiment, the molar ratio of the carbamate forming reagent, such as, e.g., chloroformate, relative to compound (IX) used in the reaction of Step E is about 1.0, about 1.1, about 1.2, about 1.3, about 1.4, or about 1.5. In one embodiment, the molar ratio of the carbamate forming reagent, such as, e.g., chloroformate, relative to compound (IX) used in the reaction of Step E is about 1.05.

In one embodiment, the molar ratio of the base used in the reaction of step E relative to compound (IX) is about 1.0 (i.e., [Base]/[compound (IX)]=1.0), about 1.5, about 2.0, about 2.5, about 3.0, about 3.5, about 4.0, or about 5.0. In one embodiment, the molar ratio of the base used in the reaction of Step E relative to compound (IX) is about 1.1, about 1.2, about 1.3, about 1.4, about 1.5, or greater than about 1.5. In one embodiment, the molar ratio of the base used in the reaction of Step E relative to compound (IX) is about 1.3.

In one embodiment, the reaction of Step E is carried out in a polar solvent. In one embodiment, the reaction of Step E is carried out in a non-polar solvent. In one embodiment, the reaction of Step E is carried out in an aprotic solvent. In one embodiment, the reaction of Step E is carried out in dichloromethane, ethyl acetate, tetrahydrofuran, acetone, methyl ethyl ketone, methyl t-butyl ether, acetonitrile, N-methylpyrrolidinone, or N,N-dimethylformamide, or the like. In one embodiment, the reaction of Step E is carried out in THF. In one embodiment, the reaction of Step E is carried out in anhydrous THF.

In one embodiment, the reaction of Step E is carried out at ambient temperature. In one embodiment, the reaction of Step E is carried out at elevated temperature. In one embodiment, the reaction of Step E is carried out at a temperature of about 0° C., about 10° C., about 20° C., about 30° C., about 40° C., about 50° C., or greater than about 50° C. In one embodiment, the reaction of Step E is carried out at a temperature of about 15° C., about 20° C., or about 25° C. In one embodiment, the reaction of Step E is carried out at a temperature of about 20° C.

The reaction time of the reaction of Step E can vary from about 1 hr to about 24 hr, depending on the reaction temperature, the reagents, and the equivalents and concentrations of reagents in the reaction mixture. In specific embodiments, the reaction time of Step E is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, or about 24 hr. In some embodiments, the reaction time is about 2 hr, about 3 hr, about 4 hr, about 5 hr, about 6 hr, about 7, about 8, or greater than about 8 hr, when the reaction is carried out in anhydrous THF with potassium carbonate used as the base and phenyl chloroformate used as the carbamate forming reagent, at a reaction temperature of about 20° C. In some embodiments, the reaction time is about 3 hr, about 4 hr, about 5 hr, or about 6 hr, when the reaction is carried out in anhydrous THF with potassium carbonate used as the base and phenyl chloroformate used as the carbamate forming reagent, at a reaction temperature of about 20° C. In some embodiments, the progress of the reaction is monitored, such as by taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that compound (IX) is present at a level of less than about 2% (i.e., % area by HPLC<2%) in the reaction mixture. In some embodiments, when the reaction is not substantially complete after about 6 hr at a temperature of about 20° C. in THF, additional base and carbamate forming reagent may be added to the reaction mixture to react with any remaining compound (IX).

In one embodiment, when the reaction of Step E is substantially complete, the reaction mixture is filtered to remove the inorganic salt, such as, e.g., the potassium salt. In one embodiment, the solid is washed with an organic solvent, such as, e.g., THF. In one embodiment, the filtrate is vacuum distilled. In one embodiment, the filtrate is vacuum distilled while maintaining the internal temperature at less than about 40° C. In one embodiment, the filtrate is concentrated by vacuum distillation to a reduced volume, without completely removing the solvent. In one embodiment, an anti-solvent, such as, e.g., water and/or ethanol, is added to the concentrated mixture containing product (X). In one embodiment, the mixture containing product (X) and anti-solvent is agitated for about 1 hr, about 2 hr, about 3 hr, about 4 hr, about 5 hr, or about 6 hr, at a temperature of about 20° C. In one embodiment, the product (X) of Step E precipitates from the mixture as a solid.

In one embodiment, the suspension containing the precipitated product (X) is filtered or centrifuged to separate the solid from the mixture. In one embodiment, the product (X) of Step E is collected by filtration or centrifuge in the presence of an anti-solvent, such as, e.g., a mixture of water and ethanol. In one embodiment, the product (X) of Step E is washed with a solvent, such as, e.g., water, during the filtration step. In one embodiment, the solid is dried on the filter. In one embodiment, the solid is blow-dried. In one embodiment, the solid is air-dried. In one embodiment, the solid is dried under vacuum. In one embodiment, the solid is dried in a vacuum oven. In one embodiment, the drying is carried out at ambient temperature. In one embodiment, the drying is carried out at a temperature of about 20° C., about 30° C., about 35° C., about 40° C., about 45° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr, or to a constant weight. In some embodiments, the isolated product of Step E may be further purified by re-crystallization.

In one embodiment, the yield of the isolated product of Step E is greater than about 70%, greater than about 80%, greater than about 90%, greater than about 95%, greater than about 98%, or greater than about 99%. In certain embodiments, the yield of the isolated product of Step E is greater than about 90%, greater than about 95%, or greater than about 98%. In one embodiment, the purity of the isolated product of Step E is about 90% w/w, about 95% w/w, about 96% w/w, about 97% w/w, about 98% w/w, about 99% w/w, about 99.5% w/w, about 99.8% w/w, or about 99.9% w/w relative to the total batch. In one embodiment, the purity of the isolated product of Step E is greater than about 90% w/w, greater than about 95% w/w, greater than about 96% w/w, greater than about 97% w/w, greater than about 98% w/w, greater than about 99% w/w, greater than about 99.5% w/w, greater than about 99.8% w/w, or greater than about 99.9% w/w relative to the total batch.

In one embodiment, Step E is carried out under GMP conditions.

6. Step F

In one embodiment, the 5-tert-butylisoxazol-3-ylcarbamate derivative (X) of Step (F) is:

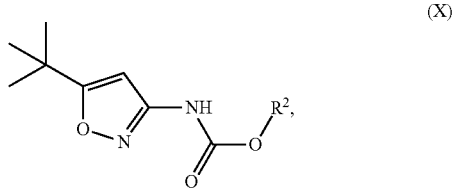

(X)

wherein $R^2$ is optionally substituted aryl, heteroaryl, alkyl, or cycloalkyl. In one embodiment, $R^2$ is optionally substituted with one or more halo, nitro, cyano, alkyl, or alkoxyl. In one embodiment, $R^2$ is optionally substituted aryl or heteroaryl. In one embodiment, $R^2$ is aryl or heteroaryl optionally substituted with one or more halo, nitro, cyano, alkyl, or alkoxyl. In one embodiment, $R^2$ is unsubstituted aryl or heteroaryl. In one embodiment, $R^2$ is optionally substituted phenyl. In one embodiment, $R^2$ is phenyl optionally substituted with one or more electron withdrawing substituents. In one embodiment, $R^2$ is phenyl optionally substituted with one or more halo, nitro, or cyano. In one embodiment, $R^2$ is phenyl optionally substituted with one or more halo or nitro. In one embodiment, $R^2$ is nitrophenyl. In one embodiment, $R^2$ is phenyl. In one embodiment, the 5-tert-butylisoxazol-3-ylcarbamate derivative (X) is phenyl 5-tert-butylisoxazol-3-ylcarbamate, which is represented by the structure:

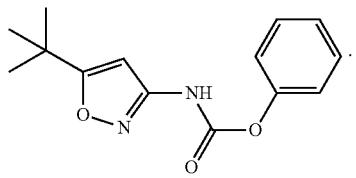 [SMILES: CC(C)(C)c1cc(NC(=O)Oc2ccccc2)no1]

In one embodiment, the reaction of Step F is performed by stirring a mixture of compound (VIII) and compound (X) in a suitable solvent at a suitable temperature until the reaction is substantially complete. In one embodiment, the reaction of Step F is carried out in the presence of base. In one embodiment, the reaction of Step F is carried out in the presence of a catalyst. In one embodiment, the reaction of Step F is carried out in the presence of both a base and a catalyst. In one embodiment, the base and/or catalyst is added to a stirred mixture of compound (VIII) and compound (X) in a suitable solvent, and the resulting mixture is stirred at a suitable temperature until the reaction is substantially complete. In one embodiment, the base is added to a stirred mixture of compound (VIII), compound (X), and the catalyst in a suitable solvent, and the resulting mixture is stirred at a suitable temperature until the reaction is substantially complete.

In one embodiment, the reaction of Step F is carried out in the presence of base. In one embodiment, the reaction of Step F is carried out in the presence of an organic or inorganic base. In one embodiment, the reaction of Step F is carried out in the presence of a tertiary amine, such as, e.g., triethylamine or diisopropylethylamine. In one embodiment, the reaction of Step F is carried out in the presence of triethylamine.

In one embodiment, the reaction of Step F is carried out in the presence of catalyst. In one embodiment, the reaction of Step F is carried out in the presence of 4-dimethylaminopyridine (DMAP).

In one embodiment, the molar ratio of compound (X) relative to compound (VIII) used in the reaction of Step F is about 0.8 (i.e., [Compound (X)]/[Compound (VIII)]=0.8), about 0.9, about 1.0, about 1.1, about 1.2, about 1.3, about 1.4, about 1.5, about 1.6, about 1.7, about 1.8, about 1.9, about 2.0, or greater than about 2.0. In one embodiment, the molar ratio of compound (X) relative to compound (VIII) used in the reaction of Step F is between about 1.0 and about 1.5. In one embodiment, the molar ratio of compound (X) relative to compound (VIII) used in the reaction of Step F is about 1.0, about 1.1, about 1.2, or about 1.3. In one embodiment, the molar ratio of compound (X) relative to compound (VIII) used in the reaction of Step F is about 1.0, about 1.1.

In one embodiment, the molar ratio of the base used in the reaction of Step F relative to compound (VIII) is about 0.1 (i.e., [Base]/[compound (VIII)]=0.1), about 0.2, about 0.3, about 0.4, about 0.5, about 0.6, about 0.7, about 0.8, about 0.9, about 1.0, or greater than about 1.0. In one embodiment, the molar ratio of the base used in the reaction of Step F relative to compound (VIII) is about 0.1 or about 0.2. In one embodiment, the molar ratio of the base used in the reaction of Step F relative to compound (VIII) is about 0.15.

In one embodiment, the molar ratio of the catalyst used in the reaction of Step F relative to compound (VIII) is about 0.1 (i.e., [Catalyst]/[compound (VIII)]=0.1), about 0.2, about 0.3, about 0.4, about 0.5, or greater than about 0.5. In one embodiment, the molar ratio of the catalyst used in the reaction of Step F relative to compound (VIII) is about 0.05, about 0.10, or about 0.15. In one embodiment, the molar ratio of the catalyst used in the reaction of Step F relative to compound (VIII) is about 0.06.

In one embodiment, the reaction of Step F is carried out in a polar solvent. In one embodiment, the reaction of Step F is carried out in a non-polar solvent. In one embodiment, the reaction of Step F is carried out in an aprotic solvent. In one embodiment, the reaction of Step F is carried out in dichloromethane, chloroform, carbon tetrachloride, 1,2-dichloroethane, chlorobenzene, ethyl acetate, tetrahydrofuran, acetone, methyl ethyl ketone, methyl t-butyl ether, acetonitrile, N-methylpyrrolidinone, or N,N-dimethylformamide, or the like. In one embodiment, the reaction of Step F is carried out in dichloromethane, chloroform, carbon tetrachloride, 1,2-dichloroethane, or chlorobenzene, or other halogenated hydrocarbon solvents. In one embodiment, the reaction of Step F is carried out in an anhydrous halogenated hydrocarbon solvent. In one embodiment, the reaction of Step F is carried out in dichloromethane, 1,2-dichloroethane, or chlorobenzene. In one embodiment, the reaction of Step F is carried out in dichloromethane. In one embodiment, the reaction of Step F is carried out in anhydrous dichloromethane.

In one embodiment, the reaction of Step F is carried out at ambient temperature. In one embodiment, the reaction of Step F is carried out at elevated temperature. In one embodiment, the reaction of Step F is carried out at a temperature of about 0° C., about 10° C., about 20° C., about 30° C., about 40° C., about 50° C., about 60° C., about 70° C., about 80° C., or greater than about 80° C. In one embodiment, the reaction of Step F is carried out at a temperature of about 40° C. In one embodiment, the reaction of Step F is carried out under a refluxing condition. In one embodiment, the reaction of Step F is carried out in dichloromethane under a refluxing condition.

The reaction time of the reaction of Step F can vary from about 1 hr to about 48 hr, depending on the reaction temperature, the reagents, and the equivalents and concentrations of reagents in the reaction mixture. In specific embodiments, the reaction time of Step F is about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 26 hr, about 28 hr, about 30 hr, about 32 hr, about 34 hr, about 36 hr, about 38 hr, about 40 hr, about 42 hr, about 44 hr, about 46 hr, or about 48 hr. In some embodiments, the reaction time is about 18 hr, about 20 hr, about 22 hr, about 24 hr, or about 30 hr, when the reaction is carried out in dichloromethane under a refluxing condition with triethylamine and DMAP used as the base and catalyst, respectively. In some embodiments, the progress of the reaction is monitored, such as by taking an aliquot of the reaction mixture, diluting it with a suitable solvent, and analyzing with HPLC. In one embodiment, the reaction is stopped when the reaction is determined to be substantially complete, e.g., via reaction progress monitoring. In one embodiment, the reaction is considered substantially complete when reaction progress monitoring by HPLC indicates that compound (VIII) is present at a level of less than about 1% relative to compound (I) (i.e., the ratio of % area by HPLC of compound (VIII) relative to compound (I)<1%) in the reaction mixture. In one embodiment, product (I) precipitates from the reaction mixture during the course of the reaction.

In one embodiment, when the reaction of Step F is substantially complete, the reaction mixture is cooled. In one embodiment, the reaction mixture is cooled to a temperature of about 0° C., about 10° C., about 20° C., or about 30° C. In one embodiment, the reaction mixture is cooled to a temperature of about 0° C. In one embodiment, the cooled reaction mixture is stirred for about 30 min, about 1.0 hr, about 1.5 hr, about 2.0 hr, about 2.5 hr, about 3.0 hr, or greater than 3.0 hr. In one embodiment, the cooled reaction mixture is stirred for at least about 2.0 hr. In one embodiment, the product (I) of Step F precipitates out of the mixture as a solid.

In one embodiment, the suspension containing the precipitated product (I) is filtered or centrifuged to separate the solid from the mixture. In one embodiment, the solid containing product (I) is washed with solvent, such as, e.g., cold dichloromethane. In one embodiment, the isolated solid is air-dried. In one embodiment, the isolated solid is blow-dried. In one embodiment, the isolated solid is dried under vacuum. In some embodiments, the solid is dried on the filter. In some embodiments, the solid is dried in a vacuum oven. In one embodiment, the drying is carried out at ambient temperature. In one embodiment, the drying is carried out at a temperature of about 20° C., about 30° C., about 35° C., about 40° C., about 45° C., or about 50° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr, or to a constant weight. In some embodiments, the isolated product of Step F may be further purified by re-crystallization.

In one embodiment, the yield of the isolated product of Step F is greater than about 70%, greater than about 80%, greater than about 85%, greater than about 90%, greater than about 95%, greater than about 98%, or greater than about 99%. In certain embodiments, the yield of the isolated product of Step F is greater than about 85% or greater than about 90%. In one embodiment, the purity of the isolated product of Step F is about 95% w/w, about 96% w/w, about 97% w/w, about 98% w/w, about 99% w/w, about 99.5% w/w, about 99.8% w/w, or about 99.9% w/w relative to the total batch. In one embodiment, the purity of the isolated product of Step F is greater than about 95% w/w, greater than about 96% w/w, greater than about 97% w/w, greater than about 98% w/w, greater than about 99% w/w, greater than about 99.5% w/w, greater than about 99.8% w/w, or greater than about 99.9% w/w relative to the total batch. In one embodiment, impurity (XI) is undetectable in the isolated product (I). In one embodiment, phenol is the major impurity in the isolated product (I), when phenyl chloroformate was used as the starting material. In one embodiment, the phenol impurity is present at a level of about 1% or less than about 1% relative to product (I) as indicated by HPLC analysis.

In one embodiment, Step F is carried out under GMP conditions.

7. Step G

In one embodiment, the free base of compound (I) is converted to an acid addition salt of compound (I). In one embodiment, the free base of compound (I) is converted to a hydrochloride salt of compound (I). In one embodiment, the free base of compound (I) is converted to a dihydrochloride salt of compound (I).

In one embodiment, the salt formation reaction of Step G is performed by adding a suitable acid to a stirred mixture of the free base of compound (I) in a suitable solvent at a suitable temperature, and the resulting mixture is stirred until the reaction is substantially complete.

In one embodiment, when a hydrochloric acid addition salt is formed, the salt formation reaction of Step G is carried out in the presence of aqueous hydrochloric acid. In one embodiment, the molar ratio of the acid used in Step G, e.g., hydrochloric acid, relative to compound (I) is about 1.0 (i.e., [Acid]/[Compound (I)]=1.0), about 1.5, about 2.0, about 2.5, about 3.0, about 3.5, about 4.0, or greater than about 4.0. In one embodiment, the molar ratio of the acid used in Step G, e.g., hydrochloric acid, relative to compound (I) is about 1.0, about 1.5, about 2.0, about 2.5, or about 3.0. In one embodiment, the molar ratio of the acid used in Step G relative to compound (I) is greater than about 2.0. In one embodiment, the molar ratio of the acid used in Step G relative to compound (I) is about 2.0, about 2.5, or about 3.0. In one embodiment, the molar ratio of the acid used in Step G relative to compound (I) is about 2.5.

In one embodiment, the salt formation reaction of Step G is carried out in a polar solvent. In one embodiment, the salt formation reaction of Step G is carried out in a protic solvent. In one embodiment, the salt formation reaction of Step G is carried out in ethyl acetate, tetrahydrofuran, acetone, methyl ethyl ketone, methyl t-butyl ether, acetonitrile, methanol, ethanol, isopropanol, or the like. In one embodiment, the salt formation reaction of Step G is carried out in alcohol, such as, e.g., methanol, ethanol, or isopropanol. In one embodiment, the salt formation reaction of Step G is carried out in methanol. In one embodiment, the salt formation reaction of Step G is carried out in anhydrous methanol.

In one embodiment, the reaction of Step G is carried out at ambient temperature. In one embodiment, the reaction of Step G is carried out at elevated temperature. In one embodiment, the reaction of Step G is carried out at a temperature of about 20° C., about 30° C., about 40° C., about 50° C., about 60° C., about 70° C., about 80° C., about 90° C., about 100° C., or greater than about 100° C. In one embodiment, the salt formation reaction of Step G is carried out under a refluxing condition. In one embodiment, the salt formation reaction of Step G is carried out in methanol under a refluxing condition. In one embodiment, the reaction of Step G is carried out at a temperature of about 65° C.

The reaction time of the reaction of Step G can vary from about 5 min to about 24 hr, depending on the reaction temperature, the reagents, and the equivalents and concentrations of reagents in the reaction mixture. In specific embodiments, the reaction time of Step G is about 5 min, about 15 min, about 30 min, about 1 hr, about 2 hr, about 4 hr, about 6 hr, about 8 hr, about 10 hr, about 12 hr, about 18 hr, or about 24 hr. In some embodiments, the reaction time is about 1 hr or about 2 hr, when the reaction is carried out in methanol under a refluxing condition. In one embodiment, the acid addition salt product precipitates from the reaction mixture during the course of the reaction.

In one embodiment, when the reaction of Step G is substantially complete, the reaction mixture is cooled. In one embodiment, the reaction mixture is cooled to a temperature of about 0° C., about 10° C., about 20° C., about 30° C., or about 40° C. In one embodiment, the reaction mixture is cooled to a temperature of about 20° C. In one embodiment, the acid addition salt product of Step G precipitates out of the mixture as a solid.

In one embodiment, the suspension containing the precipitated acid addition salt is filtered or centrifuged to separate the solid from the mixture. In one embodiment, the solid containing the acid addition salt is washed with solvent, such as, e.g., methanol. In one embodiment, the isolated solid is air-dried. In one embodiment, the isolated solid is blow-dried. In one embodiment, the isolated solid is dried under vacuum. In some embodiments, the solid is dried on the filter. In some embodiments, the solid is dried in a vacuum oven. In one embodiment, the drying is carried out at ambient temperature. In one embodiment, the drying is carried out at a temperature of about 20° C., about 30° C., about 35° C., about 40° C., about 45° C., about 50° C., about 55° C., or about 60° C., for a period of about 1 hr, about 2 hr, about 3 hr, about 4 hr, about 5 hr, about 6 hr, about 8 hr, about 10 hr, about 12 hr, about 14 hr, about 16 hr, about 18 hr, about 20 hr, about 22 hr, or about 24 hr, or to a constant weight. In some embodiments, the isolated product of Step G may be further purified by re-crystallization.

In one embodiment, the yield of the isolated product of Step G is greater than about 80%, greater than about 85%, greater than about 90%, greater than about 95%, greater than about 98%, or greater than about 99%. In certain embodiments, the yield of the isolated product of Step G is greater than about 85% or greater than about 90%. In one embodiment, the purity of the isolated product of Step G is about 95% w/w, about 96% w/w, about 97% w/w, about 98% w/w, about 99% w/w, about 99.5% w/w, about 99.9% w/w, about 99.95% w/w, or about 99.99% w/w relative to the total batch. In one embodiment, the purity of the isolated product of Step G is greater than about 95% w/w, greater than about 96% w/w, greater than about 97% w/w, greater than about 98% w/w, greater than about 99% w/w, greater than about 99.5% w/w, greater than about 99.9% w/w, greater than about 99.95% w/w, or greater than about 99.99% w/w relative to the total batch.

In one embodiment, Step G is carried out under GMP conditions.

Any and all combinations of the embodiments provided herein are encompassed by the present disclosure. Certain embodiments of the processes presented herein are illustrated by the following non-limiting examples.

VII. EXAMPLES

Certain embodiments of the processes presented herein are illustrated by the following non-limiting examples. Modifications of variables including, but not limited to, reaction solvents, reaction times, reaction temperatures, reagents, starting materials, and functional groups in the particular embodiments are also encompassed by the present disclosure.

In the examples below, unless otherwise indicated, all temperatures are set forth in degrees Celsius and all parts and percentages are by weight. Reagents may be purchased from commercial suppliers, such as, e.g., Sigma-Aldrich® Chemical Co., and may be used without further purification unless otherwise indicated. Reagents may also be prepared following standard literature procedures known to those skilled in the art. Solvents may be purchased, for example, from Sigma-Aldrich®, and may be used as received or may be purified using standard methods known to those skilled in the art, unless otherwise indicated.

Unless otherwise specified, the reactions set forth below were done generally at ambient temperature. Unless otherwise specified, reactions were assayed by HPLC, and terminated as judged by the consumption of starting material.

The compound structures and purities in the examples below were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, and/or HPLC. $^1$H NMR spectra were determined using an NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

Standard abbreviations and acronyms as defined in *J. Org. Chem.*, 2007, 72(1): 23A-24A are used herein. In some embodiments, exemplary abbreviations and acronyms used herein are as follows:

APCI—Atmospheric pressure chemical ionization
AR—Anhydrous
DCM—Dichloromethane
DSC—Differential scanning calorimetry
EA—Elemental analysis
eq—Equivalent(s)
IPC—In process control
KF—Karl-Fischer
LCMS—Liquid chromatography mass spectrometry
LOD—Loss on drying
psi—Pound per square inch
Raney Ni—Raney Nickel
RT—Room temperature
SM—Starting material
TBAI—Tetrabutylammonium iodide
TEA—Triethylamine
TGA—Thermal gravimetric analysis
XRPD—X-ray powder diffraction A. Preparation of 2-amino-6-hydroxybenzothiazole

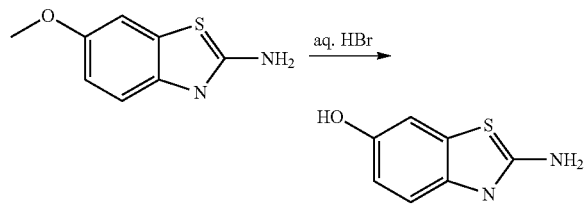

1. Example A-1

To a 1-L 3-necked round bottom flask fitted with a condenser, heating mantle, and mechanical stirrer was charged aqueous hydrobromic acid (48%, 632 mL, 5.6 mol, 10 equiv). 2-Amino-6-methoxybenzothiazole (100 g, 0.55 mol, 1 equiv) was added to the above flask over 15 minutes. The reaction temperature was raised slowly to reflux (105-110° C.). A clear dark brown colored solution was observed at about 80° C. The reflux was continued at 105-110° C. for about 4 hr. The progress of the reaction was monitored by HPLC. When 2-amino-6-methoxybenzothiazole was less than 2%, the reaction was substantially complete.

The reaction mass was cooled to 0-5° C. and at this point precipitation of a solid was observed. The mixture was maintained at 0-5° C. for 0.5 hr and filtered, and the cake was pressed to remove HBr. The wet cake was transferred to a 2-L round bottom flask fitted with a mechanical stirrer. Saturated aqueous sodium bicarbonate solution (~1500 mL) was added slowly at ambient temperature, whereupon considerable frothing was observed. The pH of the solution was found to be about 6.5 to 7. The mixture was stirred for 0.5 hr at ambient temperature and filtered. The filter cake was washed with water (500 mL), dried on the filter and then under vacuum at 30-35° C. for 10-12 hr to give the product 2-amino-6-hydroxybenzothiazole (82 g, 89% yield, HPLC purity=99%).

$^1$H NMR (DMSO-d$_6$, 500 MHz): δ 7.12 (d, 1H), 7.06 (S, 2H, NH$_2$), 7.01 (d, 1H), 6.64 (dd, 1H); MS (m/z)=167.1 [M$^+$+1].

TABLE

Summary of Plant Batches

| Batch No. | Input (kg) | Output (kg) | Remark |
|---|---|---|---|
| 1 | 10.00 | 7.58 | HPLC purity = 99.49%; 82.3% yield |
| 2 | 10.00 | 8.20 | HPLC purity = 99.15%; 89% yield |
| 3 | 10.00 | 7.90 | HPLC purity = 99.45%; 85.8% yield |
| Total | 30.00 | 23.68 | 85.59% Yield |

HPLC chromatographic conditions were as follows: The column used was XTerra RPB, 250×4.6 mm, 5μ or equivalent. Mobile Phase A was buffer, prepared by mixing 3.48 g of dipotassium hydrogen phosphate in 1.0 L of water, and adjusting the pH to 9.0 with phosphoric acid. Mobile Phase B was methanol. The flow rate was 1.0 mL/minute. Detection was set at UV 270 nm. The injection volume was 20 μL, and the sample was diluted with a diluent (Mobile Phase A:Mobile Phase B=70:30). Test solution was prepared by weighing accurately about 25 mg of sample and transferring it into a 100 mL volumetric flask, dissolving with 20-30 mL of diluent, making up the volume to the mark with diluent, and mixing. The HPLC was performed by separately injecting equal volumes of blank and test solution, and recording the chromatogram for all injections. The purity was calculated by area normalization method.

TABLE

HPLC Method

| Time (Minutes) | Mobile Phase A (% v/v) | Mobile Phase B (% v/v) |
|---|---|---|
| 0.01 | 70 | 30 |
| 10 | 70 | 30 |
| 15 | 30 | 70 |
| 20 | 20 | 80 |
| 30 | 10 | 90 |
| 35 | 10 | 90 |
| 45 | 20 | 80 |
| 50 | 70 | 30 |
| 55 | 70 | 30 |

2. Example A-2

2-Amino-6-methoxybenzothiazole was reacted with hot aqueous HBr at a temperature of >70° C. for about 3 hours and then the clear solution was cooled to ambient temperature overnight. The precipitated solids were collected, dissolved in hot water and the pH was adjusted to between 4.5-5.5. The resultant solids were collected, dried and re-crystallized from isopropanol. Second crop material was collected. The solids were vacuum dried to give 2-amino-6-hydroxybenzothiazole.

The reaction progress was monitored by thin layer chromatography (TLC). The product was isolated as a white solid, with 99.4% purity (HPLC area %). $^1$H NMR (300 MHz, DMSO-d$_6$) was collected, which conformed to structure.

3. Example A-3

A 22-L 3-neck round bottom flask was equipped with a mechanical agitator, thermocouple probe, a reflux condenser, and a heating mantle. The flask was charged with hydrobromic acid (14 L, 123.16 mol, 13.10 equiv). Heating was initiated and 2-amino-6-methoxybenzothiazole was added (1.7 kg, 9.4 mol, 1.00 equiv) over 10 minutes with stirring. The heating of the reaction mixture was continued to reflux, and maintained (>107° C.) for approximately 5 hours. The reaction mixture turned into a clear solution between 75° C. and 85° C. The reaction progress was monitored by TLC until no starting material was observed (A ~0.5 mL reaction mixture aliquot was diluted with ~0.5 mL water as a clear solution, neutralized with sodium acetate to pH ~5 and extracted with 1 mL dichloromethane. The organic layer was spotted: 5% methanol/dichloromethane; $R_f$ (product)=0.35; $R_f$ (starting material)=0.40).

The reaction mixture was cooled to ~20° C. (overnight). White solids precipitated. The solids were filtered on a polypropylene filter and pressed to remove as much hydrobromic acid from the solids as possible to facilitate the subsequent pH adjustment step. The slightly wet crude product was dissolved in hot (50° C.) water (5 L). The clear solution was filtered to remove any insoluble material present, and the solids were washed with 50° C. water. The filtrate was cooled to 10° C. The cooled filtrate was neutralized with sodium acetate (~1.0 kg) to pH 4.5 to 5.5 with vigorous stirring. A thick white solid precipitated. The solids were collected by filtration, and washed with cool (~10° C.) water (2×1.0 L) and air dried.

The wet crude product was slurried in hot (50° C.) isopropanol (3 L) briefly and allowed to stand in a cool room (~5° C.) overnight. The solids were collected by filtration and washed with methyl tert-butylether (2×500 mL). The solids were dried in a vacuum oven overnight (<30 mm Hg) at 30° C. (first crop). Yield: 1068 g (68%), white solid. HPLC: 99.4% (area). $^1$H NMR (300 MHz, DMSO-$d_6$) conformed to structure.

The organic filtrate was collected in a total volume of 1.0 L, cooled to 10° C. The off-white solids were precipitated and collected by filtration. The solids were dried in a vacuum oven overnight (<30 mm Hg) at 30° C. (second crop). Yield: 497 g (32%), off-white solid. HPLC: 99.8% (area).

The overall yield combining the first crop and the second crop was 1565 g, (99%).

B. Preparation of 2-(4-nitrophenyl)imidazo[2,1-b]benzothiazol-7-ol

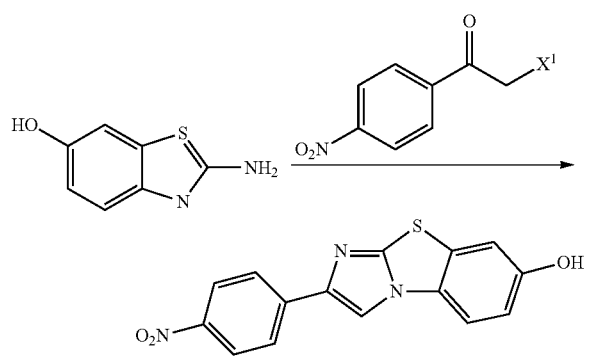

1. Example B-1

A 3-L 3-neck round bottom flask fitted with a condenser, a heating mantle, and a mechanical stirrer was charged with n-butanol (1.5 L), followed by 2-amino-6-hydroxybenzothiazole (75 g, 0.45 mol, 1.0 equiv), 2-bromo-4'-nitroacetophenone (121 g, 0.50 mol, 1.1 equiv), and sodium bicarbonate (41.6 g, 0.50 mol, 1.0 equiv). The reaction temperature was gradually raised to reflux and maintained at reflux (110-115° C.) for 2-3 hr. During the temperature increase, the reaction mass turned into a clear solution and then immediately changed into an orange colored suspension at 65-75° C. The progress of the reaction was monitored by HPLC analysis every 1 hr (reaction mass sample was submitted to QC). When the level of 2-amino-6-hydroxybenzothiazole was less than 2%, the reaction was substantially complete.

The reaction mass was slowly cooled to 50-60° C. and then further cooled to 0-5° C. and stirred for 15 min. The precipitated solids were collected by filtration, and dried on the filter. The wet cake was transferred in to a 1-L round bottom flask, and water (600 mL) was added. The suspension was stirred for 0.5 hr and filtered, and the solid was dried on the filter. The wet cake was again taken in to a 1-L round bottom flask and stirred with acetone (200 mL). The slurry was filtered and washed with acetone (2×100 mL), and the solid was dried on the filter, unloaded and further dried in a vacuum oven at ambient temperature to give the product 2-(4-nitrophenyl) imidazo[2,1-b]benzothiazol-7-ol (V) (120 g, 85.7% yield, HPLC purity=98.7%). $^1$H NMR (DMSO-$d_6$, 500 MHz): δ 9.96 (s, 1H, OH), 8.93 (s, 1H), 8.27 (d, 2H), 8.06 (d, 2H), 7.78 (d, 1H), 7.38 (d, 1H), 6.97 (dd, 1H); MS (m/z)=312 [M$^+$+1].

TABLE

Summary of Plant Batches

| Batch No | Input (kg)* | Output (kg) | Remark |
|---|---|---|---|
| 1 | 7.58 | 12.70 | LOD: 0.12%, Residue on ignition: 0.22%, Purity by HPLC: 99.27%; 89.4% yield. |
| 2 | 8.20 | 12.70 | LOD: 0.08%, Residue on ignition: 0.23%, Purity by HPLC: 99.24%; 83% yield. |
| 3 | 7.90 | 13.50 | LOD: 0.07%, Residue on ignition: 0.21%, Purity by HPLC: 99.41%; 91.8% yield. |
| Total | 23.68 | 38.90 | 87.68% Yield |

*Input of 2-amino-6-hydroxybenzothiazole (III)

HPLC chromatographic conditions were as follows: The column used was XTerra RPB, 250×4.6 mm, 5µ or equivalent. Mobile Phase A was buffer, prepared by mixing 3.48 g of dipotassium hydrogen phosphate in 1.0 L of water, and adjusting the pH to 9.0 with phosphoric acid. Mobile Phase B was methanol. The flow rate was 1.0 mL/minute. Detection was set at UV 235 nm. The injection volume was 10 µL. The blank was prepared by transferring 200 µL of DMSO and 200 µL of 2M NaOH into a 10 mL volumetric flask, making up the volume to the mark with methanol, and mixing. The test solution was prepared by weighing accurately about 10 mg of sample and transferring it into a 50 mL volumetric flask, dissolving with 1 mL of DMSO and 1 mL of 2M NaOH, sonicating to dissolve, making up the volume to the mark with methanol, and mixing. The HPLC was performed by separately injecting equal volumes of blank and test solution, and recording the chromatogram for all injections. The purity was calculated by area normalization method.

| TABLE | | |
|---|---|---|
| HPLC Method | | |
| Time (Minutes) | Mobile Phase A (% v/v) | Mobile Phase B (% v/v) |
| 0.01 | 70 | 30 |
| 10 | 70 | 30 |
| 15 | 30 | 70 |
| 20 | 20 | 80 |
| 30 | 10 | 90 | solids were dried in a vacuum oven (<10 mm Hg) at 40° C. Yield: 930 g (46%), yellow solid. HPLC: 99.5% (area). $^1$H NMR (300 MHz, DMSO-$d_6$) conformed to structure.

3. Example B-3

The reaction of Step B was carried out on multiple runs, varying solvents, temperature, and base. The results were summarized in the table below. The product (V) was isolated as yellow or green solids, with $^1$H NMR consistent with the structure and a purity of greater than about 98% by HPLC analysis.

| TABLE | | | | |
|---|---|---|---|---|
| Reaction Condition Screening | | | | |
| Batch No. | Input of Compound (III) (g) | Equivalents of Compound (IV) | Output of Compound (V) & % yield | Conditions |
| 1 | 6 | 1.0 | 2.7 g (24% yield) | 30 parts of n-butanol, reflux, 24 hr |
| 2 | 7 | 1.0 | 6.1 g (47% yield) | 20 parts of n-butanol, 0.01 eq of TBAI,* reflux, 24 hr |
| 3 | 0.5 | 1.3 | 0.85 g (90% yield) | 20 parts of n-butanol, 1.2 eq of NaHCO$_3$, reflux, 24 hr |
| 4 | 3 | 1.3 | 5.1 g (91% yield) | 20 parts of n-butanol, 1.2 eq of NaHCO$_3$, reflux, 24 hr |
| 5 | 3 | 1.1 | 4.7 g (83% yield) | 20 parts of n-butanol, 1.2 eq of NaHCO$_3$, reflux, 24 hr |
| 6 | 1 | 1.0 | 0.9 g (48% yield) | 30 parts of ethanol, reflux, 24 hr |
| 7 | 10 | 1.1 | 16.5 g (88% yield) | 20 parts of isopropanol, 1.2 eq of NaHCO$_3$, reflux, 24 hr |

*TBAI = Tetrabutylammonium Iodide

| TABLE-continued | | |
|---|---|---|
| HPLC Method | | |
| Time (Minutes) | Mobile Phase A (% v/v) | Mobile Phase B (% v/v) |
| 35 | 10 | 90 |
| 45 | 20 | 80 |
| 50 | 70 | 30 |
| 55 | 70 | 30 |

2. Example B-2

A 50-L 3-neck round bottom flask was equipped with a mechanical agitator, a thermocouple probe, a reflux condenser, and a heating mantle. The flask was charged with 2-amino-6-hydroxybenzothiazole (1068 g, 6.43 mol, 1.0 equiv) and ethanol (200 proof, 32.0 L), and the suspension was stirred for 10 minutes. 2-Bromo-4-nitroacetophenone (1667 g, 6.49 mol, 1.01 equiv) was added in one portion. The reaction mixture was heated to reflux (78° C.). The reflux was maintained for approximately 25 hours, resulting in a yellow suspension. The reaction progress was monitored by TLC (20% methanol/ethyl acetate; $R_f$(product)=0.85; $R_f$(starting material)=0.30). TLC indicated ~50% 2-amino-6-hydroxybenzothiazole after 24 hours of reflux. Tetrabutylammonium iodide (10 g) was added and reflux was maintained for an additional 12 hours. TLC indicated ~50% starting material still present. Coupling was seen to occur at both the thiazole and the amine.

The reaction mixture was cooled to 0-5° C. The solids were collected by filtration, and the yellow solid was washed with ethanol (200 proof, 2×1.0 L) and diethyl ether (2×1.5 L). The C. Preparation of 7-(2-morpholin-4-yl-ethoxy)-2-(4-nitrophenyl)imidazo[2,1-b]benzothiazole

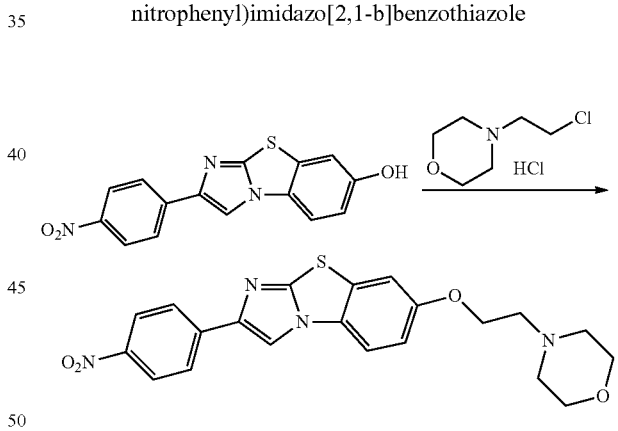

1. Example C-1

To a 2000-L glass-lined (GL) reactor was charged DMF (298 kg), and the agitator was started. Under a nitrogen blanket, the reactor was charged with 2-(4-nitrophenyl)imidazo[2,1-b]benzothiazol-7-ol (36.8 kg, 118.2 mol, 1.0 equiv), 4-(2-chloroethyl)morpholine hydrochloride (57.2-66.0 kg, 307.3-354.6 mol, 2.6-3.0 equiv), tetrabutylammonium iodide (8.7 kg, 23.6 mol, 0.2 equiv) and potassium carbonate (49.0 kg, 354.6 mol, 3.0 equiv). The resulting yellow suspension was heated and stirred at 90±5° C. for at least 15 minutes, then the temperature was increased to 110±5° C. The mixture was stirred for at least 1 hour and then sampled. The reaction was deemed complete if 2-(4-nitrophenyl)imidazo[2,1-b]benzothiazol-7-ol was <1% by HPLC. If the reaction was not complete, the heating was continued and the reaction sampled. If the reaction was incomplete after 6 hours, additional 4-(2-chloroethyl)morpholine hydrochloride may be charged. In general, additional charges of 4-(2-chloroethyl) morpholine hydrochloride had not been necessary at the given scale.

The reactor was cooled to 20±5° C. and charged with water (247 kg) and acetone (492 kg). The mixture was agitated at 20±5° C. for at least 1 hour. The product (VII) was isolated by filtration or centrifuge, and washed with water and acetone, and then dried in a vacuum oven at 45° C. to constant weight to give a yellow solid (46.2 kg, 92% yield, HPLC purity=97.4% by area). $^1$H NMR (300 MHz, DMSO-$d_6$) conformed to structure.

2. Example C-2

2-(4-Nitrophenyl)imidazo[2,1-b]benzothiazol-7-ol, 4-(2-chloroethyl)-morpholine hydrochloride, potassium carbonate, and tetrabutylammonium iodide were added to N,N-dimethylformamide forming a yellow suspension that was heated at a temperature of >50° C. for over 3 hours. The reaction was cooled and the solids were collected, slurried into water, filtered, slurried into acetone, filtered and washed with acetone to give yellow solids that were dried under vacuum to give 7-(2-morpholin-4-yl-ethoxy)-2-(4-nitrophenyl)imidazo[2,1-b]benzothiazole.

The reaction progress was monitored by thin layer chromatography (TLC). The product was isolated as a yellow solid, with 99% purity (HPLC area %), and a water content of 0.20%. Infrared (1R) spectrum was collected, which conformed to structure.

3. Example C-3

A 50-L 3-neck round bottom flask was equipped with a mechanical agitator, a thermocouple probe, a drying tube, a reflux condenser, and a heating mantle. The flask was charged with 2-(4-nitrophenyl)imidazo[2,1-b]benzothiazol-7-ol (1.770 kg, 5.69 mol, 1.0 equiv), N,N-dimethylformamide (18.0 L), 4-(2-chloroethyl)morpholine hydrochloride (2.751 kg, 14.78 mol, 2.6 equiv), potassium carbonate (2.360 kg, 17.10 mol, 3.0 equiv), and tetrabutylammonium iodide (0.130 kg, 0.36 mol, 0.06 equiv) with stirring. The resulting yellow suspension was heated to about 90° C. to 95° C., maintaining the temperature for approximately 5 hours. The reaction was monitored by TLC until no starting material was observed (20% methanol/ethyl acetate; $R_f$(product)=0.15; $R_f$ (starting material)=0.85).

The reaction mixture was cooled to ~10° C., and the yellow solids were collected by filtration on a polypropylene filter pad. The solids were slurried in water (2×5 L) and filtered. The crude wet product was slurried in acetone (5 L), filtered, and the solids were rinsed with acetone (2×1.5 L). The solids were dried in a vacuum oven (<10 mm Hg) at 45° C. Yield: 2.300 kg (95%), yellow solid. TLC: $R_f$=0.15 (20% methanol/ EtOAc). HPLC: 95.7% (area). $^1$H NMR (300 MHz, DMSO-$d_6$) conformed to the structure.

TABLE

Yields from multiple batch runs

| 2-(4-Nitro-phenyl) imidazo[2,1-b]benzo-thiazol-7-ol | 4-(2-Chloroethyl) morpholine hydrochloride | 7-(2-Morpholin-4-yl-ethoxy)-2-(4-nitro-phenyl)imidazo[2,1-b]benzothiazole | % Yield | HPLC (% Area) |
|---|---|---|---|---|
| 0.004 kg | 0.007 kg | 0.005 kg | 91% | 98.4% |
| 0.140 kg | 0.217 kg | 0.170 kg | 90% | 98.2% |
| 0.110 kg | 0.170 kg | 0.140 kg | 93% | 97.0% |
| 0.170 kg | 0.266 kg | 0.220 kg | 95% | NA |
| 0.930 kg | 1.446 kg | 1.220 kg | 96% | 98.8% |
| 1.770 kg | 2.751 kg | 2.300 kg | 95% | 95.7% |

4. Example C-4

To a reactor were added 2-(4-nitrophenyl)imidazo[2,1-b]benzothiazol-7-ol (1.0 kg), 4-(2-chloroethyl)morpholine hydrochloride (1.6 kg), tetrabutylammonium iodide (0.24 kg), and potassium carbonate (1.3 kg, anhydrous, extra fine, hydroscopic). N,N-Dimethylformamide (DMF) (8.6 L) was added into the reactor. The DMF used had water content of no more than 0.05% w/w. The mixture was stirred for between 15 and 30 minutes to render a homogeneous suspension, which was heated to between 85° C. and 95° C. and stirred at between 85° C. and 95° C. for 15 to 30 minutes. The mixture was then heated to between 105° C. and 120° C. and stirred at between 105° C. and 120° C. (e.g., 115° C.) until the reaction was complete (as determined by HPLC to monitor the consumption of starting material). In some embodiments, if necessary (e.g., if after 6 hours the reaction was not complete as indicated by HPLC analysis), additional 4-(2-chloroethyl) morpholine hydrochloride (0.03 kg) may be added and the reaction mixture stirred at between 105° C. and 120° C. (e.g., 115° C.) until reaction completion.

The reaction mixture was cooled to between 20° C. and 30° C. (e.g., over a period of 3 hours). To another reactor was added deionized water (7.6 L) and acetone (15 L). The mixture of water and acetone was then added into the reaction mixture while maintaining the temperature at between 20° C. and 30° C. The mixture was then stirred for 1 to 2 hours at a temperature of between 20° C. and 30° C. The mixture was filtered, and the solid was washed with deionized water (e.g., about 45× deionized water) until pH of washes was below 8. The solid was then washed with acetone (9.7 L). The solid was dried under vacuum at a temperature of less than 50° C. until the water content by Karl-Fischer was less than 0.30% w/w and TGA curve showed a mass loss of less than 0.30% w/w at about 229° C. (sampling approximately every 6 hours). The desired product was obtained in about 89% yield having about 99% purity by HPLC.

5. Example C-5

To a reactor were added 2-(4-nitrophenyl)imidazo[2,1-b]benzothiazol-7-ol (1.0 kg), 4-(2-chloroethyl)morpholine hydrochloride (1.6 kg), and potassium carbonate (1.3 kg, anhydrous, extra fine, hydroscopic). N,N-Dimethylformamide (DMF) (8.6 L) was added into the reactor. The DMF used had water content of no more than 0.05% w/w. The mixture was stirred for between 15 and 30 minutes to render a homogeneous suspension, which was heated to between 95° C. and 120° C. (e.g., between 100° C. and 105° C.) and stirred at between 95° C. and 120° C. (e.g., 105° C.) until the reaction was complete (as determined by HPLC to monitor the consumption of starting material). In some embodiments, if necessary (e.g., if after 6 hours the reaction was not complete as indicated by HPLC analysis), additional 4-(2-chloroethyl) morpholine hydrochloride (0.03 kg) and potassium carbonate (0.024 kg) may be added and the reaction mixture stirred at between 100° C. and 120° C. (e.g., 105° C.) until reaction completion.

The reaction mixture was cooled to between 60° C. and 70° C. over a period of at least 60 minutes. Industrial water (6 L) was added to the reactor. The reaction mixture was cooled to between 20° C. and 30° C. Acetone (6 L) was added to the reactor. The mixture was stirred for 1 to 2 hours at a temperature of between 20° C. and 30° C. The mixture was filtered, and the solid was washed with industrial water (e.g., about 45× industrial water) until pH of washes was below 8. The solid was then washed with acetone (9.7 L). The solid was dried under vacuum at a temperature of less than 50° C., until the water content by Karl-Fischer was less than 0.30% w/w and TGA curve showed a mass loss of less than 0.30% w/w at about 229° C. (sampling approximately every 6 hours).

6. Example C-6

To a reactor is added 2-(4-nitrophenyl)imidazo[2,1-b]benzothiazol-7-ol (1.0 kg), 4-(2-chloroethyl)morpholine hydrochloride (1.6 kg), and potassium carbonate (1.3 kg, anhydrous, extra fine, hydroscopic). N,N-Dimethylformamide (DMF) (8.6 L) is added into the reactor. The DMF has a water content of no more than 0.05% w/w. The mixture is stirred for between 15 and 30 minutes to render a homogeneous suspension, which is heated to between 95° C. and 120° C. (e.g., between 100° C. and 105° C.) and stirred at between 95° C. and 120° C. (e.g., 105° C.) until the reaction is complete (as determined by HPLC to monitor the consumption of starting material). In some embodiments, if necessary (e.g., if after 6 hours the reaction is not complete as indicated by HPLC analysis), additional 4-(2-chloroethyl)morpholine hydrochloride (0.03 kg) and potassium carbonate (0.024 kg) may be added and the reaction mixture stirred at between 100° C. and 120° C. (e.g., 105° C.) until reaction completion.

The reaction mixture is cooled to between 20° C. and 30° C. (e.g., over a period of 3 hours). To another reactor is added deionized water (7.6 L) and acetone (15 L). The mixture of water and acetone is then added into the reaction mixture while maintaining the temperature at between 20° C. and 30° C. The mixture is then stirred for 1 to 2 hours at a temperature of between 20° C. and 30° C. The mixture is filtered, and the solid is washed with deionized water (e.g., about 45× deionized water) until pH of washes is below 8. The solid is then washed with acetone (9.7 L). The solid is dried under vacuum at a temperature of less than 50° C. until the water content by Karl-Fischer is less than 0.30% w/w and TGA curve shows a mass loss of less than 0.30% w/w at about 229° C. (sampling approximately every 6 hours).

D. Preparation of 7-(2-morpholin-4-yl-ethoxy)-2-(4-aminophenyl)imidazo[2,1-b]benzothiazole

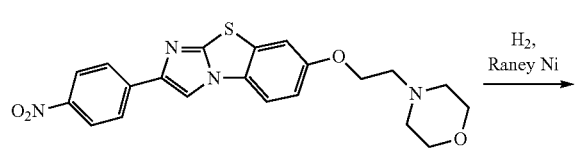

1. Example D-1

To a 200-L high pressure (HP) reactor was charged a slurry of 7-(2-morpholin-4-yl-ethoxy)-2-(4-nitrophenyl)imidazo[2,1-b]benzothiazole (VII) (7.50 kg, 17.7 mol, 1.0 equiv) in methanol (30 kg). The container was rinsed with additional methanol (10 kg) and the rinse was charged to the reactor. The reactor was then charged with THF (67 kg) and methanol (19 kg). The contents were agitated and the reactor was flushed with nitrogen by alternating nitrogen and vacuum. Vacuum was applied to the reactor and Raney Ni catalyst (1.65 kg, 0.18 wt. equiv) was charged through a sample line. Water (1 kg) was charged through the sample line to rinse the line. The reactor was flushed with nitrogen by alternating nitrogen and vacuum. The reactor was then vented and heated to 50° C. The reactor was closed and pressurized with hydrogen gas to 15 psi keeping the internal temperature below 55° C. The reactor was vented and re-pressurized a total of 5 times, then pressurized to 150 psi with hydrogen gas. The contents were agitated at 50° C. for at least 4 hours. At this point a hydrogen uptake test was applied: The reactor was re-pressurized to 150 psi and checked after 1 hour. If a pressure drop of more than 5 psi was observed, the process was repeated. Once the pressure drop remained <5 psi, the reactor was vented and sampled. The reaction was deemed complete when 7-(2-morpholin-4-yl-ethoxy)-2-(4-nitrophenyl)imidazo[2,1-b]benzothiazole (VII) was ≤0.5% by HPLC.

The reactor was flushed with nitrogen as shown above. The 200-L HP reactor was connected to the 2000-L GL reactor passing through a bag filter and polish filter. The bag filter and polish filter were heated with steam. The 200-L HP reactor was pressurized (3 psi nitrogen) and its contents were filtered into the 2000-L reactor. The filtrates were hot. The 200-L reactor was vented and charged with THF (67 kg) and methanol (59 kg), the reactor agitated, and filtered into the 2000-L GL reactor.

A total of 6 reductions (46.2 kg processed) were carried out and the combined batches were concentrated by vacuum distillation (without exceeding an internal temperature of 40° C.) to a volume of ~180 L. The reactor was cooled to 20° C. and charged with heptane (250 kg) and again vacuum distilled to a volume of ~180 L. The reactor was charged with heptane (314 kg) and agitated at 20° C. for at least 1 hour, and then the product was isolated by centrifugation or collection on a Nutsche filter, washing with heptanes (2-5 kg per portion for centrifugation, followed by a 10-20 kg heptanes rinse of the reactor; or 94 kg for Nutsche filtration, rinsing the reactor first). The cake was blown dry, transferred to a vacuum oven and dried to constant weight maintaining a temperature≤50° C. to give the desired product (VIII) (34.45 kg, 80% yield, HPLC purity=97.9%).

2. Example D-2

7-(2-Morpholin-4-yl-ethoxy)-2-(4-nitrophenyl)imidazo[2,1-b]benzothiazole was dissolved into methanol and THF and placed in a hydrogenator. Raney nickel was added and the vessel was pressurized with hydrogen and stirred for >24 hours. The reaction mixture was concentrated to a thick paste and diluted with methyl tert-butyl ether. The resulting solids were filtered and washed with methyl tert-butyl ether and dried under vacuum to give 7-(2-morpholin-4-yl-ethoxy)-2-(4-aminophenyl) imidazo[2,1-b]benzothiazole.

The reaction progress was monitored by thin layer chromatography (TLC). The product was isolated as a yellow solid, with 99% purity (HPLC area %). IR was collected, which conformed to structure.

3. Example D-3

Into a 5-gallon autoclave, 7-(2-morpholin-4-yl-ethoxy)-2-(4-nitrophenyl) imidazo[2,1-b]benzothiazole (580 g, 1.37 mol, 1.0 equiv), THF (7.5 L), methanol (7.5 L, AR) and ~55 g of decanted Raney nickel catalyst were added. The reaction vessel was purged with nitrogen (3×50 psi) and hydrogen (2×50 psi), with stirring briefly under pressure and then venting. The autoclave was pressurized with hydrogen (150 psi). The mixture was stirred and the hydrogen pressure was maintained at 150 psi for over 24 hours with repressurization as necessary. The reaction progress was monitored by TLC (10% methanol/chloroform with 1 drop ammonium hydroxide; $R_f$(product) 0.20; $R_f$(SM) 0.80). The reaction was substantially complete when the TLC indicated no starting material present, typically after 24 hours of stirring at 150 psi. The hydrogenation was continued at 150 psi for a minimum of 4 hours or until completion if starting material was still present after the initial 4 hours.

The reaction mixture was filtered through a Buchner funnel equipped with a glass fiber filter topped with a paper filter. Unreacted starting material was removed together with the catalyst. The filtrate was concentrated to a total volume of 0.5 L, and the residue was triturated with methyl tert-butyl ether (0.5 L). The resultant solids were collected by filtration, and washed with methyl tert-butyl ether (0.3 L) (first crop).

The filtrate was concentrated to dryness and the residue was diluted with methyl tert-butyl ether (2 L). The resultant solids were collected by filtration, washing with methyl tert-butyl ether (0.5 L) (second crop).

The solids were dried in a vacuum oven (<10 mm Hg) at 25° C. Yield: 510 g (95%), beige solid. TLC: $R_f$ 0.2 (10% methanol/chloroform with one drop of ammonium hydroxide). HPLC: 99.0% (area). $^1$H NMR (300 MHz, DMSO-$d_6$) conformed to the structure.

TABLE

Yields from multiple batch runs

| 7-(2-Morpholin-4-yl-ethoxy)-2-(4-nitro-phenyl)imidazo [2,1-b]benzothiazole | Raney Ni | 7-(2-Morpholin-4-yl-ethoxy)-2-(4-amino-phenyl)imidazo [2,1-b]benzothiazole | % Yield | HPLC (% Area) |
|---|---|---|---|---|
| 0.580 kg | ~55 g | 0.510 kg | 95% | 99.0% |
| 0.446 kg | ~50 g | 0.446 kg | 96% | 99.2% |
| 0.550 kg | ~55 g | 0.970 kg | 95% | 99.0% |
| 0.550 kg | ~55 g | | | |
| 0.550 kg | ~55 g | 1.030 kg | 95% | 98.8% |
| 0.550 kg | ~55 g | | | |

4. Example D-4

The reaction of Step D was carried out in multiple runs under various conditions, such as, e.g., varying catalyst loading, concentration of reactant, reaction temperature, and/or workup procedures. The results are summarized in the table below.

| Description | Run # 1 | Run # 2 | Run # 3 | Run # 4 | Run # 5 |
|---|---|---|---|---|---|
| Compound (VII) | 2.3 g (1.0 eq) | 5.0 g (1.0 eq) | 5.0 g (1.0 eq) | 5.0 g (1.0 eq) | 5.0 g (1.0 eq) |
| Raney Nickel (slurry) | 0.22 g (0.095 wt) | 0.47 g (0.095 wt) | 0.9 g (0.18 wt) | 0.9 g (0.18 wt) | 0.9 g (0.18 wt) |
| Methanol | 30 mL | 25 mL (5 vol) | 25 mL (5 vol) | 25 mL (5 vol) | 25 mL (5 vol) |
| THF | 30 mL | 25 mL (5 vol) | 25 mL (5 vol) | 25 mL (5 vol) | 25 mL (5 vol) |
| Hydrogen | 150 PSI | 150 PSI | 150 PSI | 150 PSI | 150 PSI |
| Rxn Temp (° C.) | RT | RT | RT | RT | RT |
| Rxn Time (Hr) | 24 hr | 24 hr | 24 hr | 24 hr | 24 hr |
| Work Up | Filtered the solution through celite, concentrated, solvent exchanged with heptane, stirred the solids and filtered washed with heptane | Filtered the solution through celite, concentrated, solvent exchanged with heptane, stirred the solids and filtered washed with heptane | Filtered the solution through celite, concentrated, solvent exchanged with heptane, stirred the solids and filtered washed with heptane | Filtered the solution through celite, washed with THF, concentrated, solvent exchanged with heptane, stirred the solids and filtered washed with heptane | Filtered the solution through celite. The celite filter cake refluxed in THF washed with hot THF, concentrated, solvent exchanged with heptane, stirred the solids and filtered washed with heptane |
| Produce (VIII) | 1.9 g | 3.88 g | 1.11 g | 2.6 g | 4.4 g |
| Yield | 88% | 83.4% | | 56 | 94.6% |
| HPLC purity | 95.6% | 77.5% | | 91% | 93.8% |

| Description | Run # 6 | Run # 7 | Run # 8 |
|---|---|---|---|
| Compound (VII) | 5.0 g (1.0 eq) | 75.0 g (1.0 eq) | 1398 g (4 × 282 g) (1 × 270 g) |

| | | | |
|---|---|---|---|
| Raney Nickel (slurry) | 0.9 g (0.18 wt) | 13.5 g (0.18 wt) | 50.76 g for 4expts<br>48.69 g for 1 expt |
| Methanol | 25 mL (5 vol) | 750 mL (10 vol) | 2820 mL 10 vol for 4expts<br>2705 mL 10 vol for 1expt |
| THF | 25 mL (5 vol) | 750 mL (10 vol) | 2820 mL 10 vol for 4expts<br>2705 mL 10 vol for 1expt |
| Hydrogen | 150 PSI | 150 PSI | 150 PSI |
| Rxn Temp (° C.) | 50° C. | 50° C. | 50° C. |
| Rxn Time (Hr) | 24 hr | 24 hr | 24 hr |
| Work Up | Filtered the hot solution through celite. Washed the celite filter cake with hot 50 mL MeOH/THF, filtrate concentrated, solvent exchanged with heptane, stirred the solids and filtered washed with heptane | Filtered the hot solution through celite. Washed the celite filter cake with hot 2 × 750 mL MeOH/ THF, | Filtered the hot solution through celite. Washed the celite filter cake with hot 2 × 10 vol mL MeOH/THF, |
| Product (VIII) | 2.8 g | 67.9 g | 1235.8 g |
| Yield | 60% | 97.4% | 95.1% |
| HPLC purity | 99% | 96.7% | 98.3% |

5. Example D-5

To a pressure reactor under nitrogen atmosphere was added a slurry of Raney Nickel in water (0.22 kg) (e.g. about 0.14 kg dry catalyst in water) and the charging line was rinsed with deionized water (0.13 L). To another reactor (Reactor B) were added methanol (5.05 L) and 7-(2-morpholin-4-yl-ethoxy)-2-(4-nitrophenyl)imidazo[2,1-b]benzothiazole (1.0 kg), and the mixture was stirred for between 15 and 30 minutes to render a homogenous suspension. The suspension was transferred to the pressure reactor. Reactor B was washed with methanol (4.88 L) and the wash was transferred to the pressure reactor. Tetrahydrofuran (10.1 L) was added to the pressure reactor. Hydrogen was charged to the pressure reactor to a pressure of between 2.0 bar and 3.0 bar. The reactor was heated to a temperature of between 45° C. and 55° C. Hydrogen was then charged to the pressure reactor to a pressure of between 6.0 bar and 7.0 bar. The mixture was stirred at a temperature of between 45° C. and 55° C. (e.g., 50° C.), while maintaining the hydrogen pressure between 6.0 bar and 7.0 bar until reaction completion (as determined by HPLC to monitor the consumption of starting material).

The mixture was filtered while maintaining the temperature at between 35° C. and 50° C. The pressure reactor and the filter were washed with a mixture of THF (10.1 L) and methanol (9.93 L) preheated to a temperature of between 45° C. and 55° C. (e.g., 50° C.). The combined filtrate was concentrated to a volume of between 2.4 L and 2.8 L under vacuum at a temperature of no more than 40° C., and a precipitate was formed. Methanol (7.5 L) was added. The slurry was cooled to a temperature of between 5° C. and −5° C. (e.g., over 3 hours) and stirred for at least 1 hour (e.g., for 3 hours) while maintaining the temperature at between 5° C. and −5° C. The suspension was filtered. The solid was washed with methanol (2×1.2 L). The solid was then dried under vacuum at a temperature of less than 50° C. until the methanol and THF contents were each less than 3000 ppm as analyzed by GC (e.g., less than 1500 ppm). The desired product was obtained in about 88.5% yield having about 99% purity by HPLC.

E. Preparation of phenyl 5-tert-butylisoxazol-3-ylcarbamate

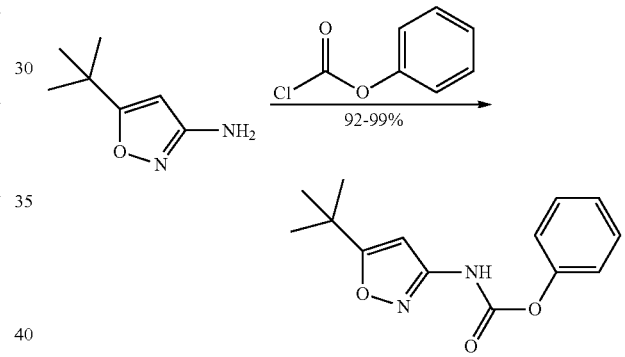

The jacket temperature of a 200-L glass-lined (GL) reactor was set to 20° C. To the reactor was charged 5-tert-butylisoxazole-3-amine (15.0 kg, 107.0 mol, 1.0 equiv), then $K_2CO_3$ (19.5 kg, 141.2 mol, 1.3 equiv) and anhydrous THF (62 kg). Agitation was started and then phenyl chloroformate (17.6 kg, 112.4 mol, 1.05 equiv) was charged. The charging line was rinsed with additional anhydrous THF (5 kg). The reaction was agitated at 20±5° C. for at least 3 hours then sampled. The reaction was deemed complete if 5-tert-butylisoxazole-3-amine was ≤2% by HPLC. If the reaction was not complete after 6 hours, additional $K_2CO_3$ and phenyl chloroformate may be added to drive the reaction to completion.

Once complete, the reaction was filtered (Nutsche). The filter was rinsed with THF (80 kg). The filtrate was vacuum distilled without exceeding an internal temperature of 40° C. until ~50 L remained Water (188 kg) and ethanol (45 L) were charged, and the mixture was agitated for at least 3 hours with a jacket temperature of 20° C. The resulting solid was isolated by centrifugation or collection on a Nutsche filter, rinsed with water (2-5 kg for each centrifugation portion; 30 kg for Nutsche filtration) and blow-dried. The solid was then dried to constant weight in a vacuum oven (45° C.) to give the desired product (19.4 kg, 92% yield, HPLC purity=97.4%). On an 800 g scale, 1559 g of the desired product (98% yield) was obtained with a 99.9% HPLC purity. $^1$H NMR (DMSO-d$_6$) δ 11.17 (s, 1H); 7.4 (m, 2H); 7.2 (m, 3H); 1.2 (s, 9H). LCMS (M+H)$^+$261.

F. Preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea

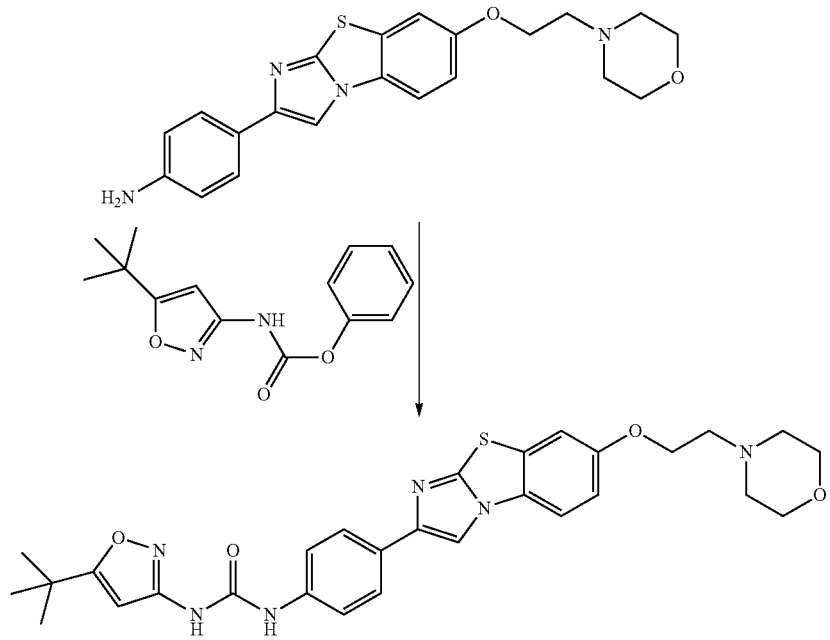

1. Example F-1

The jacket of a 2000-L GL reactor was set to 20° C. and the reactor was charged with 7-(2-morpholin-4-yl-ethoxy)-2-(4-aminophenyl)imidazo[2,1-b]benzothiazole (26.7 kg, 67.8 mol, 1.0 equiv), 3-amino-5-t-butylisoxazole phenyl carbamate (19.4 kg, 74.5 mol, 1.1 equiv), DMAP (0.5 kg, 4.4 mol, 0.06 equiv), and DCM (anhydrous, 260 kg). Agitation was started, triethylamine (1.0 kg, 10.2 mol, 0.15 equiv) was charged followed by additional DCM (5 kg) through the charging line. The reaction was heated to reflux (~40° C.) and agitated for at least 20 hours with complete dissolution observed followed by product crystallizing from solution after ~30 minutes. The reaction was sampled and deemed complete when HPLC analysis showed a ratio of compound (VIII) to compound (I)≤1%.

The reactor was cooled to 0° C. and stirred for at least 2 hours. The content of the reactor were isolated by centrifuge. Each portion was rinsed with 2-3 kg of cold (0° C.) DCM and spun dry for at least 5 minutes with a 10 psi nitrogen purge. For the final portion, the reactor was rinsed with 10 kg of cold (0° C.) DCM and transferred to the centrifuge where it was spun dry for at least 5 minutes with a 10 psi nitrogen purge. The combined filter cakes were transferred to a vacuum tray dryer and dried to constant weight at 50° C. and at least >20 inches of Hg to give the desired product (I) (35.05 kg, 92% yield, HPLC purity=98.8%). Phenol was the major impurity detected (0.99%); and three other impurities (<0.10%) were detected. $^1$H NMR (300 MHz, DMSO-d$_6$) conformed to structure.

2. Example F-2

A variety of solvents were used in the reaction of Step F to optimize for better yields and purity profiles. The contents of the symmetrical urea impurity (XI) were compared and summarized in the table below:

| Solvent used in the Reaction of Step F | Reaction Yield | Purity of Compound (I) HPLC % Area | Symmetrical Urea Impurity HPLC % Area |
|---|---|---|---|
| THF | 96.2% | 92.4% | 5.5% |
| Toluene | 85% | 96.9% | 0.28% |
| MTBE | 85% | 93.8% | 6.2% |
| THF/DCM (1:1) | N/A | 89.0% | 0.55% |
| DCM | 85.5% | 98.2% | 0% |

3. Example F-3

The reaction of Step F was carried out in multiple runs under various conditions, such as, e.g., varying reaction conditions, e.g., reaction temperature, reaction time, equivalents of reagents used, solvent, and/or workup procedures. The results were summarized in the table below. Runs 1-8 were carried out in THF as the solvent. Various work-up conditions were evaluated in Runs 1-4. Varying equivalents of 3-amino-5-t-butylisoxazole phenyl carbamate were used in Runs 5-8, in order to minimize the formation of the symmetrical urea impurity (XI). Runs 9-12 were performed to evaluate reaction under acidic conditions. Various solvents were used in Runs 13-17 to optimize yield and purity of the desired product and minimize the formation of the symmetrical urea impurity (XI). Runs 18-22 were performed in DCM.

| Description | Run # 1 | Run # 2 | Run # 3 | Run # 4 |
|---|---|---|---|---|
| Compound (VIII) | 1.5 g (1.0 eq) | 2.0 g (1.0 eq) | 4.0 g (1.0 eq) | 65.0 g (1.0 eq) |
| 3-amino-5-t-butylisoxazole phenyl carbamate | 0.99 g (1.0 eq) | 1.32 g (1.0 eq) | 2.64 g (1.0 eq) | 42.9 g (1.0 eq) |
| DMAP | 30 mg (0.06 eq) | 40 mg (0.06 eq) | 80 mg (0.06 eq) | 1.3 g (0.06 eq) |
| TEA | 60 μL (0.15 eq) | 80 μL (0.15 eq) | 150 μL (0.15 eq) | 3.38 mL (0.15 eq) |
| THF | 19 mL | 25 mL | 50 mL | 820 mL |
| Rxn Temp (° C.) | 60 | 60 | 60 | 60 |
| Rxn Time (Hr) | 18 | 18 | 18 | 28 |
| Work Up | Cooled to RT, filtered the solids, washed with heptane, solids obtained as first crop; THF filtrate triturated with heptane, filtered the solids as second crop | Cooled in ice bath, filtered the solids, washed with heptane | Reaction mixture was concentrated to 20 g and 20 mL of heptane added and triturated for 1 hr. Filtered the solids and washed with heptane | Reaction mixture was concentrated to 250 g and 400 mL of heptane added and triturated for 1 hr. Filtered the solids and washed with heptane |
| Compound (I) | 1.8 g First Crop: 1.2 g Second Crop: 0.6 g | 1.86 g | 5.4 g | 92.3 g |
| Yield | 84.5% | 65.5% | 94.7% | 99% |
| HPLC purity | First crop: 98.5% Second crop: 95% | 99.3% | 98.1% | 89.6% |

| Description | Run # 5 | Run # 6 | Run # 7 | Run # 8 |
|---|---|---|---|---|
| Compound (VIII) | 5.0 g (1.0 eq) | 3.0 g (1.0 eq) | 3.0 g (1.0 eq) | 3.0 g (1.0 eq) |
| 3-amino-5-t-butylisoxazole phenyl carbamate | 3.3 g (1.0 eq) | 2.02 g (1.02 eq) | 2.08 g (1.05 eq) | 2.18 g (1.10 eq) |
| DMAP | 100 mg (0.06 eq) | 60 mg (0.06 eq) | 60 mg (0.06 eq) | 60 mg (0.06 eq) |
| TEA | 190 μL (0.15 eq) | 160 μL (0.15 eq) | 160 μL (0.15 eq) | 160 μL (0.15 eq) |
| THF | 63 mL | 38 mL (12.6 vol) | 38 mL (12.6 vol) | 38 mL (12.6 vol) |
| Rxn Temp (° C.) | 60 | 60 | 60 | 60 |
| Rxn Time (Hr) |  | 23.5 h | 23.5 h | 5 h |
| Work Up | Concentrated to 24 g, triturated slurry at RT with 30 mL heptane (6 vol) for 23 h, filtered, washed with 6 vol heptane | Cooled to 0° C., filtered, washed with 6 vol ice-cold THF, dried under vacuum at 45° C. | Cooled to 0° C., filtered, washed with 6 vol ice-cold THF, dried under vacuum at 45° C. | Reaction mixture split into 2 portions of 20.7 g each. Portion 1 cooled to 0° C., filtered and washed with ice-cold THF. Portion 2 concentrated to 11 g, filtered and washed with THF. Both solids dried under vacuum at 45° C. |
| Yield | 96.22% | 72.11% | 68.92% | Portion 1 = 56.95% Portion 2 = 65.68% |
| Amt of impurity at RT = 7.0 and 21.5 min | 7.0 min = 5.53% 21.5 min = 0% | 7.0 min = 4.49% 21.5 min = 0.34% | 7.0 min = 6.48% 21.5 min = 0% | P1 7.0 min = 5.31% 21.5 min = 0% P2 7.0 min = 5.33% 21.5 min = 0% |
| HPLC purity | 92.40% | 94.32% | 92.57% | Portion 1 = 93.50% Portion 2 = 93.72% |

| Description | Run # 9 | Run # 10 | Run # 11 | Run # 12 |
|---|---|---|---|---|
| Compound (VIII) | 3.0 g (1.0 eq) | 3.0 g (1.0 eq) | 3.0 g (1.0 eq) | 3.0 g (1.0 eq) |
| 3-amino-5-t-butylisoxazole phenyl carbamate | 2.18 g (1.10 eq) | 2.18 g (1.10 eq) | 2.18 g (1.10 eq) | 2.18 g (1.10 eq) |
| 4M HCl in Dioxane (Reaction under acidic conditions) | 1920 μL (1.01 eq) | 1920 μL (1.01 eq) | 1920 μL (1.01 eq) | 1920 μL (1.01 eq) |
| Solvent | THF, 38 mL (12.6 vol) | Chlorobenzene, 38 mL (12.6 vol) | Toluene, 38 mL (12.6 vol) | Toluene, 38 mL (12.6 vol) |
| Rxn Temp (° C.) | 60 | 60 | 60 | 60 |
| Rxn Time (Hr) | 21 h | 21 h | 21 h | 21 h |
| Work Up | Reaction mixture discarded | Reaction mixture discarded | Reaction mixture discarded | Reaction mixture discarded |
| Amt of impurity at RT = 7.0 and 21.5 min | NA | NA | NA | NA |
| HPLC purity | 3.39% | 4.43% | 1.61% | 3.50% |

| Description | Run # 13 | Run # 14 | Run # 15 | Run # 16 |
|---|---|---|---|---|
| Compound (VIII) | 3.0 g (1.0 eq) | 3.0 g (1.0 eq) | 3.0 g (1.0 eq) | 5.0 g (1.0 eq) |
| 3-amino-5-t-butylisoxazole phenyl carbamate | 2.18 g (1.10 eq) | 2.18 g (1.10 eq) | 2.18 g (1.10 eq) | 3.63 g (1.10 eq) |

-continued

| | | | | |
|---|---|---|---|---|
| DMAP | 60 mg (0.06 eq) | 60 mg (0.06 eq) | 60 mg (0.06 eq) | 100 mg (0.06 eq) |
| TEA | 160 µL (0.15 eq) | 160 µL (0.15 eq) | 160 µL (0.15eq) | 177 µL (1.0 eq) |
| Solvent | 30 mL (10 vol)<br>1 = Toluene<br>2 = DCM<br>3 = MTBE | 30 mL (10 vol)<br>1 = Toluene<br>2 = DCM | 30 mL (10 vol)<br>1:1 THF:DCM | 50 mL (10 vol) DCM |
| Rxn Temp (° C.) | 1 = 60<br>2 = 30<br>3 = 40 | 1 = 100<br>2 = 40 | 55 | 40 |
| Rxn Time (Hr) | 1 = 21 h<br>2 = 21 h<br>3 = 21 h | 1 = 17 h<br>2 = 21.5 h | 4.5 h | 17 h |
| Work Up | 1 = Cooled to 0° C., filtered, washed with ice-cold toluene<br>2 = Concentrated to 18 g, charged 3 vol heptane, stirred at 0° C. for 1 h, filtered, washed with ice-cold heptane<br>3 = Cooled to 0° C., filtered, washed with ice-cold MTBE. Solids dried at 45° C. | 1 = 17 h IPC showed 2.92% symmetrical urea, reaction mixture was discarded<br>2 = Cooled to 0° C., filtered, washed with ice-cold DCM, dried under vacuum at 45° C. | Reaction mixture discarded, detected symmetrical urea formation | Concentrated to 30 g, cooled to 0° C., filtered. Solids dried under vacuum at 45° C. |
| Purification | Solids from DCM experiment split into two 1.615 g portions:<br>Portion 1 = Triturated at RT with 16 mL (10 vol) 9:1 Heptane:EtOH for ~2.5 h, filtered, washed with heptane<br>Portion 2 = Triturated at RT with 33.6 mL (21 vol) 20:1 Water:1N NaOH aq. soln. for ~2.5 h, filtered, washed with water | NA | NA | NA |
| Yield | Work Up<br>1 = 85%<br>2 = 85%<br>3 = 85%<br>Purification<br>DCM Portion 1 = 99%<br>DCM Portion 2 = 98.84% | 1 = NA<br>2 = 76.29% | NA | 85.51% |
| Amt of impurity at RT = 7.0 and 21.5 min | 1) 7.0 min = 0.28%<br>   21.5 min = 0%<br>2) 7.0 min = 0%<br>   21.5 min = 0%<br>3) 7.0 min = 6.22%<br>   21.5 min = 0% | 1) 7.0 min = 2.92%<br>   21.5 min = 2.85%<br>2) 7.0 min = 0%<br>   21.5 min = 0% | 7.0 min = 0.55%<br>21.5 min = 2.50% | 7.0 min = 0%<br>21.5 min = 0% |
| HPLC purity | Work Up<br>1 = 96.67%<br>2 = 98.19%<br>3 = 93.83%<br>Purification<br>DCM Portion 1 = 97.99%<br>DCM Portion 2 = 98.8% | 2 = 99.7% | 89% | 96.88% |
| Comments | | under anhydrous conditions (N$_2$) | | under anhydrous conditions (N$_2$) |

| Description | Run # 17 | Run # 18 | Run # 19 | Run # 20 |
|---|---|---|---|---|
| Compound (VIII) | 3.0 g (1.0 eq) | 3.0 g (1.0 eq) | 20.0 g (1.0 eq)<br>(Dried KF: 0.2%) | 20.0 g (1.0 eq) |
| 3-amino-5-t-butylisoxazole phenyl carbamate | 2.18 g (1.10 eq) | 2.18 g (1.10 eq) | 13.86 g (1.05 eq) | 14.52 g (1.10 eq) |
| DMAP | 60 mg (0.06 eq) | 60 mg (0.06 eq) | 0.4 g (0.06 eq) | 0.4 g (0.06 eq) |
| TEA | 1.06 mL (1.0 eq) | 1.06 mL (1.0 eq) | 1.06 mL (0.15 eq) | 1.06 mL (0.15 eq) |
| Solvent | 15 mL DMF | 22.5 mL (7.5 vol) DCM | 150 mL (7.5 vol) DCM | 150 mL (7.5 vol) DCM |
| Rxn Temp (° C.) | 60 | 40 | 40 | 40 |
| Rxn Time (Hr) | 4 | 24 | 48 | 40 |
| Work Up | Did not work up | Reaction mixture cooled to 0° C. and filtered and washed with cold DCM | Reaction mixture cooled to 0° C. and filtered and washed with cold DCM | Reaction mixture cooled to 0° C. and filtered and washed with cold DCM |

-continued

| Yield | 63.6% | 81% | 80% |
|---|---|---|---|
| Amt of impurity at RT = 7.0 and 21.5 min | 21.5 min = 2.4% | 2.8 min = 0.35%<br>6.6 min = .7% | 2.8 min = 0.22%<br>6.6 min = 0.2% |
| HPLC purity | 96.7% | 98.6% | 98.7% |

| Description | Run # 21 | Run # 22 |
|---|---|---|
| Compound (VIII) | 20.0 g (1.0 eq) | 1037 g (1.0 eq) |
| 3-amino-5-t-butylisoxazole phenyl carbamate | 13.86 g (1.05 eq) | 718.8 g (1.05 eq) |
| DMAP | 0.4 g (0.06 eq) | 20.75 g (0.06 eq) |
| TEA | 1.06 mL (0.15 eq) | 55.1 mL (1.0 eq) |
| Solvent | 150 mL (7.5 vol) DCM | 7782 mL (7.5 vol) DCM |
| Rxn Temp (° C.) | 40 | 40 |
| Rxn Time (Hr) | 48 h | 21.5 h |
| Work Up | Reaction mixture cooled to 0° C. and filtered and washed with cold DCM | Reaction mixture cooled to 0° C. and filtered and washed with 1500 mL cold DCM |
| Yield | 70% | 68.6% (1010 g) |
| Amt of impurity at RT = 7.0 and 21.5 min | 2.8 min = 0.6% | 21.5 min = 2.4% |
| HPLC purity | 98.5% | 98.5% |
| Comments | | Solids from filtrate = 380 g purity: 88%<br>(6.6 min = 5.2%,<br>21.7 min = 5.1%) |

4. Example F-4

To Reactor A under a nitrogen atmosphere was added 7-(2-morpholin-4-yl-ethoxy)-2-(4-aminophenyl)imidazo[2,1-b]benzothiazole (1 kg) and DMAP (0.02 kg). To Reactor B under a nitrogen atmosphere was added 3-amino-5-t-butyl-isoxazole phenyl carbamate (0.73 kg) and DCM (5.6 L). The DCM used had a water content of less than 0.05% w/w. The mixture in Reactor B was stirred until dissolution. The solution was transferred into Reactor A (the solution can be filtered into Reactor A to remove any insoluble impurities in the carbamate starting material), and the mixture was stirred in Reactor A. Reactor B was washed with DCM (0.8 L) and the wash was transferred into Reactor A. Reactor A was washed with DCM (0.9 L). To Reactor A was added triethylamine (0.1 L) and the charging vessel and lines were rinsed with DCM (0.1 L) into Reactor A. The mixture was then heated to reflux and stirred at reflux until reaction completion (as determined by HPLC to monitor the consumption of starting material).

The reaction mixture was cooled (e.g., over 2 to 3 hours) to a temperature of between −5° C. and 5° C. (e.g., 0° C.). The mixture was then stirred for 2 to 3 hours at a temperature of between −5° C. and 5° C. (e.g., 0° C.). The suspension was filtered. The solid was washed with cool DCM (2×1.5 L) (pre-cooled to a temperature of between −5° C. and 5° C.). The solid was dried under vacuum at a temperature of less than 45° C. until the DCM content was less than 1000 ppm (e.g., below 600 ppm) as analyzed by GC. The desired product was obtained having about 99% purity by HPLC.

G. Preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride

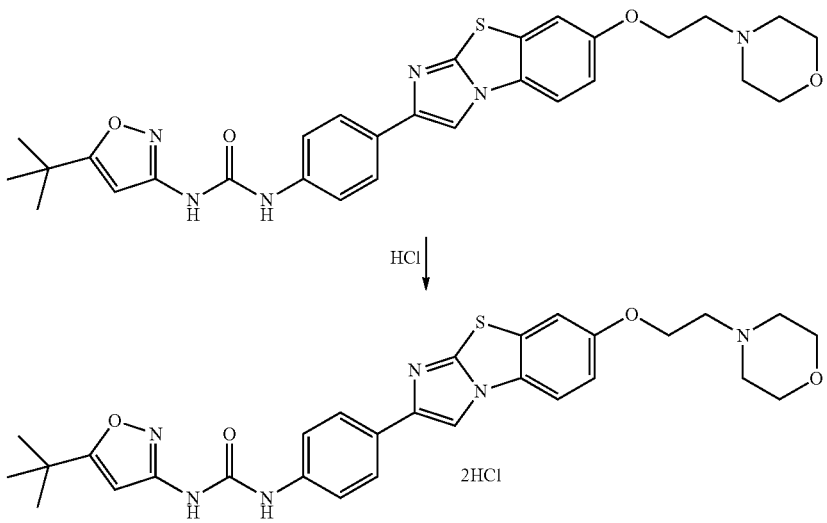

1. Example G-1

The jacket of a 2000-L GL reactor was set to 20° C. and the reactor was charged with N-(5-tert-butyl-isoxazol-3-yl)-N'-{4-[7-(2-morpholin-4-yl-ethoxy)imidazo[2,1-b][1,3]benzothiazol-2-yl]phenyl}urea (35.0 kg, 62.4 mol, 1.0 equiv) followed by methanol (553 kg). Agitation was started and the reaction mixture was heated to reflux (~65° C.). Concentrated aqueous HCl (15.4 kg, 156.0 mol, 2.5 equiv) was charged rapidly (<5 minutes) and the charge line was rinsed into the reactor with methanol (12 kg). Addition of less than 2.0 equivalents of HCl normally resulted in the formation of an insoluble solid. The reaction mixture was heated at reflux for at least 1 hour. Upon HCl addition, the slurry dissolved and almost immediately the salt started to crystallize, leaving insufficient time for a polish filtration.

The reactor was cooled to 20° C. and the product was isolated by filtration (Nutsche) rinsing the reactor and then the cake with methanol (58 kg). The solid was then dried in a vacuum oven (50° C.) to constant weight to give the desired dihydrochloride salt (35 kg, 89% yield, HPLC purity=99.94%). $^1$H NMR (300 MHz, DMSO-$d_6$) conformed to structure.

2. Example G-2

Concentrated HCl was added to a suspension of N-(5-tert-butyl-isoxazol-3-yl)-N'-{4-[7-(2-morpholin-4-yl-ethoxy)imidazo[2,1-b][1,3]benzothiazol-2-yl]phenyl}urea in warm methanol forming a solution that slowly began to precipitate. The reaction mixture was refluxed for over 2 hours and then stirred overnight at ambient temperature. The dihydrochloride salt was collected and dried under vacuum.

3. Example G-3

A 50-L 3-neck round bottom flask was equipped with a mechanical agitator, a thermocouple probe, a nitrogen inlet, a drying tube, a reflux condenser, an addition funnel, and a heating mantle. The flask was charged with N-(5-tert-butyl-isoxazol-3-yl)-N'-{4-[7-(2-morpholin-4-yl-ethoxy)imidazo[2,1-b][1,3]benzothiazol-2-yl]phenyl}urea (775 g, 1.38 mol, 1.0 equiv) and MeOH (40 L, AR). The resulting off-white suspension was heated to reflux (68° C.). A clear solution did not form. HCl (37% aqueous) (228 mL, 3.46 mol, 2.5 equiv) was added over 5 minutes at 68° C. The reaction mixture turned into a clear solution and then a new precipitate formed within approximately 3 minutes. Heating was continued at reflux for approximately 5 hours. The reaction mixture was allowed to cool to ambient temperature overnight. The off-white solids were collected by filtration on a polypropylene filter, washing with MeOH (2×1 L, AR).

Two lots of material prepared in this manner were combined (740 g and 820 g). The combined solids were slurried in methanol (30 L) over 30 minutes at reflux and allowed to cool to the room temperature. The solids were collected by filtration on a polypropylene filter, rinsing with methanol (2×1.5 L). The solids were dried in a vacuum oven (<10 mm Hg) at 40° C. Yield: 1598 g (84%), off-white solid. HPLC: 98.2% (area). MS: 561.2 (M+1)$^+$. $^1$H NMR (300 MHz, DMSO-$d_6$) conformed to the structure. Elemental Analysis (EA): Theory, 54.97% C, 5.41% H, 13.26% N, 5.06% S; 11.19% Cl; Actual, 54.45% C, 5.46% H, 13.09% N, 4.99% S; 10.91% Cl.

4. Example G-4

Into a 50-L 3-neck round bottom flask equipped with a mechanical stirrer, a heating mantle, a condenser and a nitrogen inlet, were charged N-(5-tert-butyl-isoxazol-3-yl)-N'-{4-[7-(2-morpholin-4-yl-ethoxy)imidazo[2,1-b][1,3]benzothiazol-2-yl]phenyl}urea (1052.4 g, 1.877 mol, 1.0 equiv) and methanol (21 L). The reactor was heated and stirred. At an internal temperature of >50° C., conc. HCl (398.63 mL, 4.693 mol, 2.5 equiv) was charged over 5 minutes through an addition funnel. During the addition, the mixture changed from a pale yellow suspension to a white suspension. The internal temperature was 55° C. at the conclusion of the addition. The mixture was heated to reflux for 1 hour, then heating was discontinued and the mixture was allowed to cool to room temperature. The mixture was filtered in two portions, and each filter cake was washed with methanol (2×1 L), transferred to trays and dried in a vacuum oven (45° C.) to constant weight. The dried trays were combined to produce 1141.9 g of the salt (96% yield, 99.1% HPLC purity, 10.9% chloride by titration).

5. Example G-5

The reaction of Step G was carried out in multiple runs under various conditions, such as, e.g., varying equivalents of hydrochloric acid used, reaction time, and/or workup procedures. The results are summarized in the table below.

| Description | Run # 1 | Run # 2 | Run # 3 | Run # 4 | Run # 5 | Run # 6 |
| --- | --- | --- | --- | --- | --- | --- |
| Compound (I) Free Base (g) | 1.5 (1.0 eq) | 5.0 (1.0 eq) | 5.0 (1.0 eq) | 5.0 (1.0 eq) | 5.0 (1.0 eq) | 5.0 (1.0 eq) |
| Conc. HCl | 0.22 mL (0.98 eq) | 0.86 mL (0.98 eq) | 0.86 mL (0.98 eq) | 0.86 mL (0.98 eq) | 1.9 mL (2.5 eq) | 1.9 mL (2.5 eq) |
| Methanol | 75 mL | 158 mL | 200 mL | 150 mL | 150 mL | 150 mL |
| Rxn Temp (° C.) | reflux | reflux | reflux | reflux | reflux | reflux |
| Rxn Time (Hr) | 0.5 | 0.5 | 1.0 | 1.0 | 1.0 | 1.0 |
| Work Up | Reaction mixture cooled in ice bath, filtered, the solids were washed with cold methanol | Reaction mixture concentrated to 72 g and cooled to 0° C., filtered, the solids were washed with cold methanol | Reaction mixture concentrated to 72 g and cooled to 0° C., filtered, the solids were washed with cold methanol | Reaction mixture concentrated to 72 g and cooled to 0° C., filtered, the solids were washed with cold methanol | Reaction mixture concentrated to 72 g and cooled to 0° C., filtered, the solids were washed with cold methanol | Reaction mixture concentrated to 72 g and cooled to RT filtered, the solids were washed with methanol |
| Compound (I) HCl salt (g) | 1.35 | 4.8 | 4.89 | 4.8 | 5.3 | 5.29 |
| Yield | 79% | 85.7% | 86% | 85.6% | 93.6% | 93.6% |
| HPLC purity | 99.2% | 99.4% 99.68% | 99.3% | 98.5% | 97.2% | 98.3% |

-continued

| Comments | HPLC Purity: 99.93% Impurity: 0.07% | SM 89.6% pure. 0.65% sym urea Mono HCl salt | SM 89.6% pure. 0.8% sym urea Mono HCl salt | SM 89.6% pure. 1.16% sym urea Di HCl salt | SM 89.6% pure. 0.63% sym urea Di HCL salt |
|---|---|---|---|---|---|
| Description | Run # 7 | Run # 8 | Run # 9 | Run # 10 | Run # 11 | Run # 12 |
| Compound (I) Free Base (g) | 5.0 (1.0 eq) | 5.0 (1.0 eq) | 3.0 (1.0 eq) | 20.0 (1.0 eq) | 1052.0 (1.0 eq) | 20.0 (1.0 eq) |
| Conc. HCl | 1.9 mL (2.5 eq) | 1.89 mL (2.5 eq) | 1.14 mL (2.5 eq) | 7.58 mL (2.5 eq) | 398.63 mL (2.5 eq) | 7.58 mL (2.5 eq) |
| Methanol | 100 mL | 100 mL (20 vol) | 60 mL (20 vol) | 400 mL (20 vol) | 21048 mL (20 vol) | 400 mL (20 vol) |
| Rxn Temp (° C.) | reflux | reflux | reflux | reflux | reflux | reflux |
| Rxn Time(Hrs) | 1.0 | 1.0 | 10 | 1.0 | 1.0 | 1.0 |
| Work Up | Reaction mixture concentrated to 72 g and cooled to RT, filtered, the solids were washed with methanol | Reaction mixture cooled to RT, filtered, the solids were washed with methanol | Reaction mixture cooled to RT, filtered, the solids were washed with methanol | Reaction mixture cooled to RT, filtered, the solids were washed with methanol | Reaction mixture cooled to RT, filtered, the solids were washed with 2x 1.0 L methanol | Reaction mixture cooled to RT, filtered, the solids were washed with methanol |
| Compound (I) HCl Salt (g) | 5.12 | 5.27 | 3.29 | 21.7 | 1141.9 | 20.37 |
| Yield | 90.6% | 93% | 96.4% | 96% | 96% | 90% |
| HPLC purity | 97.4% | 97.1% | 98.6% | 99.6% | 99.1% | 99.9% |
| Comments | SM 89.6% pure. 0.6% sym urea Di HCl salt | Impurity at 7.0 min = 1.2% | 1.98 min = 0.7% 21.5 min = 0.97% | XRPD taken | XRPD taken; Cl⁻ content = 10.9% | |

H. Analytical Data

1. N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride A batch of about 30 grams of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride was prepared using the methods described herein. This lot was prepared in accordance with the requirements for production of clinical Active Pharmaceutical Ingredients (APIs) under GMP conditions. The analytical data for this batch was obtained, and representative data were provided herein.

Summary of analytical data for the dihydrochloride salt.

| | |
|---|---|
| Appearance | White solid |
| Identity | Retention time of active peak within 2% of reference standards |
| FTIR | Consistent with IR reference standards |
| Mass Spec | Consistent with molecular weight |
| XRPD | Consistent with standard |
| Residue on Ignition | 0.06% |
| Chloride Content | 11.1% |
| HPLC | No impurities ≥ 0.05% detected Total impurity less than 2.0% |
| Assay | 102.4% w/w on anhydrous basis |
| Heavy Metal | <20 ppm |
| Nickel | 0.5 ppm |
| Water | 1.5% |
| Residual Solvent | Methanol < 104 ppm Ethanol < 102 ppm THF < 99 ppm DCM < 94 ppm |

HPLC analysis was performed using the following conditions:

| | |
|---|---|
| Pump | G1311A |
| Autosampler | G1313A |
| Detector | VWD G1314A |
| Column Oven | G1316A |
| Column | Waters XTerra RP18, 5 μm, 4.6 × 150 mm |
| Mobile Phase A | 0.1% $H_3PO_4$ in $H_2O$ |
| Mobile Phase B | 0.1% $H_3PO_4$ in acetonitrile |
| Sample Weights | ~30 mg/50 mL diluent |
| Diluent | 1:1 acetonitrile/water, |
| Flow | 1.0 mL/min |
| Injection Volume | 5 μL |
| Wavelength | 230 nm |
| Temperature | 40° C. |

The HPLC chromatogram was obtained using the above analytical methods over two separate runs. Two 30 mg samples of the above 30 g lot of di-HCl salt were analyzed, and the runs were designated as run A and run B. The HPLC chromatogram for run A and run B are shown in FIGS. 18 and 19, respectively. The average % area values were summarized in the table below. None of the individual impurities including the contemplated symmetrical urea impurity (XI) were above 0.05% area by HPLC relative to total.

| Peak | RT A | RT B | avg RT | RRT | Area % A | Area % B | avg A % |
|---|---|---|---|---|---|---|---|
| 1. | 7.232 | 7.228 | 7.230 | 0.763 | 0.0225 | 0.0265 | 0.0245 |
| 2. | 8.385 | 8.379 | 8.382 | 0.884 | 0.0048 | 0.0046 | 0.0047 |
| 3. | 8.739 | 8.743 | 8.741 | 0.922 | 0.0131 | 0.0138 | 0.0135 |
| 4. | | 8.956 | 8.956 | 0.945 | | 0.0018 | 0.0018 |
| 5. | 9.482 | 9.476 | 9.479 | 1.000 | 99.8072 | 99.8145 | 99.8109 |
| 6. | | 10.435 | 10.435 | 1.101 | | 0.0044 | 0.0044 |
| 7. | 10.643 | 10.634 | 10.639 | 1.122 | 0.0393 | 0.0369 | 0.0381 |
| 8. | 10.745 | 10.736 | 10.741 | 1.133 | 0.0225 | 0.0186 | 0.0206 |
| 9. | 20.973 | 21.077 | 21.025 | 2.218 | 0.0252 | 0.0261 | 0.0257 |
| 10. | 22.912 | 22.903 | 22.908 | 2.417 | 0.0307 | 0.0250 | 0.0279 |
| 11. | 23.004 | | 23.004 | 2.427 | 0.0046 | | 0.0046 |
| 12. | 23.712 | 23.709 | 23.711 | 2.501 | 0.0302 | 0.0277 | 0.0290 |

Additional analytical data for the dihydrochloride salt were obtained and shown in FIGS. 20 to 24.

2. HPLC Analytical Method

HPLC analytical methods used for Examples C-1, D-1, D-4, E, F-1, F-2, F-3, G-1, and G-5 are summarized below.

Samples were diluted in 1:1 acetonitrile/water, methanol, dimethylsulfoxide, 1:1 tetrahydrofuran/water, 0.1% phosphoric acid in 75:25 water/acetonitrile, or 0.1% phosphoric acid in 4:1 water/dimethylsulfoxide. The resulting solution were run on a reverse phase HPLC with UV detection performed at 230 nm. The column temperature was 40° C. The injection volume was 5 μL. The flow rate was 1.0 mL/min. The acquisition time was 25 min plus 5 min post run. The gradient was as follows:

| Time (min)* | % A | % B |
|---|---|---|
| 0.0 | 90 | 10 |
| 8.0 | 55 | 45 |
| 17.0 | 55 | 45 |
| 23.0 | 10 | 90 |
| 25.0 | 10 | 90 |

*Plus 5.0 minute re-equilibration time

Agilent 1100/1200 HPLC system or equivalent was used. A Waters XTerra RP18, 4.6×150 mm, 5 μm column was used. Mobile phase A was 0.1% phosphoric acid in water. Mobile phase B was 0.1% phosphoric acid in acetonitrile. For isolated solids, about 25-30 mg sample being analyzed was accurately weighed and dissolved in the diluent, and analyzed by HPLC. For in-process-control, a sample of the reaction mixture, e.g. about 20-50 μL volume, was diluted with about 2-10 mL of the diluent, if necessary, filtered with a syringe filter, and analyzed by HPLC.

3. HPLC Analytical Method

HPLC analytical method used for FIG. 17, and for Examples A-2, C-2, and D-2, are summarized below.

The HPLC column used was Altima C18 150×4.6 mm, 5μ. Monitoring wavelength was 290 nm Mobile phase A was 0.1% trifluoroacetic acid in water. Mobile phase B was 0.1% trifluoroacetic acid in acetonitrile. The flow rate was 1.5 mL/min. The injection volume was 20 μL. Run time was 15 minutes. Needle wash solution was 1:1 acetonitrile/water (v/v). Diluent was 0.1% trifluoroacetic acid in water. Column temperature was 30° C. Sample compartment was at ambient temperature. The gradient used was as follows:

| Time | % A | % B |
|---|---|---|
| 0 | 80 | 20 |
| 2 | 80 | 20 |
| 7 | 60 | 40 |
| 12 | 60 | 40 |
| 12.1 | 80 | 20 |
| 15 | 80 | 20 |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications, and publications referred to herein are incorporated herein by reference in their entireties. Citation or identification of any reference in this application is not an admission that such reference is available as prior art to this application. The full scope of the disclosure is better understood with reference to the appended claims.

What is claimed:

1. A process for the preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt, solvate, hydrate, or polymorph thereof, comprising the step of reacting 7-(2-morpholin-4-yl-ethoxy)-2-(4-aminophenyl)imidazo[2,1-b]benzothiazole with a 5-tert-butylisoxazol-3-ylcarbamate of Formula (X),

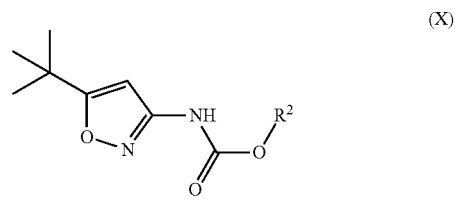

(X)

wherein $R^2$ is aryl or heteroaryl, each of which is optionally substituted with one or more halo, nitro, cyano, alkyl or alkoxyl, to yield N-(5-tert-butyl-isoxazol-3-yl)-N'-{4-[7-(2-morpholin-4-yl-ethoxy)imidazo[2,1-b][1,3]benzo-thiazol-2-yl]phenyl}urea, wherein the reaction is carried out in an aprotic solvent.

2. The process of claim 1, comprising the steps of:

(E) converting 3-amino-5-tert-butyl isoxazole to the 5-tert-butylisoxazol-3-ylcarbamate of Formula (X); and (F) reacting 7-(2-morpholin-4-yl-ethoxy)-2-(4-aminophenyl) imidazo[2,1-b]benzothiazole with the 5-tert-butyl-isoxazol-3-ylcarbamate of Formula (X) to yield N-(5-tert-butyl-isoxazol-3-yl)-N'-{4-[7-(2-morpholin-4-yl-ethoxy)imidazo[2,1-b][1,3]benzo-thiazol-2-yl] phenyl}urea.

3. The process of claim 1, comprising the steps of:

(A) deprotecting a compound of formula (II),

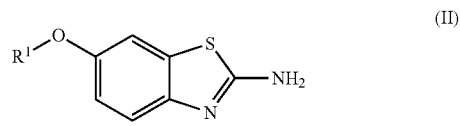

(II)

wherein $R^1$ is a an optionally substituted $C_1$-$C_6$ alkyl, to yield 2-amino-6-hydroxybenzothiazole;

(B) reacting 2-amino-6-hydroxybenzothiazole with a compound of formula (IV),

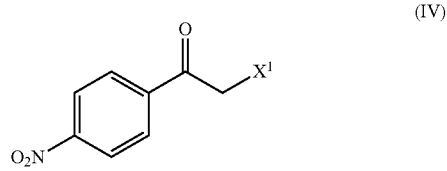

(IV)

wherein $X^1$ is a halo, alkylsulfonate, or arylsulfonate, to yield 2-(4-nitrophenyl)imidazo[2,1-b]benzothiazol-7-ol;

(C) reacting 2-(4-nitrophenyl)imidazo[2,1-b]benzothiazol-7-ol with a compound of formula (VI),

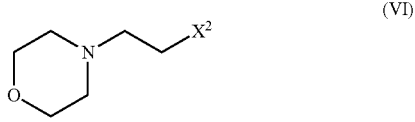

(VI)

wherein X² is a halo, alkylsulfonate, or arylsulfonate, to yield 7-(2-morpholin-4-yl-ethoxy)-2-(4-nitrophenyl)imidazo[2,1-b]benzothiazole;

(D) reducing 7-(2-morpholin-4-yl-ethoxy)-2-(4-nitrophenyl)imidazo[2,1-b]benzothiazole to yield 7-(2-morpholin-4-yl-ethoxy)-2-(4-aminophenyl)imidazo[2,1-b]benzothiazole;

(E) converting 3-amino-5-tert-butyl isoxazole to the 5-tert-butylisoxazol-3-ylcarbamate of Formula (X); and (F) reacting 7-(2-morpholin-4-yl-ethoxy)-2-(4-aminophenyl) imidazo[2,1-b]benzothiazole with the 5-tert-butylisoxazol-3-ylcarbamate of Formula (X) to yield N-(5-tert-butyl-isoxazol-3-yl)-N'-{4-[7-(2-morpholin-4-yl-ethoxy)imidazo[2,1-b][1,3]benzo-thiazol-2-yl]phenyl}urea.

4. The process of claim 3, further comprising the step of:

(G) converting a free base of N-(5-tert-butyl-isoxazol-3-yl)-N'-{4-[7-(2-morpholin-4-yl-ethoxy)imidazo[2,1-b][1,3]benzo-thiazol-2-yl]phenyl}urea to an acid addition salt of N-(5-tert-butyl-isoxazol-3-yl)-N'-{4-[7-(2-morpholin-4-yl-ethoxy)imidazo[2,1-b][1,3]benzo-thiazol-2-yl]phenyl}urea.

5. The process of claim 3, wherein R¹ is methyl.

6. The process of claim 3, wherein X¹ is bromo.

7. The process of claim 3, wherein X² is chloro.

8. The process of claim 1, wherein R² is phenyl.

9. The process of claim 3, wherein the reaction of Step A is carried out in the presence of aqueous hydrobromic acid.

10. The process of claim 3, wherein the reaction of Step A is carried out at a temperature of between about 105° C. and about 110° C.

11. The process of claim 3, wherein the reaction of Step B is carried out in the presence of a carbonate or bicarbonate salt.

12. The process of claim 11, wherein the carbonate or bicarbonate salt is sodium bicarbonate.

13. The process of claim 3, wherein the reaction of Step B is carried out in an alcohol solvent.

14. The process of claim 13, wherein the reaction of Step B is carried out in n-butanol.

15. The process of claim 3, wherein the reaction of Step B is carried out at a temperature of between about 110° C. and about 115° C.

16. The process of claim 3, wherein the reaction of Step C is carried out in the presence of a carbonate or bicarbonate salt.

17. The process of claim 16, wherein the carbonate or bicarbonate salt is potassium carbonate.

18. The process of claim 3, wherein the reaction of Step C is carried out in the presence of a phase transfer reagent.

19. The process of claim 18, wherein the phase transfer reagent is tetrabutylammonium iodide.

20. The process of claim 3, wherein the reaction of Step C is carried out in the presence of potassium carbonate and tetrabutylammonium iodide.

21. The process of claim 3, wherein the reaction of Step C is carried out in N,N-dimethylformamide.

22. The process of claim 3, wherein the reaction of Step C is carried out at a temperature of between about 90° C. and about 110° C.

23. The process of claim 3, wherein the reaction of Step D is carried out in the presence of a reducing agent or catalyst.

24. The process of claim 23, wherein the reducing agent or catalyst is Raney nickel.

25. The process of claim 3, wherein the reaction of Step D is carried out under a hydrogen atmosphere.

26. The process of claim 25, wherein the hydrogen is at a pressure of between about 200 psi and about 300 psi.

27. The process of claim 26, wherein the hydrogen pressure is about 150 psi.

28. The process of claim 3, wherein the reaction of Step D is carried out in a polar solvent.

29. The process of claim 28, wherein the polar solvent is a mixture of methanol and tetrahydrofuran.

30. The process of claim 3, wherein the reaction of Step D is carried out at a temperature of about 50° C.

31. The process of claim 3, wherein the reaction of Step E is carried out in the presence of a haloformate reagent.

32. The process of claim 31, wherein the haloformate reagent is phenyl chloroformate.

33. The process of claim 3, wherein the reaction of Step E is carried out in the presence of a base.

34. The process of claim 33, wherein the base is a carbonate or bicarbonate salt.

35. The process of claim 34, wherein the base is potassium carbonate.

36. The process of claim 3, wherein the reaction of Step E is carried out in a polar solvent.

37. The process of claim 36, wherein the polar solvent is tetrahydrofuran.

38. The process of claim 3, wherein the reaction of Step E is carried out at a temperature of about 20° C.

39. The process of claim 3, wherein the reaction of Step F is carried out in the presence of a base.

40. The process of claim 39, wherein the base is triethylamine.

41. The process of claim 3, wherein the reaction of Step F is carried out in the presence of a catalyst.

42. The process of claim 41, wherein the catalyst is 4-dimethylaminopyridine.

43. The process of claim 1, wherein the aprotic solvent is dichloromethane.

44. The process of claim 3, wherein the reaction of Step F is carried out at a temperature of about 40° C.

45. The process of claim 3, wherein the molar ratio of the 5-tert-butylisoxazol-3-ylcarbamate of Formula (X) relative to 7-(2-morpholin-4-yl-ethoxy)-2-(4-aminophenyl)imidazo[2,1-b]benzothiazole used in the reaction of Step F is between about 1.0 and about 1.5.

46. The process of claim 4, wherein the reaction of Step G is carried out in the presence of hydrochloric acid and the acid addition salt of Step G is a hydrochloride salt.

47. The process of claim 46, wherein the acid addition salt of Step G is a dihydrochloride salt.

48. The process of claim 4, wherein the product of each of the reactions of Steps A, B, C, D, E, F, and G is isolated by filtration or centrifuge.

49. The process of claim 48, wherein the yield of the isolated product of each of the reactions of Steps A, B, C, D, E, F, and G is greater than about 80%.

50. The process of claim 48, wherein the purity of the isolated product of each of the reactions of Steps A, B, C, D, E, F, and G is greater than about 97%.

* * * * *